US007855212B2

(12) United States Patent
Schwarz et al.

(10) Patent No.: US 7,855,212 B2
(45) Date of Patent: Dec. 21, 2010

(54) PYRIDINYL ACETONITRILES

(75) Inventors: Matthias Schwarz, Geneva (CH);
Pascale Gaillard, Collonges sous Saleve (FR); Jean-Pierre Gotteland, Beaumont (FR); Russell J. Thomas, Siena (IT); Patrick Page, Saint-Julien-en-Genevois (FR)

(73) Assignee: Merck Serono SA, Coinsins (CH)

( * ) Notice: Subject to any disclaimer, the term of this patent is extended or adjusted under 35 U.S.C. 154(b) by 0 days.

(21) Appl. No.: 10/555,960

(22) PCT Filed: May 3, 2004

(86) PCT No.: PCT/EP2004/004808

§ 371 (c)(1),
(2), (4) Date: Nov. 16, 2006

(87) PCT Pub. No.: WO2004/098607

PCT Pub. Date: Nov. 18, 2004

(65) Prior Publication Data

US 2007/0060594 A1    Mar. 15, 2007

(30) Foreign Application Priority Data

May 8, 2003    (EP) .................................. 03101281

(51) Int. Cl.
| | |
|---|---|
| A01N 43/54 | (2006.01) |
| C07D 239/42 | (2006.01) |
| C07D 401/04 | (2006.01) |
| C07D 239/02 | (2006.01) |
| C07D 401/00 | (2006.01) |
| C07D 403/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| A61K 31/505 | (2006.01) |

(52) U.S. Cl. ...................... 514/256; 514/269; 514/272; 514/275; 544/329; 544/333

(58) Field of Classification Search ........................ None
See application file for complete search history.

(56) References Cited

U.S. PATENT DOCUMENTS 2,676,964 A    4/1954    Papa et al.

FOREIGN PATENT DOCUMENTS

| EP | 461 079 | 12/1991 |
| EP | 752 424 | 1/1997 |
| EP | 1 110 957 | 6/2001 |
| WO | 02/20495 | 3/2002 |
| WO | 03/030909 | 4/2003 |

OTHER PUBLICATIONS

Newkome, et. al., Organometallics (1988), 7(12), 2537-42.*
http://www.nlm.nih.gov/cgi/mesh/2009/MB_cgi?mode=&index=18275&field=all&HM=&II=&PA=&form=&input, last accessed Jan. 3, 2009.*
National Library of Medicine website, http://www.nlm.nih.gov/cgi/mesh/2009/MB_cgi, last accessed Jan. 3, 2009.*
Zhi-Tang Huang et al., "Synthesis, reactions, and tautomerism of ketene N, S-acetals with benzothiazoline ring", Chemische Berichte, vol. 123, No. 3, pp. 541-547 1990.
James R. Woodgett, "A common denominator linking glycogen metabolism, nuclear oncogenes and development", Trends Biochem. Sci., vol. 16, pp. 177-181 1991.
Simon Lovestone, et al, "Alzheimer's disease-like phosphorylation of the microtubule-associated protein tau by glycogen synthase kinase-3 in transfected mammalian cells", Current Biology, vol. 4, No. 12, pp. 1077-1086 1994.
Janet Brownlees, et al., "Tau phosphorylation in transgenic mice expressing glycogen synthase kinase-3β transgenes", Neuroreport, vol. 8, pp. 3251-3255 1997.
Akihiko Takashima et al, "Presenilin 1 associates with glycogen synthase kinase-3β and its substrate tau", Proc. Natl. Acad. Sci. USA, vol. 95, pp. 9637-9641 1998.
Zhuohua Zhang, et al., "Destabilization of β-catenin by mutations in presenilin-1 potentiates neuronal apoptosis", Nature, vol. 395, pp. 698-702 Oct. 15, 1998.
Akihiko Takashima et al, "Tau protein kinase I is essential for amyloid β-protein-induced neurotoxicity", Proc. Natl. Acad. Sci. USA, vol. 90, pp. 7789-7793 1993.
Jin-Jing Pei, et al., "Distribution, levels, and activity of glycogen synthase kinase-3 in the Alzheimer disease Brain", Journal of Neuropathology and Experimental Neurology, vol. 56, No. 1, pp. 70-78 1997.
Guang Chen, et al., "The mood-stabilizing agent valproate inhibits the activity of glycogen synthase kinase-3", Journal of Neurochemistry, vol. 72, No. 3, pp. 1327-1330 1999.
Shigeyuki Nonaka, et al, "Chronic lithium treatment robustly protects neurons in the central nervous system against excitotoxicity by inhibiting N-methyl-d-aspartate receptor-mediated calcium influx", Proc. Natl. Acad. Sci. USA, vol. 95, pp. 2642-2647 1998.
Robert Joseph Thomas, "Excitatory amino acids in health and disease", J. Am. Geriatr. Soc., vol. 43, pp. 1279-1289 1995.

(Continued)

*Primary Examiner*—James O Wilson
*Assistant Examiner*—Jeffrey H Murray
(74) *Attorney, Agent, or Firm*—Oblon, Spivak, McClelland, Maier & Neustadt, L.L.P.

(57) ABSTRACT

The present invention is related to pyridinyl acetonitriles as well as to pharmaceutical formulations containing such pyridinyl acetonitriles. Said pyridinyl acetonitriles are modulators of the protein kinase signalling pathways, particularly the one involving Glycogen Kinase Synthase 3 or JNK. The present invention is furthermore related to methods of preparing pyridinyl acetonitriles. X is a substituted or unsubstituted pyridinyl. G is an unsubstituted or substituted pyrimidinyl or triazinyl.

6 Claims, No Drawings

OTHER PUBLICATIONS

Chihoko Sasaki et al, "Different expression of glycogen synthase kinase-3β between young and old rat brains after transient middle cerebral artery occlusion", Neurological Research, vol. 23, pp. 588-592 2001.

Darren A. E. Cross, et al, "Selective small-molecule inhibitors of glycogen synthase kinase-3 activity protect primary neurones from death", Journal of Neurochemistry, vol. 77, pp. 94-102 2001.

Adnan Ali et al, "Glycogen synthase kinase-3: properties, functions, and regulation", Chemical Reviews 2000.

* cited by examiner

PYRIDINYL ACETONITRILES

FIELD OF THE INVENTION

The present invention is related to pyridinyl acetonitriles, as well as pharmaceutical compositions containing such pyridinyl acetonitriles. In particular, the present invention is related to the modulation, notably the inhibition of the protein kinase pathway by using pyridinyl acetonitriles of the present invention. Preferred protein kinases are Glycogen Synthase Kinase 3 (GSK3) and JNK. The compounds of the present invention are particularly useful in the treatment of neurodegenerative diseases, neuronal disorders, inflammatory diseases, cardiovascular diseases, cancer or metabolic disorders mediated by insulin resistance or hyperglycemia, comprising diabetes type I and/or II, inadequate glucose tolerance, insulin resistance, obesity, polycystic ovary syndrome (PCOS). The present invention furthermore relates to methods for the preparation of pyridinyl acetonitriles.

BACKGROUND OF THE INVENTION

Cellular signaling has become a major research theme in biology and medicine over the past twenty years. The complex pathways and protein components in signal transduction are emerging with increasing clarity. Over the last 15 years, the protein kinases, such as the protein tyrosine kinases, have been identified as key players in cellular regulation. They are involved in immune, endocrine, and nervous system physiology and pathology and thought to be important in the development of many cancers. As such they serve as drug targets for many different diseases. Members of protein kinase family include for example c-Jun N-terminal kinase (JNK) or Glycogen Synthase Kinase 3 (GSK3).

Glycogen synthase kinase 3 (GSK3) is a serine/threonine kinase for which two isoforms, α and β, have been identified (*Trends Biochem. Sci.*, 16 p. 177-81 (1991) by Woodgett et al.). Both GSK3 isoforms are constitutively active in resting cells. GSK3 was originally identified as a kinase that inhibits glycogen synthase by direct phosphorylation. Upon insulin activation, GSK3 is inactivated, thereby allowing the activation of glycogen synthase and possibly other insulin-dependent events, such glucose transport. Subsequently, it has been shown that GSK3 activity is also inactivated by other growth factors that, like insulin, signal through receptor tyrosine kinases (RTKs). Examples of such signalling molecules include IGF-1 and EGF. GSK3 beta activity is regulated by serine (inhibitory) and tyrosine (stimulatory) phosphorylation, by protein complex formation, and by its intracellular localization. GSK3 beta phosphorylates and thereby regulates the functions of many metabolic, signalling and structural proteins. Notable among the signalling proteins regulated by GSK3 beta are the many transcription factors, including activator protein-1 cells, Myc, beta-catenin, CCAAT/enhancer binding protein, and NFkappaB.

Agents that inhibit GSK3 activity are useful in the treatment of disorders that are mediated by GSK3 activity. In addition, inhibition of GSK3 mimics the activation of growth factor signalling pathways and consequently GSK3 inhibitors are useful in the treatment of diseases in which such pathways are insufficiently active. Examples of diseases that can be treated with GSK3 inhibitors, such as diabetes, neurodegenerative diseases (e.g. Alzheimer's disease), inflammatory diseases, ischemia and cancer are described below.

In the patent literature, different classes of GSK3 inhibitors have been disclosed (e.g. WO 02/20495, Chiron Corporation; WO 02/10141, Pfizer Products Inc.; WO 02/22608, Vertex Pharmaceuticals Inc.).

Diabetes mellitus is a serious metabolic disease that is defined by the presence of chemically elevated levels of blood glucose (hyperglycemia). The term diabetes mellitus encompasses several different hyperglycemic states. These states include Type 1 (insulin-dependent diabetes mellitus or IDDM) and Type 2 (non-insulin dependent diabetes mellitus or NIDDM) diabetes. The hyperglycemia present in individuals with Type 1 diabetes is associated with deficient, reduced, or nonexistent levels of insulin that are insufficient to maintain blood glucose levels within the physiological range. Conventionally, Type 1 diabetes is treated by administration of replacement doses of insulin, generally by a parenteral route. Type 1 diabetes constitutes an auto-immune disorder and may therefore be treated by compounds that modulate the JNK signaling.

Type 2 diabetes is an increasingly prevalent disease of aging. It is initially characterized by decreased sensitivity to insulin and a compensatory elevation in circulating insulin concentrations, the latter of which is required to maintain normal blood glucose levels. As described above, GSK3 inhibition stimulates insulin-dependent processes and is consequently useful in the treatment of type 2 diabetes. Recent data obtained using lithium salts provides evidence for this notion.

GSK3 is also involved in biological pathways relating to Alzheimer's disease (AD). The characteristic pathological features of AD are extracellular plaques of an abnormally processed form of the amyloid precursor protein (APP), so-called β-amyloid peptide (β-AP) and the development of intracellular neurofibrillary tangles containing paired helical filaments (PHF) that consists largely of hyperphosphorylated tau protein. GSK3 is one of a number of a number of kinases that have been found to phosphorylate tau protein in vitro on the abnormal sites characteristic of PHF tau, and is the only kinase also demonstrated to do this in living cells and in animals (*Current Biology* 4 p. 1077-86 (1994) by Lovestone et al. and *Neuroreport* 8 p. 3251-55 (1997) by Brownlees et al.).

Recently it has been shown that GSK3b associates with another key protein in AD pathogenesis, presenillin 1 (PS1) (*PNAS* 95 p. 9637-41 (1998) by Takashima et al.). Mutations in the PS1 gene lead to increased production of β-AP, but the authors also demonstrate that the mutant PS1 proteins bind more tightly to GSK3 P and potentiate the phosphorylation of tau, which is bound to the same region of PS1. Interestingly it has also been shown that another GSK3 substrate, β-catenin, binds to PS1 (*Nature* 395 p. 698-702 (1998) by Zhong et al.). Cytosolic β-catenin is targeted for degradation upon phosphorylation by GSK3 and reduced β-catenin activity is associated with increased sensitivity of neuronal cells to β-AP induced neuronal apoptosis. Consequently, increased association of GSK3β with mutant PS1 may account for the reduced levels of β-catenin that have been observed in the brains of PS1-mutant AD patients and to the disease related increase in neuronal cell-death. Consistent with these observations, it has been shown that injection of GSK3 anti-sense but not sense, blocks the pathological effects of β-AP on neurons in vitro, resulting in a 24 hr delay in the onset of cell death (*PNAS* 90 p. 7789-93 (1993) by Takashima et al.). In these latter studies, the effects on cell-death are preceded (within 3-6 hours of β-AP administration) by a doubling of intracellular GSK3 activity, suggesting that genetic mechanisms may increase GSK3 activity. Further evidence for a role for GSK3 in AD is provided by the observation that the protein expression level of GSK3 is increased by 50% in post-synaptosomal supernatants of AD vs. normal brain tissue (*J. Neuropathol. Exp.* 56 p. 70-78 (1997) by Pei et al.). Thus, it is believed that specific inhibitors of GSK3 will act to slow the progression of Alzheimer's Disease.

It has also been described an involvement of GSK3 activity in the etiology of bipolar disorder. In support of this notion it was recently shown that valproate—which is a further drug commonly used in the treatment of said disease—is also a GSK3 inhibitor (*J. Neurochemistry* 72 p. 1327-30 (1999)). One mechanism by which lithium and other GSK3 inhibitors may act to treat bipolar disorder is to increase the survival of neurons subjected to aberrantly high levels of excitation induced by the neurotransmitter, glutamate (*PNAS* 95 p. 2642-47 (1998) by Nonaka et al.).

Glutamate-induced neuronal excito-toxicity is also believed to be a major cause of neurodegeneration associated with acute damage such as in cerebral ischemia, traumatic brain injury and bacterial infection. Furthermore, it is believed that excessive glutamate signalling is a factor in the chronic neuronal damage seen in diseases such as Alzheimer's, Huntingdon's, Parkinson's, AIDS associated dementia, amyotrophic lateral sclerosis (AML) and multiple sclerosis (MS) (*J. Am. Geriatr. Soc.* 43 p. 1279-89 (1995) by Thomas et al.). Consequently, GSK3 inhibitors are believed to be a useful treatment in these and other neurodegenerative disorders.

Sasaki et al. disclosed that GSK3 beta may have a role in ischemic neuronal cell death (*Neurol. Res.* 23(6) p. 588-92 (2001) by Sasaki C. et al.). Darren A. E. et al. described selective small-molecule inhibitors of glycogen synthase kinase-3 activity protecting primary neurones from death (*Journal of Neurochemistry* 77 p. 94-102 (2001)).

It has also been reported that debromohymenialdisine ((4Z)-4-(2-amino-5-oxo-3,5-dihydro-4H-imidazol-4-ylidene)-4,5,6,7-tetrahydropyrrolo(2,3-c)azepin-8(1H)-one), considered as inhibitors of GSK3, exhibit anti-inflammatory activity in a model of adjuvant-induced arthritis in the rat. (A. Ali et al., *Chem. Rev.* p. A-N (December 2000)).

EP-752,424 (Kumia Chemical Industry Co. LTD) relates to nicotinic derivatives having the formula (A):

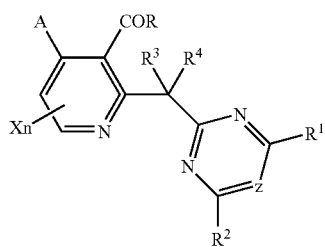

(A)

The compounds (A) are said to be herbicides.

Further pyridinyl derivatives for use a herbicides are disclosed in EP-461,079.

A further protein tyrosine kinases which is involved in cellular regulation is C-Jun N-Terminal kinase (JNK). JNK is a member of the MAP Kinase family that includes the extracellular regulated kinases (ERKs) and p 38 kinases. It is a serine/threonine kinase that phosphorylates c-Jun, a transcription factor activator protein-1 (AP-1) component. AP-1 regulates the transcription of several genes including inflammatory enzymes (COX-2), matrix metalloproteinases (MMP-13), cytokines (TNF), growth factors (VEGF) and immunoglobulins. Three JNK isoforms, JNK-1, -2 and -3, have been identified in humans and they appear to mediate critical phosphorylation events involved in the regulation of apoptosis and the immune response. One of the first inhibitors of the JNK pathway is Cephalon's CEP-1347 (*J. Med. Chem.* 40, p. 1836-9 (1997)) which was found to be neuroprotective in a number of in vivo models of neurodegenerative disease. Several compounds are reported in the patent literature to inhibit JNKs. Hoffmann-La Roche claimed 4-heteroaryl, 4-arylindolinones and annulated indolinones (WO 0035921, WO 0035909 and WO 0035906). Vertex Pharmaceuticals disclosed oxime derivatives as a JNK3 inhibitor (WO0064872).

WO 01/47920 discloses benzothiazole derivatives as JNK inhibitors of formula (A).

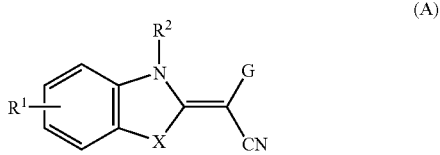

(A)

WO 03/030909 discloses meta pyridinyl acetonitriles and specifically:

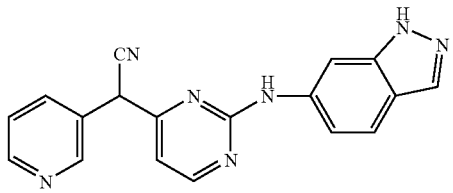

The compounds are said to be useful in the treatment of cancer and viral infections.

SUMMARY OF THE INVENTION

The present invention relates to pyridinyl acetonitriles of formula (I)

(I)

as well as their pharmaceutically acceptable salts for the treatment and/or prevention of neuronal disorders, neurodegenerative diseases, cardiovascular diseases, inflammatory diseases, metabolic disorders or metabolic disorders mediated by insulin resistance or hyperglycemia, comprising diabetes type I and/or II, inadequate glucose tolerance, insulin resistance, obesity, polycystic ovary syndrome (PCOS), bipolar disease. According to one embodiment, the compounds of this invention are inhibitors of the protein kinases, e.g. of Glycogen Synthase Kinase 3 (GSK3).

DETAILED DESCRIPTION OF THE INVENTION

The following paragraphs provide definitions of the various chemical moieties that make up the compounds according to the invention and are intended to apply uniformly throughout the specification and claims unless an otherwise expressly set out definition provides a broader definition.

"$C_1$-$C_6$-alkyl" refers to alkyl groups having 1 to 6 carbon atoms. This term is exemplified by groups such as methyl, ethyl, n-propyl, isopropyl, n-butyl, isobutyl, tert-butyl, n-hexyl and the like.

"Aryl" refers to an unsaturated aromatic carbocyclic group of from 6 to 14 carbon atoms having a single ring (e.g., phenyl) or multiple condensed rings (e.g., naphthyl). Preferred aryl include phenyl, naphthyl, phenantrenyl and the like.

"$C_1$-$C_6$-alkyl aryl" refers to $C_1$-$C_6$-alkyl groups having an aryl substituent, including benzyl, phenethyl and the like.

"Heteroaryl" refers to a monocyclic heteroaromatic, or a bicyclic or a tricyclic fused-ring heteroaromatic group. Particular examples of heteroaromatic groups include optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

"$C_1$-$C_6$-alkyl heteroaryl" refers to $C_1$-$C_6$-alkyl groups having a heteroaryl substituent, including 2-furylmethyl, 2-thienylmethyl, 2-(1H-indol-3-yl)ethyl and the like.

"$C_2$-$C_6$-alkenyl" refers to alkenyl groups preferably having from 2 to 6 carbon atoms and having at least 1 or 2 sites of alkenyl unsaturation. Preferable alkenyl groups include ethenyl (—CH=$CH_2$), n-2-propenyl (allyl, —$CH_2$CH=$CH_2$) and the like.

"$C_2$-$C_6$-alkenyl aryl" refers to $C_2$-$C_6$-alkenyl groups having an aryl substituent, including 2-phenylvinyl and the like.

"$C_2$-$C_6$-alkenyl heteroaryl" refers to $C_2$-$C_6$-alkenyl groups having a heteroaryl substituent, including 2-(3-pyridinyl)vinyl and the like.

"$C_2$-$C_6$-alkynyl" refers to alkynyl groups preferably having from 2 to 6 carbon atoms and having at least 1-2 sites of alkynyl unsaturation, preferred alkynyl groups include ethynyl (—C≡CH), propargyl (—$CH_2$C≡CH), and the like.

"$C_2$-$C_6$-alkynyl aryl" refers to $C_2$-$C_6$-alkynyl groups having an aryl substituent, including phenylethynyl and the like.

"$C_2$-$C_6$-alkynyl heteroaryl" refers to $C_2$-$C_6$-alkynyl groups having a heteroaryl substituent, including 2-thienylethynyl and the like.

"$C_3$-$C_8$-cycloalkyl" refers to a saturated carbocyclic group of from 3 to 8 carbon atoms having a single ring (e.g., cyclohexyl) or multiple condensed rings (e.g., norbornyl). Preferred cycloalkyl include cyclopentyl, cyclohexyl, norbornyl and the like.

"$C_1$-$C_6$-alkyl cycloalkyl" refers to $C_1$-$C_6$-alkyl groups having a cycloalkyl substituent, including cyclohexylmethyl, cyclopentylpropyl, and the like.

"heterocycloalkyl" refers to a $C_3$-$C_8$-cycloalkyl group according to the definition above, in which 1 to 3 carbon atoms are replaced by hetero atoms chosen from the group consisting of O, S, NR, R being defined as hydrogen or $C_1$-$C_6$ alkyl. Preferred heterocycloalkyl include pyrrolidine, piperidine, piperazine, 1-methylpiperazine, morpholine, and the like.

"$C_1$-$C_6$-alkyl heterocycloalkyl" refers to $C_1$-$C_6$-alkyl groups having a heterocycloalkyl substituent, including 2-(1-pyrrolidinyl)ethyl, 4-morpholinylmethyl, (1-methyl-4-piperidinyl)methyl and the like.

"Carboxy" refers to the group —C(O)OH.

"$C_1$-$C_6$-alkyl carboxy" refers to $C_1$-$C_6$-alkyl groups having a carboxy substituent, including 2-carboxyethyl and the like.

"Acyl" refers to the group —C(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyl" refers to $C_1$-$C_6$-alkyl groups having an acyl substituent, including 2-acetylethyl and the like.

"Aryl acyl" refers to aryl groups having an acyl substituent, including 2-acetylphenyl and the like.

"Heteroaryl acyl" refers to hetereoaryl groups having an acyl substituent, including 2-acetylpyridyl and the like.

"$C_3$-$C_8$-(hetero)cycloalkyl acyl" refers to 3 to 8 membered cycloalkyl or heterocycloalkyl groups having an acyl substituent.

"Acyloxy" refers to the group —OC(O)R where R includes H, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acyloxy" refers to $C_1$-$C_6$-alkyl groups having an acyloxy substituent, including 2-(acetyloxy)ethyl and the like.

"Alkoxy" refers to the group —O—R where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxy" refers to $C_1$-$C_6$-alkyl groups having an alkoxy substituent, including 2-ethoxyethyl and the like.

"Alkoxycarbonyl" refers to the group —(O)OR where R includes "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl alkoxycarbonyl" refers to $C_1$-$C_6$-alkyl groups having an alkoxycarbonyl substituent, including 2-(benzyloxycarbonyl)ethyl and the like.

"Aminocarbonyl" refers to the group —C(O)NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminocarbonyl" refers to $C_1$-$C_6$-alkyl groups having an aminocarbonyl substituent, including 2-(dimethylaminocarbonyl)ethyl and the like.

"Acylamino" refers to the group —NRC(O)R' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl acylamino" refers to $C_1$-$C_6$-alkyl groups having an acylamino substituent, including 2-(propionylamino) ethyl and the like.

"Ureido" refers to the group —NRC(O)NR'R" where each R, R', R" is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R' and R", together with the nitrogen atom to which they are attached, can optionally form a 3-8-membered heterocycloalkyl ring.

"$C_1$-$C_6$-alkyl ureido" refers to $C_1$-$C_6$-alkyl groups having an ureido substituent, including 2-(N'-methylureido)ethyl and the like.

"Carbamate" refers to the group —NRC(O)OR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"Amino" refers to the group —NRR' where each R, R' is independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl amino" refers to $C_1$-$C_6$-alkyl groups having an amino substituent, including 2-(1-pyrrolidinyl)ethyl and the like.

"Ammonium" refers to a positively charged group —N$^+$RR'R", where each R, R', R" is independently, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl", and where R and R', together with the nitrogen atom to which they are attached, can optionally form a 3-8-membered heterocycloalkyl ring.

"$C_1$-$C_6$-alkyl ammonium" refers to $C_1$-$C_6$-alkyl groups having an ammonium substituent, including 2-(1-pyrrolidinyl)ethyl and the like.

"Halogen" refers to fluoro, chloro, bromo and iodo atoms.

"Sulfonyloxy" refers to a group —OSO$_2$—R wherein R is selected from H, "$C_1$-$C_6$-alkyl", "$C_1$-$C_6$-alkyl" substituted with halogens, e.g., an —OSO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyloxy" refers to $C_1$-$C_6$-alkyl groups having a sulfonyloxy substituent, including 2-(methylsulfonyloxy)ethyl and the like.

"Sulfonyl" refers to group "—SO$_2$—R" wherein R is selected from H, "aryl", "heteroaryl", "$C_1$-$C_6$-alkyl", "$C_1$-$C_6$-alkyl" substituted with halogens, e.g., an —SO$_2$—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonyl" refers to $C_1$-$C_6$-alkyl groups having a sulfonyl substituent, including 2-(methylsulfonyl)ethyl and the like.

"Sulfinyl" refers to a group "—S(O)—R" wherein R is selected from H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfinyl" refers to $C_1$-$C_6$-alkyl groups having a sulfinyl substituent, including 2-(methylsulfinyl)ethyl and the like.

"Sulfanyl" refers to groups —S—R where R includes H, "$C_1$-$C_6$-alkyl", "$C_1$-$C_6$-alkyl" substituted with halogens, e.g., an —SO—CF$_3$ group, "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl". Preferred sulfanyl groups include methylsulfanyl, ethylsulfanyl, and the like.

"$C_1$-$C_6$-alkyl sulfanyl" refers to $C_1$-$C_6$-alkyl groups having a sulfanyl substituent, including 2-(ethylsulfanyl)ethyl and the like.

"Sulfonylamino" refers to a group —NRSO$_2$—R' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl sulfonylamino" refers to $C_1$-$C_6$-alkyl groups having a sulfonylamino substituent, including 2-(ethylsulfonylamino)ethyl and the like.

"Aminosulfonyl" refers to a group —SO$_2$—NRR' where each R, R' includes independently hydrogen, "$C_1$-$C_6$-alkyl", "$C_2$-$C_6$-alkenyl", "$C_2$-$C_6$-alkynyl", "$C_3$-$C_8$-cycloalkyl", "heterocycloalkyl", "aryl", "heteroaryl", "$C_1$-$C_6$-alkyl aryl" or "$C_1$-$C_6$-alkyl heteroaryl", "$C_2$-$C_6$-alkenyl aryl", "$C_2$-$C_6$-alkenyl heteroaryl", "$C_2$-$C_6$-alkynyl aryl", "$C_2$-$C_6$-alkynylheteroaryl", "$C_1$-$C_6$-alkyl cycloalkyl", "$C_1$-$C_6$-alkyl heterocycloalkyl".

"$C_1$-$C_6$-alkyl aminosulfonyl" refers to $C_1$-$C_6$-alkyl groups having an aminosulfonyl substituent, including 2-(cyclohexylaminosulfonyl)ethyl and the like.

"Substituted or unsubstituted": Unless otherwise constrained by the definition of the individual substituent, the above set out groups, like "alkyl", "alkenyl", "alkynyl", "aryl" and "heteroaryl" etc. groups can optionally be substituted with from 1 to 5 substituents selected from the group consisting of "$C_1$-$C_6$-alkyl", "$C_2$-$C_6$-alkenyl", "$C_2$-$C_6$-alkynyl", "cycloalkyl", "heterocycloalkyl", "$C_1$-$C_6$-alkyl aryl", "$C_1$-$C_6$-alkyl heteroaryl", "$C_1$-$C_6$-alkyl cycloalkyl", "$C_1$-$C_6$-alkyl heterocycloalkyl", "amino", "ammonium", "acyl", "acyloxy", "acylamino", "aminocarbonyl", "alkoxycarbonyl", "ureido", "carbamate", "aryl", "heteroaryl", "sulfinyl", "sulfonyl", "alkoxy", "sulfanyl", "halogen", "carboxy", trihalomethyl, cyano, hydroxy, mercapto, nitro, and the like. Alternatively said substitution could also comprise situations where neighbouring substituents have undergone ring closure, notably when vicinal functional substituents are involved, thus forming, e.g., lactams, lactons, cyclic anhydrides, but also acetals, thioacetals, aminals formed by ring closure for instance in an effort to obtain a protective group.

"Pharmaceutically acceptable salts or complexes" refers to salts or complexes of the below-identified compounds of formulae (I), (Ia) and (Ib) that retain the desired biological activity. Examples of such salts include, but are not restricted to acid addition salts formed with inorganic acids (e.g. hydrochloric acid, hydrobromic acid, sulfuric acid, phosphoric acid, nitric acid, and the like), and salts formed with organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, methanesulfonic acid and poly-galacturonic acid. Said compounds can also be administered as pharmaceutically acceptable quaternary salts known by a person skilled in the art, which specifically include the quarternary ammonium salt of the formula —NR, R', R"+Z−, wherein R, R', R" is independently hydrogen, alkyl, or benzyl, $C_1$-$C_6$-alkyl, $C_2$-$C_6$-alkenyl, $C_2$-$C_6$-alkynyl, $C_1$-$C_6$-alkyl aryl, $C_1$-$C_6$-alkyl heteroaryl, cycloalkyl, heterocycloalkyl, and Z is a counterion, including chloride, bromide, iodide, —O-alkyl, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

"Pharmaceutically active derivative" refers to any compound that upon administration to the recipient, is capable of providing directly or indirectly, the activity disclosed herein.

"Enantiomeric excess" (ee) refers to the products that are obtained by an asymmetric synthesis, i.e. a synthesis involving non-racemic starting materials and/or reagents or a synthesis comprising at least one enantioselective step, whereby a surplus of one enantiomer in the order of at least about 52% ee is yielded.

A first aspect of the invention consists in the use of pyridinyl acetonitriles of formula I in the preparation of a medicament for the prevention and/or treatment of an autoimmune disease, a neurodegenerative or neuronal disorder including epilepsy, Alzheimer's disease, Parkinson's disease, retinal diseases, spinal cord injury, head trauma, mood disorders, multiple sclerosis or amyotrophic lateral sclerosis, diabetes, obesity, asthma, septic shock, transplant rejection, cerebrovascular accident, glaucoma, a cardiovascular disease including stroke, arteriosclerosis, myocardial infarction, myocardial reperfusion injury, ischemia or an ischemic condition including heart, renal, kidney and brain reperfusion injuries, renal failure and inflammatory diseases including arteriosclerosis, arthritis, Inflammatory Bowel Disease or rheumatoid arthritis:

X is a substituted or unsubstituted pyridinyl.

G is an unsubstituted or substituted pyrimidinyl or triazinyl.

Formula (I) also comprises its tautomers, its geometrical isomers, its optically active forms as enantiomers, diastereomers and its racemate forms, as well as pharmaceutically acceptable salts thereof. Preferred pharmaceutically acceptable salts of the formula (I) are acid addition salts formed with pharmaceutically acceptable acids like hydrochloride, hydrobromide, sulfate or bisulfate, phosphate or hydrogen phosphate, acetate, benzoate, succinate, fumarate, maleate, lactate, citrate, tartrate, gluconate, methanesulfonate, benzenesulfonate, and para-toluenesulfonate salts.

One embodiment of the present invention consists in ortho-pyridinyl acetonitriles of formula (Ia) in its tautomeric forms, e.g. the below ones:

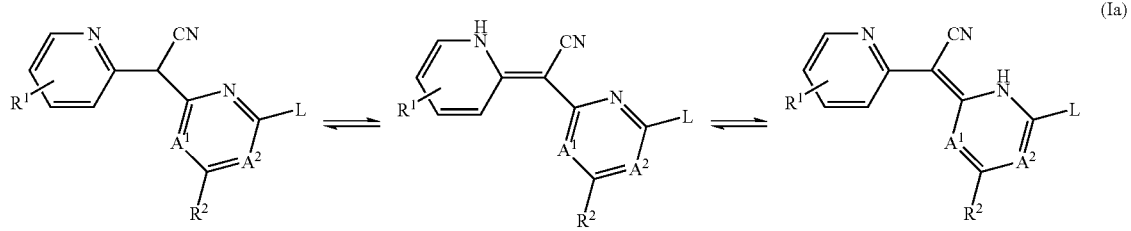

$A^1$ and $A^2$ are independently from each other selected from N and CH.

L is selected from the group comprising or consisting of sulfonyl, amino, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted aryl, unsubstituted or substituted heteroaryl, unsubstituted or substituted saturated or unsaturated 3-8-membered cycloalkyl, unsubstituted or substituted 3-8-membered heterocycloalkyl, (wherein said cycloalkyl, heterocycloalkyl, aryl or heteroaryl groups may be fused with 1-2 further cycloalkyl, heterocycloalkyl, aryl or heteroaryl group), an acyl moiety, unsubstituted or substituted $C_1$-$C_6$-alkyl aryl, unsubstituted or substituted $C_1$-$C_6$-alkyl heteroaryl, unsubstituted or substituted $C_2$-$C_6$-alkenyl aryl, unsubstituted or substituted $C_2$-$C_6$-alkenyl heteroaryl, unsubstituted or substituted $C_2$-$C_6$-alkynyl aryl, unsubstituted or substituted $C_2$-$C_6$-alkynyl heteroaryl, unsubstituted or substituted $C_1$-$C_6$-alkyl cycloalkyl, unsubstituted or substituted $C_1$-$C_6$-alkyl heterocycloalkyl, unsubstituted or substituted $C_2$-$C_6$-alkenyl cycloalkyl, unsubstituted or substituted $C_2$-$C_6$-alkenyl heterocycloalkyl, unsubstituted or substituted $C_1$-$C_6$-alkynyl cycloalkyl, unsubstituted or substituted $C_1$-$C_6$-alkynyl heterocycloalkyl, substituted or unsubstituted alkoxycarbonyl, substituted or unsubstituted aminocarbonyl, substituted or unsubstituted $C_1$-$C_6$-alkyl carboxy, substituted or unsubstituted $C_1$-$C_6$-alkyl acyl, substituted or unsubstituted aryl acyl, substituted or unsubstituted heteroaryl acyl, substituted or unsubstituted $C_3$-$C_8$-(hetero)cycloalkyl acyl, unsubstituted or substituted $C_1$-$C_6$-alkyl acyloxy, unsubstituted or substituted $C_1$-$C_6$-alkyl alkoxy, unsubstituted or substituted $C_1$-$C_6$-alkyl alkoxycarbonyl, unsubstituted or substituted $C_1$-$C_6$-alkyl aminocarbonyl, unsubstituted or substituted $C_1$-$C_6$-alkyl acylamino, acylamino, unsubstituted or substituted $C_1$-$C_6$-alkyl ureido, substituted or unsubstituted $C_1$-$C_6$-alkyl carbamate, unsubstituted or substituted $C_1$-$C_6$-alkyl amino, unsubstituted or substituted $C_1$-$C_6$-alkyl ammonium, unsubstituted or substituted $C_1$-$C_6$-alkyl sulfonyloxy, unsubstituted or substituted $C_1$-$C_6$-alkyl sulfonyl, unsubstituted or substituted $C_1$-$C_6$-alkyl sulfinyl, unsubstituted or substituted $C_1$-$C_6$-alkyl sulfanyl, unsubstituted or substituted $C_1$-$C_6$-alkyl sulfonylamino, unsubstituted or substituted $C_1$-$C_6$-alkyl aminosulfonyl, hydroxy, halogen, cyano.

$R^1$ is selected from the group comprising or consisting of hydrogen, sulfonyl, amino, unsubstituted or substituted $C_1$-$C_6$-alkyl, unsubstituted or substituted $C_2$-$C_6$-alkenyl, unsubstituted or substituted $C_2$-$C_6$-alkynyl or $C_1$-$C_6$-alkoxy, unsubstituted or substituted aryl (e.g. phenyl), halogen, cyano or hydroxy. Preferably $R^1$ is H or $C_1$-$C_3$ alkyl (e.g. a methyl or ethyl group).

$R^2$ is selected from the group comprising or consisting of hydrogen, sulfonyl, amino, unsubstituted or substituted $C_1$-$C_6$-alkyl, unsubstituted or substituted $C_2$-$C_6$-alkenyl, unsubstituted or substituted $C_2$-$C_6$-alkynyl or $C_1$-$C_6$-alkoxy, halogen, cyano or hydroxy. Preferably $R^2$ is H or $C_1$-$C_3$ alkyl (e.g. a methyl group).

A further embodiment of the present invention consists in ortho-pyridinyl acetonitriles of formula (Ib) in its tautomeric forms, e.g. the below ones:

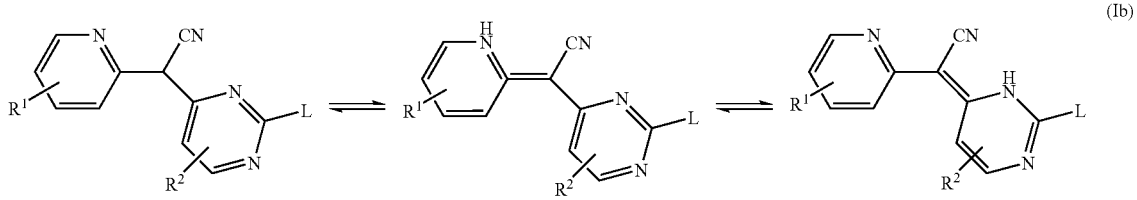

(Ib)

$R^1$, $R^2$ and L are as defined for formula (Ia).

Still a further embodiment of the present invention consists in ortho-pyridinyl acetonitriles of formula (Ic) in its tautomeric forms, e.g. the below ones:

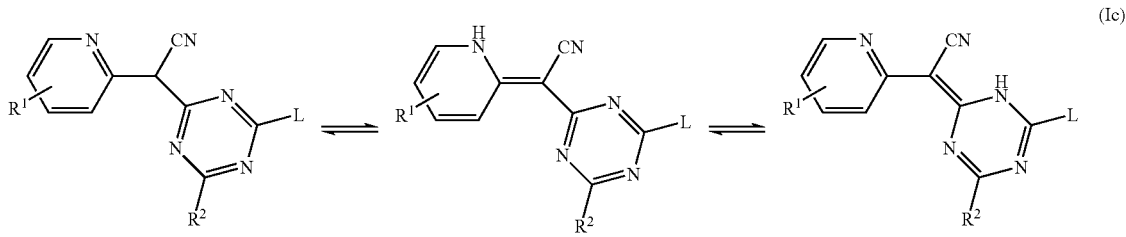

(Ic)

R¹, R² and L are as defined for formula (Ia).

According to a further embodiment the moiety L within formulae (Ia), (Ib) & (Ic) is selected from the group consisting of a $C_1$-$C_6$-alkoxy or an amino group of the formula —NR³R⁴ wherein R³ and R⁴ are each independently from each other H, unsubstituted or substituted $C_1$-$C_6$-alkyl, unsubstituted or substituted $C_2$-$C_6$-alkenyl, unsubstituted or substituted $C_2$-$C_6$-alkynyl, unsubstituted or substituted $C_1$-$C_6$-alkoxy, unsubstituted or substituted aryl, unsubstituted or substituted heteroaryl, unsubstituted or substituted saturated or unsaturated 3-8-membered cycloalkyl, unsubstituted or substituted 3-8-membered heterocycloalkyl, (wherein said cycloalkyl, heterocycloalkyl, aryl or heteroaryl groups may be fused with 1-2 further cycloalkyl, heterocycloalkyl, aryl or heteroaryl group), an acyl moiety, unsubstituted or substituted $C_1$-$C_6$-alkyl aryl, unsubstituted or substituted $C_1$-$C_6$-alkyl heteroaryl, unsubstituted or substituted $C_2$-$C_6$-alkenyl aryl, unsubstituted or substituted $C_2$-$C_6$-alkenyl heteroaryl, unsubstituted or substituted $C_2$-$C_6$-alkynyl aryl, unsubstituted or substituted $C_2$-$C_6$-alkynyl heteroaryl, unsubstituted or substituted $C_1$-$C_6$-alkyl cycloalkyl, unsubstituted or substituted $C_1$-$C_6$-alkyl heterocycloalkyl, unsubstituted or substituted $C_2$-$C_6$-alkenyl cycloalkyl, unsubstituted or substituted $C_2$-$C_6$-alkenyl heterocycloalkyl, unsubstituted or substituted $C_2$-$C_6$-alkynyl cycloalkyl, unsubstituted or substituted $C_2$-$C_6$-alkynyl heterocycloalkyl. Alternatively, R³ and R⁴ may form a ring together with the nitrogen to which they are bound.

In a specific embodiment R³ is hydrogen and R⁴ is an unsubstituted or substituted $C_1$-$C_6$-alkyl, substituted saturated or unsaturated 3-8-membered cycloalkyl.

In a preferred embodiment R³ is H and R⁴ is selected from the group consisting of straight or branched $C_1$-$C_6$ alkyl, 3-8 membered cycloalkyl, 3-8 membered heterocycloalkyl, aryl, heteroaryl, $C_1$-$C_6$-alkyl aryl, $C_1$-$C_6$-alkyl heteroaryl, $C_1$-$C_6$-alkyl cycloalkyl, $C_1$-$C_6$-alkyl heterocycloalkyl. Examples of cycloalkyl are cyclopropyl, cyclopentyl or cyclohexyl.

In a further specific embodiment R¹ is either a bromine or an amine of the formula —NHR⁴ whereby R⁴ is $C_1$-$C_6$-alkyl, aryl, heteroaryl, saturated or unsaturated 3-8-membered cycloalkyl, 3-8-membered heterocycloalkyl, $C_1$-$C_6$-alkyl aryl, $C_1$-$C_6$-alkyl heteroaryl, $C_1$-$C_6$-alkyl cycloalkyl, $C_1$-$C_6$-alkyl heterocycloalkyl.

Specific pyridinyl acetonitriles according to formula (I) are:

4-pyrimidineacetonitrile, 2-[[1-(diphenylmethyl)-3-azetidinyl]amino]-5-methyl-alpha-2(1H)-pyridinylidene- 4-pyrimidineacetonitrile, 5-methyl-2-[[2-(3-pyridinyl)ethyl]amino]-alpha-2(1H)-pyridinylidene- 4-pyrimidineacetonitrile, 2-[[2-[6-(dimethylamino)-3-pyridinyl]ethyl]amino]-5-methyl-alpha-2(1H)-pyridinylidene- 4-pyrimidineacetonitrile, 5-methyl-2-[[3-(2-oxo-1-pyrrolidinyl)propyl]amino]-alpha-2(1H)-pyridinylidene- 4-pyrimidineacetonitrile, 5-methyl-alpha-2-pyridinyl-2-[[2-(2-pyridinyl)ethyl]amino]-

4-pyrimidineacetonitrile, 2-(cyclopentylamino)-5-methyl-alpha-(6-phenyl-2(1H)-pyridinylidene)-

4-pyrimidineacetonitrile, 2-chloro-5-methyl-alpha-(6-phenyl-2(1H)-pyridinylidene)-

4-pyrimidineacetonitrile, 5-methyl-2-(4-piperidinylamino)-alpha-2(1H)-pyridinylidene- 4-pyrimidineacetonitrile, 2-(cyclohexylamino)-5-methyl-alpha-2-pyridinyl- 4-pyrimidineacetonitrile, 2-[(cyclohexylmethyl)amino]-5-methyl-alpha-2-pyridinyl- 4-pyrimidineacetonitrile, 2-(cyclopentylamino)-5-methyl-alpha-2-pyridinyl- 4-pyrimidineacetonitrile, 2-[(3-hydroxy-1-phenylpropyl)amino]-5-methyl-alpha-2(1H)-pyridinylidene- 4-pyrimidineacetonitrile, 2-(cyclobutylamino)-5-methyl-alpha-2(1H)-pyridinylidene- 4-pyrimidineacetonitrile, 2-(cyclopentylamino)-alpha-(1-ethyl-2(1H)-pyridinylidene)-5-methyl- 4-pyrimidineacetonitrile, 2-(cyclopropylamino)-5-methyl-alpha-2-pyridinyl- 4-pyrimidineacetonitrile, 5-methyl-2-[[1-(phenylmethyl)-4-piperidinyl]amino]-alpha-2(1H)-pyridinylidene- 4-pyrimidineacetonitrile, 2-[(1-ethylpropyl)amino]-5-methyl-alpha-2(1H)-pyridinylidene- 4-pyrimidineacetonitrile, 5-methyl-alpha-2(1H)-pyridinylidene-2-[[(tetrahydro-2H-pyran-4-yl)methyl]amino]-

4-pyrimidineacetonitrile, 5-methyl-alpha-2(1H)-pyridinylidene-2-[[(tetrahydro-2-furanyl)methyl]amino]-

4-pyrimidineacetonitrile, 5-methyl-2-[(2-methylpropyl)amino]-alpha-2(1H)-pyridinylidene- 4-pyrimidineacetonitrile, 5-methyl-2-[(1-methylethyl)amino]-alpha-2(1H)-pyridinylidene- 4-pyrimidineacetonitrile, 2-[[(1S,2S)-2-hydroxycyclohexyl]amino]-5-methyl-alpha-2(1H)-pyridinylidene- 4-pyrimidineacetonitrile, 2-[[(1S,2S)-2-hydroxycyclopentyl]amino]-5-methyl-alpha-2(1H)-pyridinylidene- 4-pyrimidineacetonitrile, 2-[(trans-4-hydroxycyclohexyl)amino]-5-methyl-alpha-2(1H)-pyridinylidene- 1-piperidinecarboxylic acid, 4-[[4-[(E)-cyano-2(1H)-pyridinylidenemethyl]-5-methyl-2-pyrimidinyl]amino]-, 1,1-dimethylethyl ester 4-pyrimidineacetonitrile, 2-chloro-5-methyl-alpha-2(1H)-pyridinylidene- 4-pyrimidineacetonitrile, 5-methyl-2-[(1-methylbutyl)amino]-alpha-2-pyridinyl- 4-pyrimidineacetonitrile, 2-(cyclopentylamino)-alpha-2-pyridinyl- 4-pyrimidineacetonitrile, 2-(cyclohexylamino)-alpha-2-pyridinyl- 4-pyrimidineacetonitrile, 5-methyl-alpha-2-pyridinyl-2-[4-(2-pyrimidinylamino)-1-piperidinyl]-

4-pyrimidineacetonitrile, alpha-2-pyridinyl-2-[[2-(3-pyridinyl)ethyl]amino]-

4-pyrimidineacetonitrile, 2-(cyclopropylamino)-alpha-2-pyridinyl-benzoic acid, 4-[2-[[4-(cyano-2-pyridinylmethyl)-5-methyl-2-pyrimidinyl]amino]ethyl]-, methyl ester 4-pyrimidineacetonitrile, 2-[(1,2-dimethylpropyl)amino]-5-methyl-alpha-2-pyridinyl- 4-pyrimidineacetonitrile, 2-[(2,3-dimethylcyclohexyl)amino]-5-methyl-alpha-2-pyridinyl- 4-pyrimidineacetonitrile, alpha-4-pyridinyl-2-[[2-(3-pyridinyl)ethyl]amino]-

4-pyrimidineacetonitrile, 2-[(2-furanylmethyl)amino]-5-methyl-alpha-2-pyridinyl- 4-pyrimidineacetonitrile, 2-[(1-methylbutyl)amino]-alpha-2-pyridinyl- 4-pyrimidineacetonitrile, 5-methyl-2-[[2-(1H-pyrazol-1-yl)ethyl]amino]-alpha-2-pyridinyl- 4-pyrimidineacetonitrile, 2-[[2-(4-aminophenyl)ethyl]amino]-5-methyl-alpha-2-pyridinyl- 4-pyrimidineacetonitrile, 2-[[(4-methoxyphenyl)methyl]amino]-5-methyl-alpha-2-pyridinyl- 4-pyrimidineacetonitrile, 6-(cyclopentylamino)-alpha-2-pyridinyl- 4-pyrimidineacetonitrile, alpha-2-pyridinyl-2-[[2-(2-pyridinyl)ethyl]amino]-

4-pyrimidineacetonitrile, 2-(4-ethyl-1-piperazinyl)-6-methyl-alpha-2-pyridinyl-
4-pyrimidineacetonitrile, 2-(cyclopentylamino)-alpha-4-pyridinyl-
4-pyrimidineacetonitrile, 2-[[[4-(difluoromethoxy)phenyl]methyl]amino]-alpha-2-pyridinyl-
4-pyrimidineacetonitrile, 2-[(2,3-dimethylcyclohexyl)amino]-alpha-2-pyridinyl-
4-pyrimidineacetonitrile, 6-methyl-2-[(1-methylbutyl)amino]-alpha-2-pyridinyl-
4-pyrimidineacetonitrile, 2-[(2-furanylmethyl)amino]-alpha-2-pyridinyl-
4-pyrimidineacetonitrile, 2-(cyclopentylamino)-6-methyl-alpha-2-pyridinyl-
1,3,5-triazine-2-acetonitrile, 4-(methylamino)-alpha-2-pyridinyl-6-[[2-(3-pyridinyl)ethyl]amino]-
4-pyrimidineacetonitrile, 2-[[2-[6-(dimethylamino)-3-pyridinyl]ethyl]amino]-alpha-2-pyridinyl-
4-pyrimidineacetonitrile, 2-chloro-alpha-3-pyridinyl-
4-pyrimidineacetonitrile, 2-(dipropylamino)-5-methyl-alpha-2-pyridinyl-
4-pyrimidineacetonitrile, alpha-2-pyridinyl-6-[[2-(3-pyridinyl)ethyl]amino]-
4-pyrimidineacetonitrile, alpha-(3-bromo-2(1H)-pyridinylidene)-2-(cyclopentylamino)-
4-pyrimidineacetonitrile, alpha-(6-bromo-2(1H)-pyridinylidene)-5-methyl-2-[[3-(1H-pyrazol-1-yl)propyl]amino]-
4-pyrimidineacetonitrile, alpha-(6-bromo-2(1H)-pyridinylidene)-5-methyl-2-[[3-(2-oxo-1-pyrrolidinyl)propyl]amino]-
4-pyrimidineacetonitrile, alpha-(6-bromo-2(1H)-pyridinylidene)-2-(cyclopentylamino)-5-methyl-
4-pyrimidineacetonitrile, alpha-(6-bromo-2(1H)-pyridinylidene)-2-(cyclopentylamino)-
4-pyrimidineacetonitrile, alpha-(6-bromo-2(1H)-pyridinylidene)-5-methyl-2-[[3-(3-oxo-4-morpholinyl)propyl]amino]-
4-pyrimidineacetonitrile, 2-(cyclopentylamino)-alpha-[6-(cyclopropylamino)-2(1H)-pyridinylidene]-5-methyl-
4-pyrimidineacetonitrile, alpha-(6-bromo-2(1H)-pyridinylidene)-5-methyl-2-[[3-(1H-1,2,4-triazol-1-yl)propyl]amino]-
4-pyrimidineacetonitrile, alpha-(3-bromo-2(1H)-pyridinylidene)-2-[[3-(2-oxo-1-pyrrolidinyl)propyl]amino]-
4-pyrimidineacetonitrile, 2-(cyclopentylamino)-5-methyl-alpha-[6-(phenylamino)-2(1H)-pyridinylidene]-
4-pyrimidineacetonitrile, 5-methyl-2-[[3-(1H-pyrazol-1-yl)propyl]amino]-alpha-2(1H)-pyridinylidene-
4-pyrimidineacetonitrile, alpha-(6-bromo-2(1H)-pyridinylidene)-2-[[3-(1H-1,2,4-triazol-1-yl)propyl]amino]-
4-pyrimidineacetonitrile, 5-methyl-2-[[3-(3-oxo-4-morpholinyl)propyl]amino]-alpha-2(1H)-pyridinylidene-
4-pyrimidineacetonitrile, 2-(cycloheptylamino)-5-methyl-alpha-2(1H)-pyridinylidene-
4-pyrimidineacetonitrile, alpha-(6-bromo-2(1H)-pyridinylidene)-2-[[2-(1H-1,2,4-triazol-1-yl)ethyl]amino]-
4-pyrimidineacetonitrile, 5-methyl-alpha-2(1H)-pyridinylidene-2-[[3-(1H-1,2,4-triazol-1-yl)propyl]amino]-
4-pyrimidineacetonitrile, alpha-(5-bromo-2(1H)-pyridinylidene)-2-(cyclopentylamino)-
4-pyrimidineacetonitrile, 2-[[3-(1H-pyrazol-1-yl)propyl]amino]-alpha-[6-[[3-(1H-pyrazol-1-yl)propyl]amino]-2(1H)-pyridinylidene]-
4-pyrimidineacetonitrile, 2-(cycloheptylamino)-alpha-2(1H)-pyridinylidene-
4-pyrimidineacetonitrile, alpha-(6-bromo-2(1H)-pyridinylidene)-5-methyl-2-[[2-(1H-1,2,4-triazol-1-yl)ethyl]amino]-
4-pyrimidineacetonitrile, 2-(cyclopentylamino)-5-methyl-alpha-[6-(4-morpholinyl)-2(1H)-pyridinylidene]-
4-pyrimidineacetonitrile, 2-[[(1S,2S)-2-hydroxycyclopentyl]amino]-alpha-2(1H)-pyridinylidene-
4-pyrimidineacetonitrile, alpha-(3-bromo-2(1H)-pyridinylidene)-2-(cyclopentylamino)-5-methyl-
4-pyrimidineacetonitrile, 2-[[3-(2-oxo-1-pyrrolidinyl)propyl]amino]-alpha-2(1H)-pyridinylidene-
4-pyrimidineacetonitrile, 2-[[2-(1H-imidazol-4-yl)ethyl]amino]-5-methyl-alpha-2(1H)-pyridinylidene-
4-pyrimidineacetonitrile, 2-[[(1S,2S)-2-hydroxycyclohexyl]amino]-5-methyl-alpha-2(1H)-pyridinylidene-
4-pyrimidineacetonitrile, 2-(cyclopentylamino)-5-methyl-alpha-[6-[[2-(3-pyridinyl)ethyl]amino]-2(1H)-pyridinylidene]-
4-pyrimidineacetonitrile, 2-(cyclopentylamino)-5-methyl-alpha-[6-[[3-(2-oxo-1-pyrrolidinyl)propyl]amino]-2(1H)-pyridinylidene]-
4-pyrimidineacetonitrile, 2-(cyclopentylamino)-5-methyl-alpha-[6-[methyl(phenylmethyl)amino]-2(1H)-pyridinylidene]-
4-pyrimidineacetonitrile, alpha-(3-bromo-2(1H)-pyridinylidene)-5-methyl-2-[[3-(3-oxo-4-morpholinyl)propyl]amino]-
4-pyrimidineacetonitrile, 2-[[(1S,2S)-2-(phenylmethoxy)cyclopentyl]amino]-alpha-2(1H)-pyridinylidene-
4-pyrimidineacetonitrile, 2-(cyclopentylamino)-alpha-[6-(2-pyridinylamino)-2(1H)-pyridinylidene]-
4-pyrimidineacetonitrile, alpha-(3-bromo-2(1H)-pyridinylidene)-5-methyl-2-[[3-(2-oxo-1-pyrrolidinyl)propyl]amino]-
4-pyrimidineacetonitrile, 2-(cyclopentylamino)-5-methyl-alpha-[6-[(trimethylsilyl)ethynyl]-2(1H)-pyridinylidene]-
4-pyrimidineacetonitrile, 2-(cyclopentylamino)-alpha-[6-(3-pyridinylamino)-2(1H)-pyridinylidene]-
4-pyrimidineacetonitrile, 2-(cyclopentylamino)-alpha-[6-(cyclopentylamino)-2(1H)-pyridinylidene]-5-methyl-
4-pyrimidineacetonitrile, alpha-[3-(3-hydroxy-3-methyl-1-butynyl)-2(1H)-pyridinylidene]-5-methyl-2-[[3-(3-oxo-4-morpholinyl)propyl]amino]-
4-pyrimidineacetonitrile, alpha-(3-bromo-2(1H)-pyridinylidene)-5-methyl-2-[[3-(1H-1,2,4-triazol-1-yl)propyl]amino]
4-pyrimidineacetonitrile, alpha-(3-bromo-2(1H)-pyridinylidene)-2-chloro-5-methyl-
4-pyrimidineacetonitrile, alpha-(6-bromo-2(1H)-pyridinylidene)-2-chloro-5-methyl- Compounds of formula (I) are suitable for the use as medicament, in particular for the treatment and/or prevention of autoimmune disorders, neuro-degenerative diseases, neuronal disorders including epilepsy, Alzheimer's disease, Parkinson's disease, retinal diseases, spinal cord injury, head trauma, mood disorders, particularly bipolar mood disorders, multiple sclerosis or amyotrophic lateral sclerosis, diabetes, particularly type II diabetes and obesity, asthma, septic shock, transplant rejection, cerebrovascular accident, glaucoma, cardiovascular diseases including stroke, arteriosclerosis, myocardial infarction, myocardial reperfusion injury, ischemia, cancer and inflammatory diseases including arteriosclerosis, arthritis, Inflammatory Bowel Disease or rheumatoid arthritis.

A further aspect of the present invention is related to the use of the pyridinyl acetonitriles according to formula (I) for the preparation of pharmaceutical compositions for the modulation—notably of the inhibition—of a protein kinase mediated signalling pathways as well as for preventive and therapeutic treatment of diseases caused by abnormal protein kinase activity. Preferably, this protein kinase is a c-Jun Kinase or Glycogen Synthase Kinase 3, particularly Glycogen Synthase Kinase 3 beta. The compounds according to formula I could be employed alone or in combination with further pharmaceutical agents.

Specifically, the compounds of formula (I) are useful in the preparation of a medicament for the prevention and/or treatment of pathological states and diseases in which inhibition of protein kinases, particularly of JNK or Glycogen Synthase Kinase 3 is required. These diseases are selected in the group consisting of neurodegenerative diseases, neuronal disorders including epilepsy, Alzheimer's disease, Parkinson's disease, retinal diseases, spinal cord injury, head trauma, multiple sclerosis or amyotrophic lateral sclerosis, diabetes, particularly type II diabetes and obesity, asthma, septic shock, transplant rejection, cerebrovascular accident, glaucoma, cardiovascular diseases including stroke, arteriosclerosis, myocardial infarction, myocardial reperfusion injury, ischemia and inflammatory diseases including arteriosclerosis, arthritis, Inflammatory Bowel Disease or rheumatoid arthritis.

Specifically, the compounds of formula I are suitable for use in treating disorders of the immune system and neuronal system of mammals, notably of human beings. Such neuronal system disorders include for example neurodegenerative diseases e.g. Alzheimer's disease, Huntington's disease, Parkinson's disease, retinal diseases, spinal cord injury, multiple sclerosis or amyotrophic lateral sclerosis, head trauma, epilepsy and seizures, ischemic and hemorrhagic brain strokes.

Also, the compounds of formula I are suitable for use in the treatment and/or prevention of metabolic disorders mediated by insulin resistance or hyperglycemia, comprising diabetes type I and/or II, inadequate glucose tolerance, insulin resistance, hyperlipidemia, hypertriglyceridemia, hypercholesterolemia, obesity, polycystic ovary syndrome (PCOS).

Immune system disorders include for example asthma, transplant rejection, inflammatory processes such as inflammatory bowel disease (IBD), cartilage and bone erosion disorders, rheumatoid arthritis, septic shock.

The compounds according to formulae Ia-Ic are also suitable for use in treating cancers, such as breast, colorectal, pancreatic, prostate, testicular, ovarian, lung, liver and kidney cancers.

In another embodiment, the compounds according to formulae I may be used for treating cardiovascular diseases including arteriosclerosis, restenosis, glaucoma, stroke, ischemia, e.g. cerebral ischemia, myocardial reperfusion injury or myocardial infarction.

In another embodiment, the compounds according to formula I may be used for treating various ischemic conditions including heart and kidney failures, hepatic disorders and brain reperfusion injuries.

Another object of the present invention is a method for the treatment of disease states mediated by a protein kinase comprising the administration to the patient of a pharmaceutically active amount of a pyridinyl acetonitrile according to formula (I).

Still a further object of the present invention is a process for preparing the pyridinyl acetonitriles according to formula I.

The pyridinyl acetonitriles exemplified in this invention may be prepared from readily available starting materials using the following general methods and procedures. It will be appreciated that where typical or preferred experimental conditions (i.e., reaction temperatures, time, moles of reagents, solvents, etc.) are given, other experimental conditions can also be used unless otherwise stated. Optimum reaction conditions may vary with the particular reactants or solvents used, but such conditions can be determined by one skilled in the art by routine optimisation procedures.

Generally, the pyridinyl acetonitriles derivatives according to the general formula I may be obtained by several processes using solution-phase chemistry protocols.

According to one process, pyridinyl acetonitriles derivatives according to the general formula I, whereby the substituents X and G are as above defined, are prepared from the corresponding acetonitrile derivatives I and chloro derivatives V, by well known solution-phase chemistry protocols, such as those described in the Examples and shown in Scheme 1, below.

Scheme 1

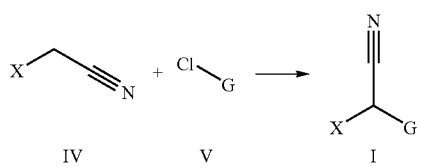

The chloro derivatives V can be obtained either through commercial sources or made up from various chemistry protocols such as shown in the scheme 2, below.

The pyridinyl acetonitriles of general formula I are prepared according to a general process outlined above, and also starting from the pyridinyl acetonitriles derivatives IV, whereby X is as above defined, which was reacted with the bis-chloro derivatives V', where G' is as above defined, to give the intermediate of synthesis II'. In a subsequent step, the intermediate II' was treated with the amines III, whereby the substituents $R^3$, $R^4$ are as above defined to give the final pyridinyl acetonitrile derivatives I, utilizing well known solution-phase chemistry protocols, such as those described in the Examples and shown in Scheme 2, below Scheme 2

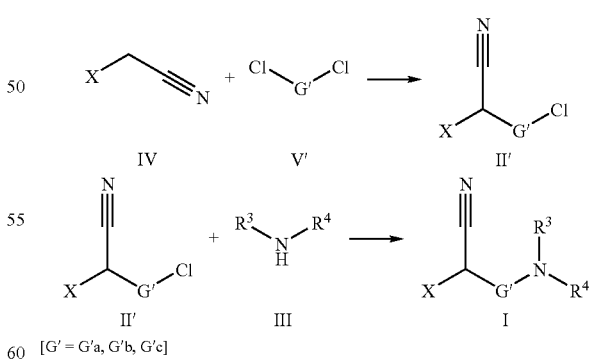

[G' = G'a, G'b, G'c]

and whereby G' is either a pyrimidinyl or triazinyl core G'a. G'b or G'c as shown in the Scheme 3 below, and whereby $R^2$ is as above defined and also $A^1$ and $A^2$ are independently from each other selected from N and CH.

Scheme 3

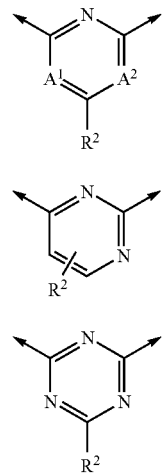

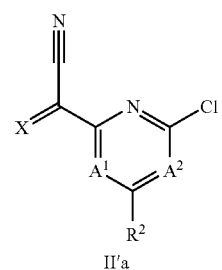

II'a

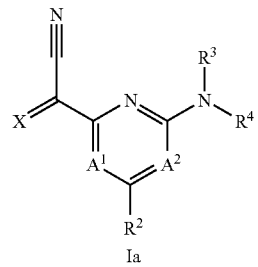

II'a    III

The pyridinyl acetonitriles derivatives according to the general formula Ia, whereby the substituent X is as above defined, were obtained in two subsequent steps as shown in Scheme 4. In a first step, the chloro pyridinyl acetonitriles derivatives II'a were isolated after condensation of the pyridinyl compound IV with a bis-chloro derivative V'a, whereby the heteroaromatic core is G'a, and R² is as above defined and also A¹ and A² are independently from each other selected from N and CH. This first reaction step was performed using, e.g. lithium hydride or sodium hydride or similar reagents in an appropriate solvent such as THF or DMF. This reaction can be performed at various temperature depending of the intrinsic reactivity of compounds IV and V'a, by traditional thermic method or using microwave technology, using standard conditions well known to the person skilled in the art, such as those described hereinafter in the Examples. In a subsequent step, the chloro pyridinyl acetonitriles derivatives II'a were treated with various amines III to give the expected pyridinyl acetonitriles derivatives Ia. The nucleophilic displacement of the chloro atom of the heterocyclic moiety by the amine III, is accomplished by treatment with several equivalents of the amines III in presence or absence of sodium iodine as catalyst and a base such as triethylamine of diisopropylethylamine or similar reagents. This reaction can be performed at various temperature depending of the intrinsic reactivity of compounds III and II'a, by traditional thermic method or using microwave technology, using standard conditions well known to the person skilled in the art, such as those described hereinafter in the Examples.

Scheme 4

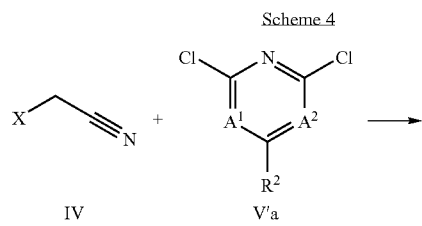

IV    V'a

Ia

The pyridinyl acetonitriles derivatives according to the general formula Ib, whereby the substituent X is as above defined, were obtained in two subsequent steps as shown in Scheme 5. In a first step, the chloro pyridinyl acetonitriles derivatives II'b were isolated after condensation of the pyridinyl compound IV with bis-chloro derivative V'b, whereby the heteroaromatic core is G'b, and R² is as above defined. This first reaction step was performed, using, e.g. lithium hydride or sodium hydride or similar reagents in an appropriate solvent such as THF or DMF. This reaction can be performed at various temperature depending of the intrinsic reactivity of compounds IV and V'b, by traditional thermic method or using microwave technology, using standard conditions well known to the person skilled in the art, such as those described hereinafter in the Examples. In a subsequent step, the chloro pyridinyl acetonitriles derivatives II'b were treated with various amines III to give the expected pyridinyl acetonitriles derivatives Ib. The nucleophilic displacement of the chloro atom of the pyrimidinyl moiety by the amine III, is accomplished by treatment with several equivalents of the amines III in presence or absence of sodium iodine as catalyst and a base such as triethylamine of diisopropylethylamine or similar reagents. This reaction can be performed at various temperatures depending of the intrinsic reactivity of compounds III and II'b, by traditional thermic method or using microwave technology, using standard conditions well known to the person skilled in the art, such as those described hereinafter in the Examples.

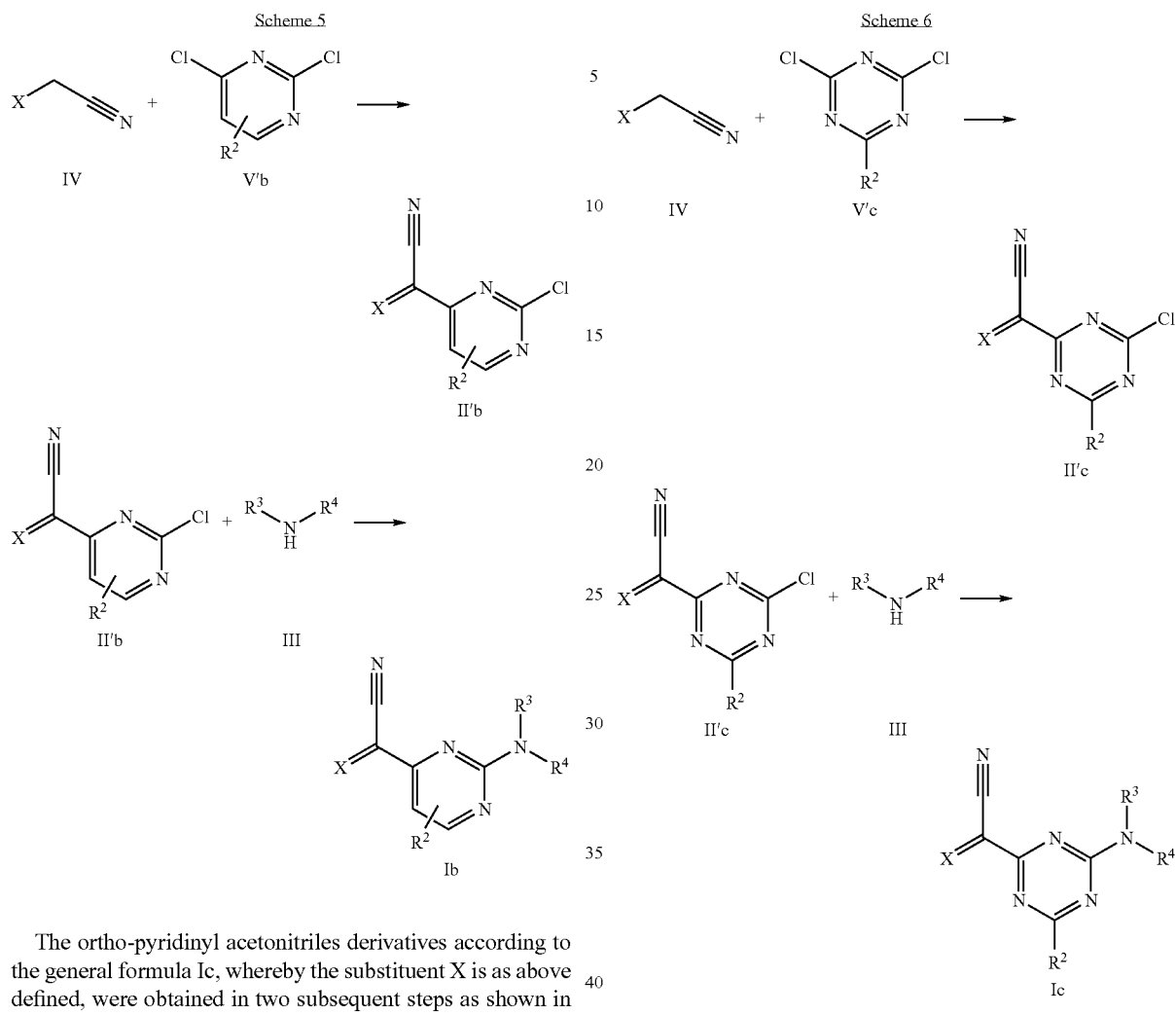

The ortho-pyridinyl acetonitriles derivatives according to the general formula Ic, whereby the substituent X is as above defined, were obtained in two subsequent steps as shown in Scheme 6. In a first step, the chloro triazinyl acetonitriles derivatives II'c were isolated after condensation of the pyridinyl compound IV with a bis-chloro derivative V'c, whereby the heteroaromatic core is G'c, and R² is as above defined. This first reaction step was performed, using, e.g. lithium hydride or sodium hydride or similar reagents in an appropriate solvent such as THF or DMF. This reaction can be performed at various temperature depending of the intrinsic reactivity of compounds IV and V'c, by traditional thermic method or using microwave technology, using standard conditions well known to the person skilled in the art, such as those described hereinafter in the Examples. In a subsequent step, the chloro pyridinyl acetonitriles derivatives II'c were treated with various amines III to give the expected pyridinyl acetonitriles derivatives Ic. The nucleophilic displacement of the chloro atom of the triazinyl moiety by the amine III, is accomplished by treatment with several equivalents of the amines III in presence or absence of sodium iodine as catalyst and a base such as triethylamine of diisopropylethylamine or similar reagents. This reaction can be performed at various temperature depending of the intrinsic reactivity of compounds III and II'c, by traditional thermic method or using microwave technology, using standard conditions well known to the person skilled in the art, such as those described hereinafter in the Examples.

The pyridinyl acetonitriles components IV are either obtained from commercial sources or made in two subsequent steps, from the corresponding methylpyridines derivatives VI, by treatment of the latter with N-bromosuccinimide and benzoyl peroxide allowing to obtain the bromo methylpyridine analogue VII, which was subsequently treated with sodium cyanide used to transform a bromomethyl compound into its corresponding pyridinyl acetonitriles IV, under standard conditions well known to the person skilled in the art, such as those described in the Examples and shown in Scheme 7 below.

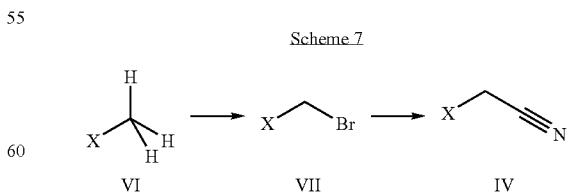

The dichloro heterocycles V'a and dichloropyrimidyl components V'b are obtained from commercial sources. The dichlorotriazinyl derivatives V'c are obtained from commercial sources or made from cyanuric chloride VIII, by treatment of the latter with primary or secondary amines III, using standard conditions well known to the practitioner skilled in the art, to yield products of formula V'c, as shown in scheme 8

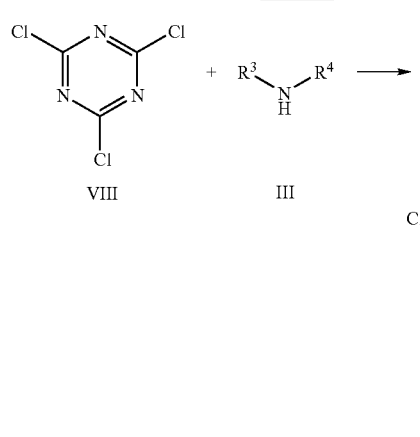

Scheme 8

The pyridinyl compounds of formula IV, the methylpyridine derivatives of formula VI or the bromopyridine derivatives VII presented in Schemes 1, 4, 5, 6, 7, in which X is as above defined, are either commercially available or may be obtained using, e.g., one of the processes exemplified in Scheme 9 and described hereinafter in the Examples. A particularly preferred process consists in the transformation of one functional moiety ($R^1$) into a different one ($R^{1'}$), using any known functional group interconversion protocols. As illustrated in Scheme 9, the choice of the best synthetic strategy will be governed by the nature of the functional groups to be interconverted, and the compatibility of the required reaction conditions with other functional groups present in the corresponding compounds, as will be well appreciated by the person skilled in the art. Amongst the most preferred starting materials IV, VI and VII, are those wherein $R^1$ is —Br, —Cl, —I, —OH, —$NH_2$, —$CH_2OH$, —CHO, —COOH, —$NO_2$, and/or —$CH_2COOH$, which are either obtained from commercial sources or made by one of the numerous processes described in the literature. From the intermediates (XXI, XXV, XXVII) derived thereof, in which R is as defined in Scheme 9, a wide range of derivatives, such as e.g. (XXII)-(XXXV), in which $R^9$, $R^{10}$, $R^{11}$, $R^7$, are as above defined, can be obtained by reaction sequences including oxidations, reductions, O- and N-alkylations, reductive alkylations and aminations, chain-elongations, Mitsunobu reactions, Acylation, debocylation, Wittig reactions, acylations, sulfonylations, Stille, Suzuki, Sonogashira and any other appropriate transformations leading to functional group interconversions, some of which being exemplified in Scheme 9. The synthetic examples cited in Scheme 9 are meant to illustrate the concept of functional group interconversion as applied to compounds of general structures (I), (VI), and (VII), wherein R, $R^1$ are as defined in the above description and in Scheme 9, and are not construed to be viewed as limiting the scope of said synthetic approach.

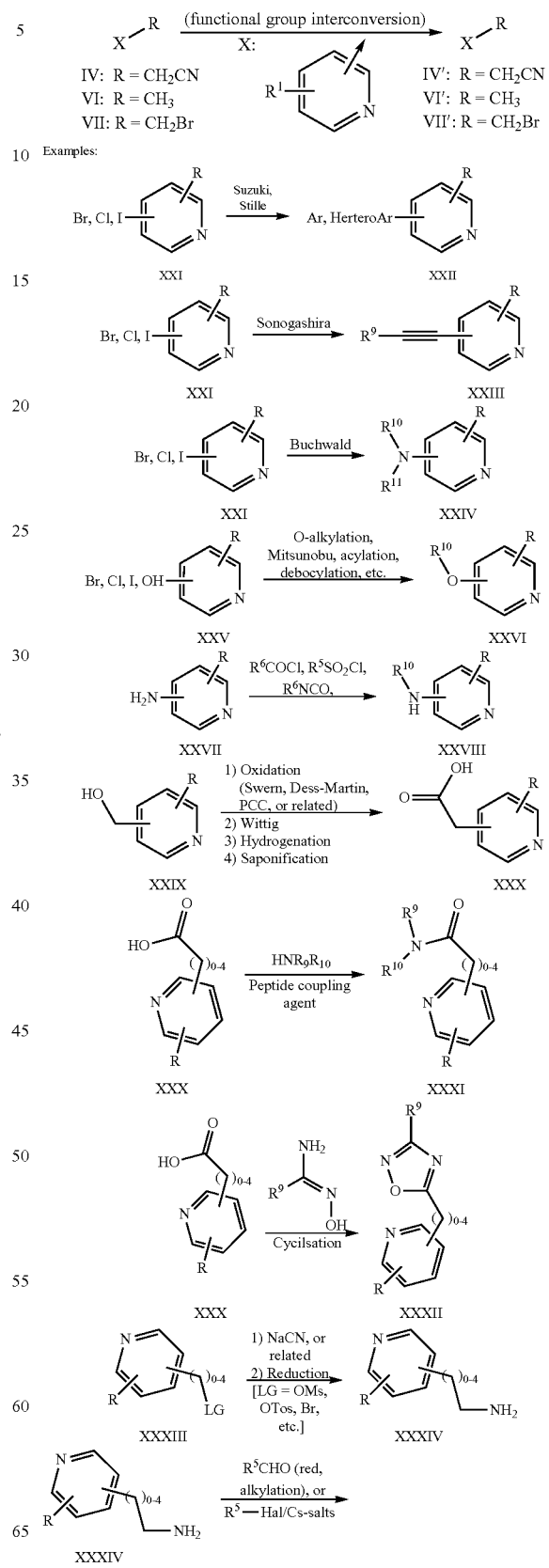

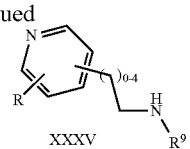

When employed as pharmaceuticals, the pyridinyl acetonitriles of the present invention are typically administered in the form of a pharmaceutical composition. Hence, pharmaceutical compositions comprising a compound of formula (I) and a pharmaceutically acceptable carrier, diluent or excipient therefore are also within the scope of the present invention. A person skilled in the art is aware of a whole variety of such carrier, diluent or excipient compounds suitable to formulate a pharmaceutical composition.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous use). Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed.

When employed as pharmaceuticals, pyridinyl acetonitriles of this invention are typically administered in the form of a pharmaceutical composition. Such compositions can be prepared in a manner well known in the pharmaceutical art and comprise at least one active compound. Generally, the compounds of this invention are administered in a pharmaceutically effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

The pharmaceutical compositions of these inventions can be administered by a variety of routes including oral, rectal, transdermal, subcutaneous, intravenous, intramuscular, intrathecal, intraperitoneal and intranasal. Depending on the intended route of delivery, the compounds are preferably formulated as either injectable, topical or oral compositions. The compositions for oral administration may take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampoules or syringes of the liquid compositions or pills, tablets, capsules or the like in the case of solid compositions. In such compositions, the pyridinyl acetonitrile compound is usually a minor component (from about 0.1 to about 50% by weight or preferably from about 1 to about 40% by weight) with the remainder being various vehicles or carriers and processing aids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As mentioned above, the pyridinyl acetonitriles of formula I in such compositions is typically a minor component, frequently ranging between 0.05 to 10% by weight with the remainder being the injectable carrier and the like.

The above described components for orally administered or injectable compositions are merely representative. Further materials as well as processing techniques and the like are set out in Part 5 of *Remington's Pharmaceutical Sciences*, 20$^{th}$ Edition, 2000, Marck Publishing Company, Easton, Pa., which is incorporated herein be reference.

The compounds of this invention can also be administered in sustained release forms or from sustained release drug delivery systems. A description of representative sustained release materials can also be found in the incorporated materials in *Remington's Pharmaceutical Sciences*.

In the following the present invention shall be illustrated by means of some examples which are not construed to be viewed as limiting the scope of the invention.

The following abbreviations are hereinafter used in the accompanying examples: min (minute), hr (hour), g (gram), mmol (millimole), m.p. (melting point), eq (equivalents), mL (milliliter), μL (microliters), mL (milliliters), ACN (Acetonitrile), Boc (butoxycarbonyl), CDCl$_3$ (deuterated chloroform), CsCO$_3$ (Cesium carbonate), cHex (Cyclohexanes), DCM (Dichloromethane), DIC (Diisopropyl carbodiimide), DIPEA (Diisopropylamine), DMA (Dimethylacetamide), DMAP (4-Dimethylaminopyridine) DMF (Dimethylformamide), DMSO (Dimethyl-sulfoxide), DMSO-d$_6$ (deuterated dimethylsulfoxide), EDC (1-(3-Dimethyl-amino-propyl)-3-ethylcarbodiimide), Et$_3$N (Triethylamine), EtOAc (Ethyl acetate), EtOH (Ethanol), Et$_2$O (Diethyl ether), Fmoc (9-fluorenyl-methoxycarbonyl), HOBt (1-Hydroxybenzotriazole), iPrOH (Isopropanol), K$_2$CO$_3$ (potassium carbonate), LiH (Lithium Hydride), NaI (Sodium Iodine), NaH (Sodium hydride), NaHCO$_3$ (Sodium bicarbonate), NH$_4$Cl (Ammonium chloride), nBuLi (n Butyllithium), Pd(PPh$_3$)$_4$ (Palladium triphenylphosphine tetrakis), (TBTU (O-Benzotriazolyl-N,N,N',N'-tetramethyluronium-tetrafluoroborate), TEA (Triethyl amine), TFA (Trifluoro-acetic acid), THF (Tetrahydrofuran), TMOF (trimethylorthoformate), MgSO₄ (Magnesium sulfate), PetEther (Petroleum ether), rt (room temperature).

The HPLC, NMR and MS data provided in the examples described below were obtained as followed: HPLC: column Waters Symmetry C8 50×4.6 mm, Conditions: MeCN/H₂O, 5 to 100% (8 min), max plot 230-400 nm; Mass spectra: PE-SCIEX API 150 EX (APCI and ESI), LC/MS spectra: Waters ZMD (ES); ¹H-NMR: Bruker DPX-300 MHz. The purifications were obtained as followed: Preparative HPLC Waters Prep LC 4000 System equipped with columns Prep Nova-Pak®HR C18 6 μm 60 Å, 40×30 mm (up to 100 mg) or 40×300 mm (up to 1 g). All the purifications were performed with a gradient of MeCN/H₂O 0.09% TFA.

EXAMPLES

Intermediate 1: 6-Bromo-2-bromomethylpyridine (cf. Scheme 7, compound VII)

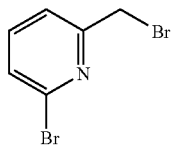

To a mixture of 6-bromo-2-methylpyridine (46.5 g, 0.27 mol) in CCl₄ (800 mL) was added NBS (53 g, 0.297 mol) and benzoylperoxide (4.7 g) and refluxed for 2 h in presence of light. The reaction mixture was cooled to 50° C. and filtered off the solid succinimide. The filtrate was concentrated and the crude 6-bromo-2-bromomethylpyridine (71 g) was used for next reaction.

1H NMR (300 MHz, CDCl3); 4.5 (s, 2H), 7.6 (d, J=7.8 Hz, 1H), 7.69 (d, J=7.8 Hz, 1, 1H), 7.84 (t, J=7.9 Hz). MS(ESI⁺): 251.9; MS(ESI⁻): 249.8

Intermediate 2: 6-Bromopyridin-2-yl-acetonitrile (cf. Scheme 7, compound IV)

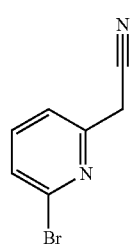

To a stirred solution of the above crude 6-bromo-2-bromomethylpyridine (70 g, 0.28 mol) in dioxane (500 mL) and water (250 mL), was added NaCN (28 g, 0.74 mol) at 0° C. and then stirred at RT for 16 h. The reaction mixture was quenched with 3 Lit of water and extracted with ethylacetate (4×500 mL). The organic layer was washed with water (400 L), brine (250 mL), dried over Na₂SO₄ and concentrated to give crude product. The crude was purified by column chromatography over silica gel (pet. ether/ethylacetate, 8:2) to give 6-bromopyridine-2-yl-acetonitrile (22.5 g, 40%). [TLC: Pet. ether/ethylacetate, 7:3, R𝑓=0.35]

1H NMR (300 MHz, CDCl3); 4.2 (s, 2H), 7.47 (d, J=7.9 Hz, 1H), 7.63 (d, J=7.9 Hz, 1, 1H), 7.8 (t, J=7.9 Hz). MS(ESI⁺): 199.2; MS(ESI⁻): 197.2.

Intermediate 3: 2-pyridineacetonitrile, 6-phenyl- (cf. Scheme 9, compound XXII)

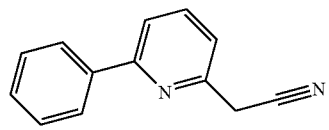

In a 25 mL flask, 12 mg of Pd(PPh₃)₄ (0.01 mmol, 0.02 eq), 100 mg of (6-bromopyrid-2-yl)acetonitrile (0.51 mmol, 1 eq) and 68 mg of phenyl boronic acid (0.56 mmol, 1.1 eq) were dissolved in 10 mL Benzene and 0.4 mL EtOH. Then 0.56 mL of a 2M solution Na₂CO₃ (1.12 mmol, 2.2 eq) were added. The reaction mixture was stirred under reflux for 40 h. The reaction was then quenched with brine, and extracted with EtOAc, then washed with water and brine. The organic layer was then dried over MgSO₄, filtered and concentrated carefully (benzene). The residue was purified by flash chromatography in cHex:EtOAc (80:20). The desired product was isolated as an orange solid (58 mg, Yield: 58%).

1H NMR (300 MHz, CDCl3); 4.11 (s, 2H), 7.41-7.53 (m, 4H), 7.73 (d, Jd=7.91, 1H), 7.88 (t, Jt=7.91, 1H), ), 8.02 (dd, Jd=7.91, Jd'=1.5, 2H). MS(ESI⁺): 195.33; MS(ESI⁻): 193.3.

Intermediate 4: 1,3,5-triazin-2-amine 4,6-dichloro-N-methyl- (cf. Scheme 8, compound V'c)

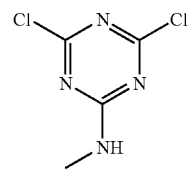

Cyanuric chloride (10 g, 54.3 mmol, 1 equiv.) was dissolved in THF (200 mL) and cooled to −70° C. Diisopropylethylamine (DIPEA) (36.3 mL, 1.42 mmol, 2 equiv.) and Methylamine hydrochloride (3.7 g, 1 equiv.) were added to the reaction mixture, which was stirred 2 h00 at −70° C. and 1 h at room temperature. The THF was removed in vacuo and the remaining material was taken up in DCM and washed with water. The organic layer was dried with MgSO₄ and the DCM removed to give a colourless powder (9.5 g, 97%)

MS(ESI⁺): 181.2; MS(ESI⁻): 179.2.

Intermediate 5: 4-pyrimidineacetonitrile, 2-chloro-5-methyl-alpha-2(1H)-pyridinylidene- (cf. Scheme 5, compound II'b)

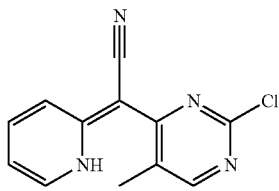

Method A:

To a suspension of LiH (404 mg, 50.79 mmol) in anhydrous THF (10 mL), was added dropwise a solution of 2-pyridylacetonitrile (3 g, 25.39 mmol) in anhydrous THF (10 mL). The reaction mixture was stirred at zero degree for 1 hour. A solution of 2,4-dichloro-5-methyl-pyrimidine (4.55 g, 27.93 mmol), dissolved in anhydrous THF (5 ml), was added dropwise at zero degree. The reaction mixture was stirred and heated to reflux for 14 hours. The reaction mixture was allowed to warm to r.t. and water was added (20 mL). THF was evaporated under vacuum and a solution of 1N HCl (20 mL) was added. The precipitate was filtered and washed with water (10 mL) and cyclohexanes (10 mL) to give a yellow solid which was dried under vacuum at 40 degrees. The yellow crystalline product 4-pyrimidineacetonitrile, 2-chloro-5-methyl-alpha-2(1H)-pyridinylidene was isolated. (5.5 g, 90%).

Method B:

To a suspension of NaH (1.3 g, of NaH in a 60% dispersion oil, 32.5 mmol, 4 eq) in anhydrous DMF (10 mL), was added dropwise at room temperature a solution of 2-pyridylacetonitrile (960 mg, 8.12 mmol, 1 eq) in anhydrous DMF (10 mL). The reaction mixture was stirred at room temperature for 1 hour. A solution of 2,4-dichloro-5-methyl-pyrimidine (1.32 g, 8.12 mmo, 1 eq), dissolved in anhydrous DMF (5 ml), was added dropwise at room temperature. The reaction mixture was stirred at room temperature for 14 hours. The mixture is hydrolysed with water (1 mL) and acidified with 1.6 mL of 10M HCl. The solvents were evaporated under vacuum. The residue was extracted with ethyl acetate. The organic layer was dried over MgSO4 and evaporated to dryness. The residue was purified by column chromatography with 50:50 (EtOAc:cHex). The fractions evaporated to give a yellow solid which was dried under vacuum at 40 degrees. The yellow crystalline product 4-pyrimidineacetonitrile, 2-chloro-5-methyl-alpha-2(1H)-pyridinylidene was isolated. (1.7 g, 86%).

4-pyrimidineacetonitrile, 2-chloro-5-methyl-alpha-2(1H)-pyridinylidene-: $^1$H NMR (300 MHz, DMSO); 2.34 (s, 3H), 3.31 (s, 1H), 6.94 (t, 1H), 7.41 (d, 1H), 7.84-7.97 (m, 2H), 8.25 (d, 1H), 15.19 (brs, 1 h). MS (ESI+) 245, (ESI−) 243.

Intermediate 6: 4-pyrimidineacetonitrile, 2-chloro-alpha-2(1H)-pyridinylidene- (cf. Scheme 5, compound II'b)

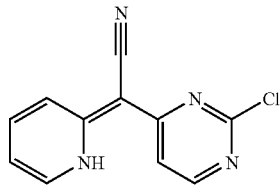

Following the general methods as outlined in Intermediate 5 (Method B), starting from 2-pyridylacetonitrile and 2,4-dichloro-pyrimidine, the title compound was isolated, after flash-chromatography, as a yellow solid in 61% yield (98.5% purity by HPLC).

MS(ESI$^+$): 231.2; MS(ESI$^-$): 229.8.

Intermediate 7: 4-pyrimidineacetonitrile, 2-chloro-5-methyl-alpha-3-pyridinyl- (cf. Scheme 5, compound II'b)

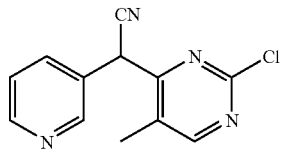

Following the general methods as outlined in Intermediate 5 (Method A), starting from 3-pyridylacetonitrile and 2,4-dichloro-5-methyl-pyrimidine, the title compound was isolated, after flash-chromatography, as a yellow solid in 82% yield (98% purity by HPLC).

MS(ESI$^+$): 246.2; MS(ESI$^-$): 244.6.

Intermediate 8: 4-pyrimidineacetonitrile, 2-chloro-alpha-3-pyridinyl- (cf. Scheme 5, compound II'b)

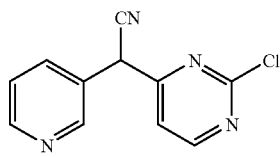

Following the general methods as outlined in Intermediate 5 (Method B), starting from 3-pyridylacetonitrile and 2,4-dichloro-pyrimidine, the title compound was isolated, after flash-chromatography, as a yellow solid in 55% yield (90% purity by HPLC).

MS(ESI$^+$): 231.3; MS(ESI$^-$): 229.4.

Intermediate 9: 4-pyrimidineacetonitrile, 2-chloro-5-methyl-alpha-4(1H)-pyridinylidene- (cf. Scheme 5, compound II'b)

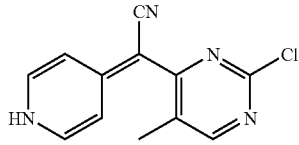

Following the general methods as outlined in Intermediate 5 (Method B), starting from 4-pyridylacetonitrile and 2,4-dichloro-5-methyl-pyrimidine, the title compound was isolated, after flash-chromatography, as a yellow solid in 72% yield (96% purity by HPLC).
MS(ESI$^+$): 245.7; MS(ESI$^-$): 243.5

Intermediate 10: 4-pyrimidineacetonitrile, 2-chloro-alpha-4(1H)-pyridinylidene- (cf. Scheme 5, compound II'b)

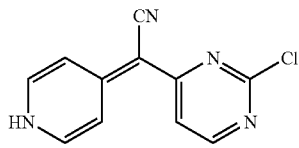

Following the general methods as outlined in Intermediate 5 (Method B), starting from 4-pyridylacetonitrile and 2,4-dichloro-pyrimidine, the title compound was isolated, after flash-chromatography, as a yellow solid in 69% yield (94% purity by HPLC).
MS(ESI$^+$): 231.4; MS(ESI$^-$): 229.6.

Intermediate 11: 4-pyrimidineacetonitrile, 2-chloro-5-methyl-alpha-(6-phenyl-2(1H)-pyridinylidene)- (cf. Scheme 5, compound II'b)

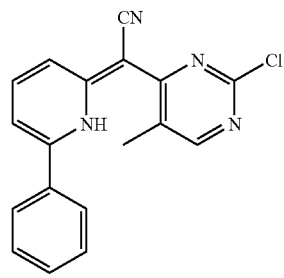

Following the general methods as outlined in Intermediate 5 (Method A), starting from 2-pyridineacetonitrile, 6-phenyl- (Intermediate 3) and 2,4-dichloro-5-methyl-pyrimidine, the title compound was isolated, after flash-chromatography, as a yellow solid in 97.5% yield (98% purity by HPLC).
$^1$H NMR (300 MHz, CDCl$_3$); 2.45 (s, 3H), 7.47 (d, Jd=8.64, 1H), 7.53 (d, Jd=7.53, 1H), 7.63-7.65 (m, 3H), 8.02-8.07 (m, 4H). MS(ESI$^+$): 321.2; MS(ESI$^-$): 319.1

Intermediate 12: 4-pyrimidineacetonitrile, 6-chloro-alpha-2(1H)-pyridinylidene- (cf. Scheme 4, compound II'a)

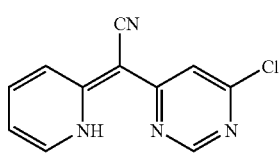

Following the general methods as outlined in Intermediate 5 (Method B), starting from 2-pyridylacetonitrile and 4,6-dichloro-pyrimidine, the title compound was isolated, after flash-chromatography, as a yellow solid in 60% yield (97% purity by HPLC).
MS(ESI$^+$): 231.5; MS(ESI$^-$): 229.7.

Intermediate 13: 1,3,5-triazine-2-acetonitrile, 4-chloro-6-(methylamino)-alpha-2(1H)-pyridinylidene- (cf. Scheme 6, compound II'c)

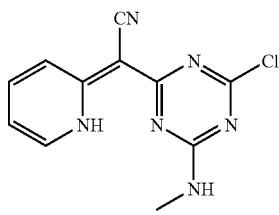

Following the general methods as outlined in Intermediate 5 (Method B), starting from 2-pyridylacetonitrile and 1,3,5-triazin-2-amine, 4,6-dichloro-N-methyl-, the title compound was isolated, after flash-chromatography, as a yellow solid in 61% yield (92% purity by HPLC).
MS(ESI$^+$): 261.5; MS(ESI$^-$): 259.7.

Intermediate 14: 4-pyrimidineacetonitrile, 2-chloro-4-methyl-alpha-2(1H)-pyridinylidene- (cf. Scheme 5, compound II'b)

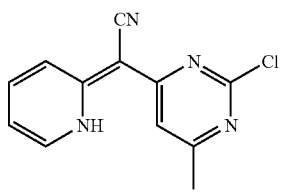

Following the general methods as outlined in Intermediate 5 (Method B), starting from 2-pyridylacetonitrile and 2,4-dichloro-6-methylpyrimidine, the title compound was isolated, after flash-chromatography, as a yellow solid in 62% yield (94% purity by HPLC).
MS(ESI$^+$): 245.8; MS(ESI$^-$): 243.9.

Intermediate 15: 4-pyrimidineacetonitrile, alpha-(6-bromo-2(1H)-pyridinylidene)-2-chloro-5-methyl (cf. Scheme 5, compound II'b)

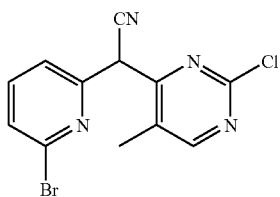

Following the general methods as outlined in Intermediate 5 (Method B), starting from 6-Bromopyridin-2-yl-acetonitrile and 2,4-dichloro-5-methyl-pyrimidine, the title compound was isolated, after flash-chromatography, as a yellow solid in 82% yield (98% purity by HPLC).

MS(ESI$^+$): 324.2; MS(ESI$^-$): 322.6.

Intermediate 16: 3-Bromo-2-bromomethylpyridine (cf. Scheme 7, compound VII)

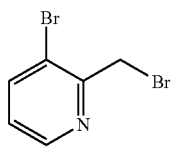

To a mixture of 3-bromo-2-methylpyridine (46.5 g, 0.27 mol) in CCl$_4$ (800 mL) was added NBS (53 g, 0.297 mol) and benzoylperoxide (4.7 g) and refluxed for 2 h in presence of light. The reaction mixture was cooled to 50° C. and filtered off the solid succinimide. The filtrate was concentrated and the crude 6-bromo-2-bromomethylpyridine was used for the follow-up reaction.

MS(ESI$^+$): 251.8; MS(ESI$^-$): 249.8

Intermediate 17: 3-Bromopyridin-2-yl-acetonitrile (cf. Scheme 7, compound IV)

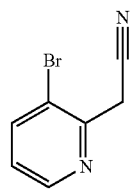

To a stirred solution of the above crude 3-bromo-2-bromomethylpyridine (70 g, 0.28 mol) in dioxane (500 mL) and water (250 mL), was added NaCN (28 g, 0.74 mol) at 0° C. and then stirred at RT for 16 h. The reaction mixture was quenched with 3 Lit of water and extracted with ethylacetate (4×500 mL). The organic layer was washed with water (400 L), brine (250 mL), dried over Na$_2$SO$_4$ and concentrated to give crude product. The crude was purified by column chromatography over silica gel (pet. ether/ethylacetate, 8:2) to give 3-bromopyridine-2-yl-acetonitrile (22 g, 40%). [TLC: Pet. ether/ethylacetate, 7:3, R$_f$=0.35]

MS(ESI$^+$): 199.2; MS(ESI$^-$): 197.2.

Intermediate 18: 4-pyrimidineacetonitrile alpha-(3-bromo-2(1H)-pyridinylidene)-2-chloro-5-methyl (cf. Scheme 5, compound II'b)

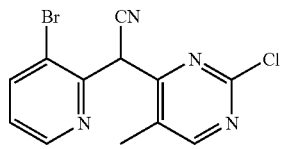

Following the general methods as outlined in Intermediate 5 (Method B), starting from 3-Bromopyridin-2-yl-acetonitrile and 2,4-dichloro-5-methyl-pyrimidine, the title compound was isolated, after flash-chromatography, as a yellow solid in 80% yield (98% purity by HPLC).

MS(ESI$^+$): 324.9; MS(ESI$^-$): 322.9.

Intermediate 19: 4-pyrimidineacetonitrile, alpha-(3-bromo-2(1H)-pyridinylidene)-2-chloro- (cf. Scheme 5, compound II'b)

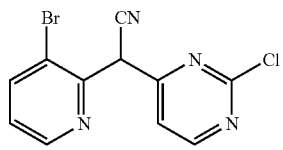

Following the general methods as outlined in Intermediate 5 (Method B), starting from 3-Bromopyridin-2-yl-acetonitrile and 2,4-dichloro-pyrimidine, the title compound was isolated, after flash-chromatography, as a yellow solid in 86% yield (96% purity by HPLC).

MS(ESI$^+$): 310.9; MS(ESI$^-$): 308.6.

Intermediate 20: 5-Bromo-2-bromomethylpyridine (cf. Scheme 7, compound VII)

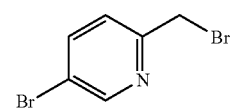

To a mixture of 5-bromo-2-methylpyridine (46.5 g, 0.27 mol) in CCl$_4$ (800 mL) was added NBS (53 g, 0.297 mol) and benzoylperoxide (4.7 g) and refluxed for 2 h in presence of light. The reaction mixture was cooled to 50° C. and filtered off the solid succinimide. The filtrate was concentrated and the crude 5-bromo-2-bromomethylpyridine was used for next reaction.

MS(ESI$^+$): 251.9; MS(ESI$^-$): 250.5

Intermediate 21: 4-pyrimidineacetonitrile, alpha-(5-bromo-2(1H)-pyridinylidene)-2-chloro- (cf. Scheme 5, compound II'b)

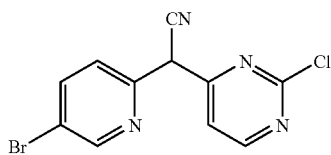

Following the general methods as outlined in Intermediate 5 (Method B), starting from 5-Bromopyridin-2-yl-acetonitrile and 2,4-dichloro-pyrimidine, the title compound was isolated, after flash-chromatography, as a yellow solid in 80% yield (92% purity by HPLC).

MS(ESI$^+$): 311.3; MS(ESI$^-$): 308.9.

Example 1

General Procedure for the Solution-Phase Synthesis of Pyridinyl Acetonitriles derivatives of General Formula I, with X as Above Defined and G'=G'a, G'b or G'c (Schemes 1-6): 4-pyrimidineacetonitrile, 2-(cyclopentylamino)-5-methyl-alpha-2-pyridinyl-

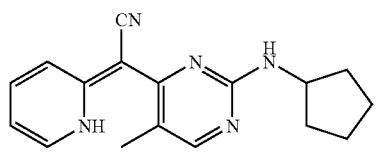

Method C:

To a solution of 4-pyrimidineacetonitrile, 4-pyrimidineacetonitrile, 2-chloro-5-methyl-alpha-2(1H)-pyridinylidene- (intermediate 5) (100 mg, 0.41 mmol, 1 eq) in 2 mL of iPrOH (or DMA:iPrOH (1:1)) was added triethylamine (0.113 mL, 0.82 mmol, 2 eq) and cyclopentylamine (0.121 mL, 1.23 mmol, 3 eq) in 2 mL of iPrOH (or DMA:iPrOH (1:1)). The reaction mixture was heated up to 165° C. for 50 min in a microwave device. To the reaction mixture was added 1 mL of water and 1 mL of 1M HCl. The precipitate was filtered off and washed with water, iPrOH, and/or acetonitrile and/or diethyl ether. The yellow solid was dissolved in 2 mL of DCM and 1 ml of a solution 50:50 DCM:TFA was added. The solution was evaporated in vacuo. The yellow solid was dried under vacuum overnight. The desired compound as a TFA salt, was isolated as a yellow solid (119 mg, 0.29 mmol, yield: 70%).

Method D:

To a solution of 4-pyrimidineacetonitrile, 2-chloro-5-methyl-alpha-2(1H)-pyridinylidene- (intermediate 5) (100 mg, 0.41 mmol, 1 eq) in 2 mL of iPrOH (or DMA:iPrOH (1:1)) was added triethylamine (0.113 mL, 0.82 mmol, 2 eq) and cyclopentylamine (0.121 mL, 1.23 mmol, 3 eq) in 2 mL of iPrOH (or DMA:iPrOH (1:1)). The reaction mixture was heated up to 165° C. for 50 min in a microwave device. To the reaction mixture was added 1 mL of water and 1 mL of 1M HCl. The reaction mixture was evaporated under vacuum and the residue was dissolved in 1 mL of DMSO and then purified by preparative HPLC using a gradient 10% Acetonitrile in 0.01% TFA in water to 100% acetonitrile. The fractions were collected to give the desired product as a TFA salt.

Method E:

10 mg of Building Blocks were dissolved in 0.3 mL of DMA. Et$_3$N (4 eq.) and the amines (4 eq.) dissolved in DMA (0.3 mL) were then added to the reaction mixtures and the plate was sealed and heated in a microwave (Mars 5) as follow: 2 plates at a time were heated 4 min at 300 Watts and then left to cool down for 10 min. This was repeated 4 times. The reaction mixtures were then transferred into a 2 mL plate and the solvent was removed in the Genevac. Work up: 1 mL of water/CH$_3$COOH (2%) was then added and the plate was shaken for 3 h00. The aqueous layer was removed using the Zymark, leaving the solid behind. This solid was further washed with water (twice). 1 mL of MeOH/TFA (20%) was added to the plates, which were shaken at room temperature for 48 h00 and the supernatant was collected using the Lissy. Analytical plates were made and the solvents were removed in the Genevac.

4-pyrimidineacetonitrile, 2-(cyclopentylamino)-5-methyl-alpha-2-pyridinyl-: yellow solid;

$^1$H NMR (300 MHz, DMSO); 1.46-1.72 (m, 6H), 1.91-2.02 (m, 2H), 2.29 (s, 3H), 4.08-4.16 (m, 1H), 6.93 (t, 1H), 7.36-7.44 (m, 1H), 7.63 (s, 1H), 7.74-7.89 (m, 1H), 8.25 (d, 1H).

MS (ESI$^+$) 294, (ESI$^-$) 292.

Example 2

4-pyrimidineacetonitrile, 2-[[1-(diphenylmethyl)-3-azetidinyl]amino]-5-methyl-alpha-2(1H)-pyridinylidene-

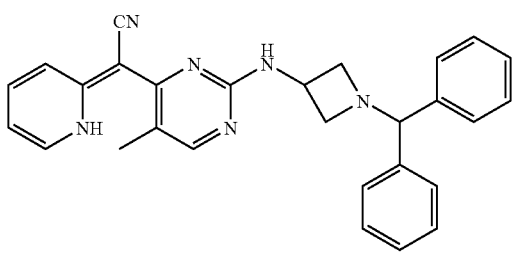

Following the general methods as outlined in Example 1 (Method D), starting from 4-pyrimidineacetonitrile, 2-chloro-5-methyl-alpha-2(1H)-pyridinylidene- (intermediate 5), and 1-benzhydryl-azetidin-3-ylamine, the title compound was isolated, as a yellow solid in 82% yield (92% purity by HPLC).

MS(ESI$^+$): 447.5; MS(ESI$^-$): 445.6.

Example 3

4-pyrimidineacetonitrile, 5-methyl-2-[[2-(3-pyridinyl)ethyl]amino]-alpha-2(1H)-pyridinylidene-

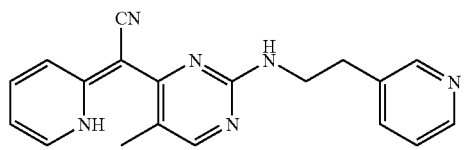

Following the general methods as outlined in Example 1 (Method D), starting from 4-pyrimidineacetonitrile, 2-chloro-5-methyl-alpha-2(1H)-pyridinylidene- (intermediate 5), and 3-(2-aminoethyl)pyridine, the title compound was isolated, as a yellow solid in 78% yield (99% purity by HPLC).

MS(ESI$^+$): 331.2; MS(ESI$^-$): 329.6.

Example 4

4-pyrimidineacetonitrile, 2-[[2-[6-(dimethylamino)-3-pyridinyl]ethyl]amino]-5-methyl-alpha-2(1H)-pyridinylidene-

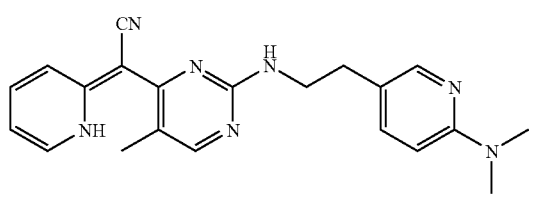

Following the general methods as outlined in Example 1 (Method D), starting from 4-pyrimidineacetonitrile, 2-chloro-5-methyl-alpha-2(1H)-pyridinylidene- (intermediate 5), and 2-(N,N-dimethylamino)-5-aminoethyl pyridine, the title compound was isolated, as a yellow solid in 76% yield (98% purity by HPLC).

MS(ESI$^+$): 374.3; MS(ESI$^-$): 372.6.

Example 5

4-pyrimidineacetonitrile, 5-methyl-2-[[3-(2-oxo-1-pyrrolidinyl)propyl]amino]-alpha-2(1H)-pyridinylidene-

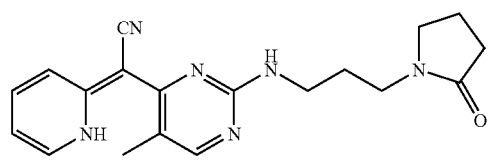

Following the general methods as outlined in Example 1 (Method D), starting from 4-pyrimidineacetonitrile, 2-chloro-5-methyl-alpha-2(1H)-pyridinylidene- (intermediate 5), and N-(3'-aminopropyl)-2-pyrrolidinone, the title compound was isolated, as a yellow solid in 87% yield (98% purity by HPLC).

MS(ESI$^+$): 351.3; MS(ESI$^-$): 349.2.

Example 6

4-pyrimidineacetonitrile, 5-methyl-alpha-2-pyridinyl-2-[[2-(2-pyridinyl)ethyl]amino]-

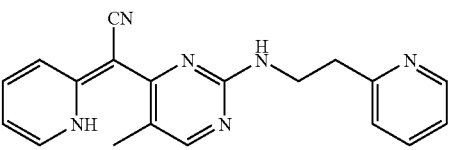

Following the general methods as outlined in Example 1 (Method D), starting from 4-pyrimidineacetonitrile, 2-chloro-5-methyl-alpha-2(1H)-pyridinylidene- (intermediate 5), and 2-(2-aminoethyl)pyridine, the title compound was isolated, as a yellow solid in 84% yield (97% purity by HPLC).

MS(ESI$^+$): 331.2; MS(ESI$^-$): 329.3.

Example 7

4-pyrimidineacetonitrile, 2-(cyclopentylamino)-5-methyl-alpha-(6-phenyl-2(1H)-pyridinylidene)-

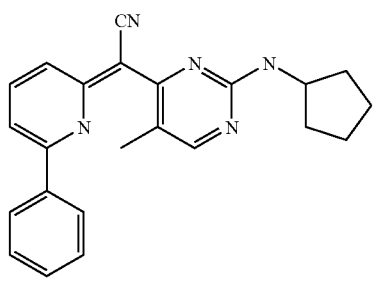

Following the general methods as outlined in Example 1 (Method D), starting from 4-pyrimidineacetonitrile, 2-chloro-5-methyl-alpha-2(1H)-pyridinylidene- (intermediate 5), and cyclopentylamine, the title compound was isolated, as a yellow solid in 80% yield (97% purity by HPLC).

$^1$H NMR (300 MHz, DMSO); 1.13-1.15 (broad m, 2H), 1.30-1.32 (broad m, 2H), 2.36 (s, 3H), 4.05 (broad s, 1H), 7.55-7.46 (m, 6H), 7.76 (broad s, 1H), 7.90-7.96 (m, 2H), 8.05 (d, J=7.6 Hz, 1H), 8.13 (t, Jt=7.53, 1H). MS(ESI$^+$): 370.3; MS(ESI$^-$): 368.2.

Example 8

4-pyrimidineacetonitrile, 2-(cyclohexylamino)-5-methyl-alpha-2-pyridinyl-

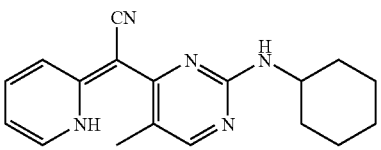

Following the general methods as outlined in Example 1 (Method C), starting from 4-pyrimidineacetonitrile, 2-chloro-5-methyl-alpha-2(1H)-pyridinylidene- (intermediate 5), and cyclohexylamine, the title compound was isolated, as a yellow solid in 89% yield (99% purity by HPLC).

MS(ESI$^+$): 308.2; MS(ESI$^-$): 306.2.

Example 9

4-pyrimidineacetonitrile, 2-[(cyclohexylmethyl)amino]-5-methyl-alpha-2 pyridinyl-

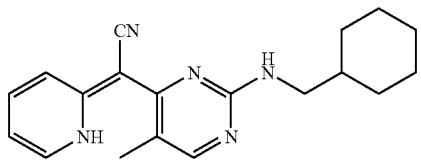

Following the general methods as outlined in Example 1 (Method D), starting from 4-pyrimidineacetonitrile, 2-chloro-5-methyl-alpha-2(1H)-pyridinylidene- (intermediate 5), and (aminoethyl)cyclohexane, the title compound was isolated, as a yellow solid in 82% yield (99% purity by HPLC).

MS(ESI$^+$): 322.4; MS(ESI$^-$): 320.2.

Example 10

4-pyrimidineacetonitrile, 2-[(3-hydroxy-1-phenyl-propyl)amino]-5-methyl alpha-2(1H-pyridinylidene-

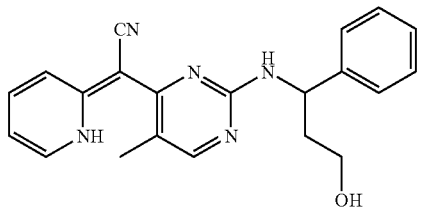

Following the general methods as outlined in Example 1 (Method D), starting from 4-pyrimidineacetonitrile, 2-chloro-5-methyl-alpha-2(1H)-pyridinylidene- (intermediate 5), and 3-amino-3-phenyl-1-propanol, the title compound was isolated, as a yellow solid in 66% yield (96% purity by HPLC).

MS(ESI$^+$): 360.4; MS(ESI$^-$): 358.2.

Example 11

4-pyrimidineacetonitrile, 2-(cyclobutylamino)-5-methyl-alpha-2(1H)-pyridinylidene

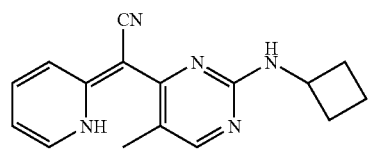

Following the general methods as outlined in Example 1 (Method C), starting from 4-pyrimidineacetonitrile, 2-chloro-5-methyl-alpha-2(1H)-pyridinylidene- (intermediate 5), and cyclobutylamine, the title compound was isolated, as a yellow solid in 80% yield (98% purity by HPLC).

MS(ESI$^+$): 280.5; MS(ESI$^-$): 278.5.

Example 12 and 13

1-piperidinecarboxylic acid, 4-[[4-[(E)-cyano-2(1H)-pyridinylidenemethyl]-5-methyl-2-pyrimidinyl]amino]-, 1,1-dimethylethyl ester and 4-pyrimidineacetonitrile, 5-methyl-2-(4-piperidinylamino)-alpha-2(1H)-pyridinylidene-

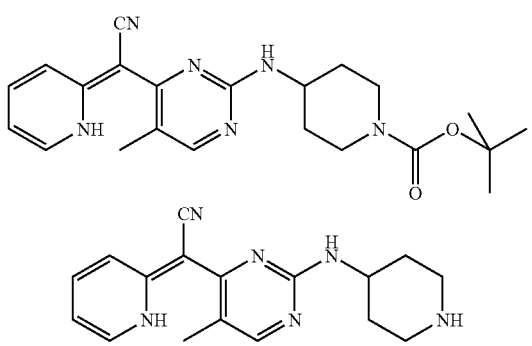

Following the general methods as outlined in Example 1 (Method D), starting from 4-pyrimidineacetonitrile, 2-chloro-5-methyl-alpha-2(1H)-pyridinylidene- (intermediate 5), and 4-amino-1-N-Boc-piperidine, the title compound was isolated, as a yellow solid in 70% yield (92% purity by HPLC).

MS(ESI$^+$): 409.3; MS(ESI$^-$): 407.2.

1-piperidinecarboxylic acid, 4-[[4-[(E)-cyano-2(1H)-pyridinylidenemethyl]-5-methyl-2-pyrimidinyl]amino]-, 1,1-dimethylethyl ester (Example 12, 15 mg, 0.036 mmol) was dissolved in 2 mL of a solution of 70:30 DCM:TFA at room temperature. The reaction mixture was stirred at room temperature for 2 h. The solvents were evaporated under vacuum and the desired product was isolated as a TFA salt (orange oil, 9 mg, 0.021 mmol, yield: 60%).

MS(ESI$^+$): 309.2; MS(ESI$^-$): 307.2.

Example 14

4-pyrimidineacetonitrile, 2-(cyclopentylamino)-alpha-(1-ethyl-2(1H)-pyridinylidene)-5-methyl

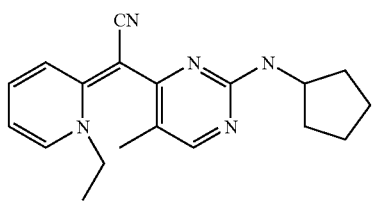

To a solution of 4-pyrimidineacetonitrile, 2-(cyclopentylamino)-5-methyl-alpha-2-pyridinyl- (Example 1, 50 mg, 0.17 mmol, 1 eq) in 4 mL of anhydrous DMF, were added potassium tert-butoxide (29 mg, 0.26 mmol, 1.5 eq) and iodoethane (15 µL, 0.19 mmol, 1.1 eq). The reaction mixture was heated up to 40° C. for 4 days and cooled down to room temperature. The reaction mixture was diluted with 50 mL of EtOAc and the organics were washed with 3×10 mL of a solution of (NaHCO₃ sat, water, brine, 1:1:1). The organic layer was dried over magnesium sulfate. The residue was redissolved in 1M of DNSO and purified by preparative HPLC using a gradient 10% Acetonitrile in 0.01% TFA in water to 100% acetonitrile. The fractions was collected and evaporated to give the desired product as a TFA salt (yellow oil, 22 mg, yield: 31%).

¹H NMR (300 MHz, DMSO); 1.28 (t, 3H), 1.65-2.0 (m, 6H), 2.03 (s, 3H), 2.26-2.37 (m, 2H), 2.58-2.70 (m, 1H), 2.88-3.00 (m, 1H), 4.60-4.64 (m, 1H), 7.48-7.56 (m, 1H), 7.83 (d, 1H), 7.97-8.07 (m, 2H), 8.75 (d, 1H), 10.09 (br, 1H). MS (ESI+) 322, (ESI−) 320.

Example 15

4-pyrimidineacetonitrile, 2-(cyclopropylamino)-5-methyl-alpha-2-pyridinyl-

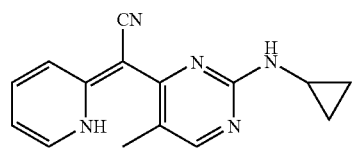

Following the general methods as outlined in Example 1 (Method D), starting from 4-pyrimidineacetonitrile, 2-chloro-5-methyl-alpha-2(1H)-pyridinylidene- (intermediate 5), and cyclopropylamine, the title compound was isolated, as a yellow solid in 72% yield (92% purity by HPLC).

MS(ESI⁺): 266.5; MS(ESI⁻): 264.2.

Example 16

4-pyrimidineacetonitrile, 5-methyl-2-[[1-(phenylmethyl)-4-piperidinyl]amino]-alpha-2(1H)-pyridinylidene-

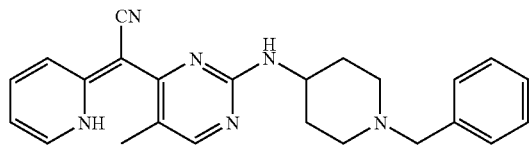

Following the general methods as outlined in Example 1 (Method D), starting from 4-pyrimidineacetonitrile, 2-chloro-5-methyl-alpha-2(1H)-pyridinylidene- (intermediate 5), and 4-amino-1-benzylpiperidine, the title compound was isolated, as a yellow solid in 74% yield (98% purity by HPLC).

MS(ESI⁺): 399.5; MS(ESI⁻): 397.2.

Example 17

4-pyrimidineacetonitrile, 2-[(1-ethylpropyl)amino]-5-methyl-alpha-2(1H)-pyridinylidene-

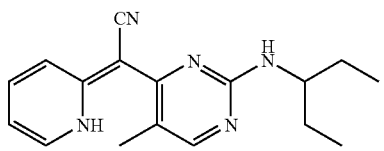

Following the general methods as outlined in Example 1 (Method D), starting from 4-pyrimidineacetonitrile, 2-chloro-5-methyl-alpha-2(1H)-pyridinylidene- (intermediate 5), and 3-aminopentane, the title compound was isolated, as a yellow solid in 74% yield (98% purity by HPLC).

MS(ESI⁺): 296.4; MS(ESI⁻): 294.5.

Example 18

4-pyrimidineacetonitrile, 5-methyl-alpha-2(1H)-pyridinylidene-2-[[(tetrahydro-2H-pyran-4-yl)methyl]amino]-

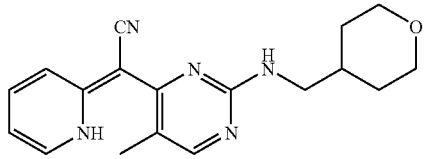

Following the general methods as outlined in Example 1 (Method D), starting from 4-pyrimidineacetonitrile, 2-chloro-5-methyl-alpha-2(1H)-pyridinylidene- (intermediate 5), and 4-aminoethyltetrahydropyran, the title compound was isolated, as a yellow solid in 70% yield (97% purity by HPLC).

MS(ESI⁺): 324.2; MS(ESI⁻): 322.2.

Example 19

4-pyrimidineacetonitrile, 5-methyl-alpha-(1H)-pyridinylidene-2-[[(tetrahydro-2-furanyl)methyl]amino]-

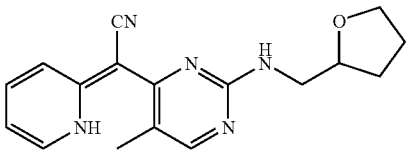

Following the general methods as outlined in Example 1 (Method D), starting from 4-pyrimidineacetonitrile, 2-chloro-5-methyl-alpha-2(1H)-pyridinylidene- (intermediate 5), and tetrahydrofurfurylamine, the title compound was isolated, as a yellow solid in 60% yield (92% purity by HPLC).

MS(ESI⁺): 310.6; MS(ESI⁻): 308.2.

Example 20

4-pyrimidineacetonitrile, 5-methyl-2-[(2-methylpropyl)amino]-alpha-2(1H)-pyridinylidene-

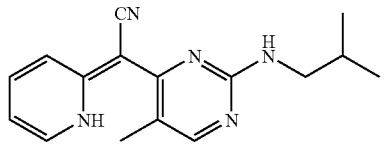

Following the general methods as outlined in Example 1 (Method C), starting from 4-pyrimidineacetonitrile, 2-chloro-5-methyl-alpha-2(1H)-pyridinylidene- (intermediate 5), and isobutylamine, the title compound was isolated, as a yellow solid in 69% yield (91% purity by HPLC).

MS(ESI$^+$): 282.4; MS(ESI$^-$): 280.6.

Example 21

4-pyrimidineacetonitrile, 5-methyl-2-[(1-methylethyl)amino]-alpha-2(1H)-pyridinylidene-

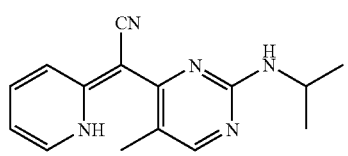

Following the general methods as outlined in Example 1 (Method D), starting from 4-pyrimidineacetonitrile, 2-chloro-5-methyl-alpha-2(1H)-pyridinylidene- (intermediate 5), and isopropylamine, the title compound was isolated, as a yellow solid in 80% yield (98% purity by HPLC).

MS(ESI$^+$): 268.4; MS(ESI$^-$): 266.2.

Example 22

4-pyrimidineacetonitrile, 2-[[(1S,2S)-2-hydroxycyclohexyl]amino]-5-methyl-alpha-2(1H)-pyridinylidene-

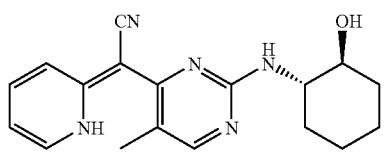

Following the general methods as outlined in Example 1 (Method D), starting from 4-pyrimidineacetonitrile, 2-chloro-5-methyl-alpha-2(1H)-pyridinylidene- (intermediate 5), and trans-2-aminocyclohexanol, the title compound was isolated, as a yellow solid in 79% yield (92% purity by HPLC).

MS(ESI$^+$): 324.5; MS(ESI$^-$): 322.6.

Example 23

4-pyrimidineacetonitrile, 2-[[(1S,2S)-2-hydroxycyclopentyl]amino]-5-methyl-alpha-2(1H)-pyridinylidene-

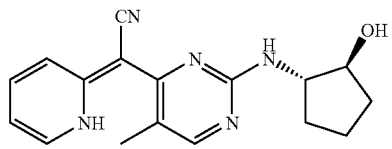

Following the general methods as outlined in Example 1 (Method D), starting from 4-pyrimidineacetonitrile, 2-chloro-5-methyl-alpha-2(1H)-pyridinylidene- (intermediate 5), and trans-2-aminocyclopentanol hydrochloride, the title compound was isolated, as a yellow solid in 89% yield (91% purity by HPLC).

MS(ESI$^+$): 310.4; MS(ESI$^-$): 308.4

Example 24

4-pyrimidineacetonitrile, 2-[(trans-4-hydroxycyclohexyl)amino]-5-methyl-alpha-2(1H)-pyridinylidene-

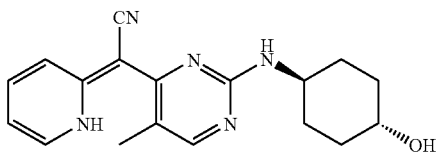

Following the general methods as outlined in Example 1 (Method D), starting from 4-pyrimidineacetonitrile, 2-chloro-5-methyl-alpha-2(1H)-pyridinylidene- (intermediate 5), and trans-4-aminocyclohexanol hydrochloride, the title compound was isolated, as a yellow solid in 89% yield (91% purity by HPLC).

MS(ESI$^+$): 324.4; MS(ESI$^-$): 322.6.

Example 25

4-pyrimidineacetonitrile, 5-methyl-2-[(1-methylbutyl)amino]-alpha-2-pyridinyl-

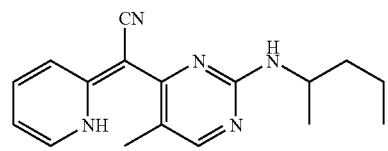

Following the general methods as outlined in Example 1 (Method D), starting from 4-pyrimidineacetonitrile, 2-chloro-5-methyl-alpha-2(1H)-pyridinylidene- (intermediate 5), and (+/−)-2-aminopentane, the title compound was isolated, as a yellow solid in 88% yield (92% purity by HPLC).

MS(ESI⁺): 296.3; MS(ESI⁻): 294.5.

Example 26

4-pyrimidineacetonitrile, 2-(cyclopentylamino)-alpha-2-pyridinyl-

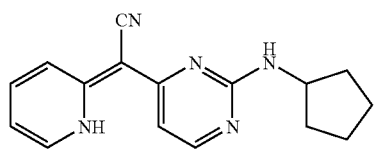

Following the general methods as outlined in Example 1 (Method E), starting from 4-pyrimidineacetonitrile, 2-chloro-alpha-2(1H)-pyridinylidene- (intermediate 6), and cyclopentylamine, the title compound was isolated, as a yellow solid in 86% yield (87% purity by HPLC).

MS(ESI⁺): 280.5; MS(ESI⁻): 278.2.

Example 27

4-pyrimidineacetonitrile, 2-(cyclohexylamino)-alpha-2-pyridinyl-

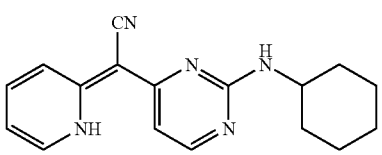

Following the general methods as outlined in Example 1 (Method E), starting from 4-pyrimidineacetonitrile, 2-chloro-alpha-2(1H)-pyridinylidene- (intermediate 6), and cyclohexylamine, the title compound was isolated, as a yellow solid in 85% yield (77% purity by HPLC).

MS(ESI⁺): 294.5; MS(ESI⁻): 292.3.

Example 28

4-pyrimidineacetonitrile, 5-methyl-alpha-2-pyridinyl-2-[4-(2-pyrimidinylamino)-1-piperidinyl]-

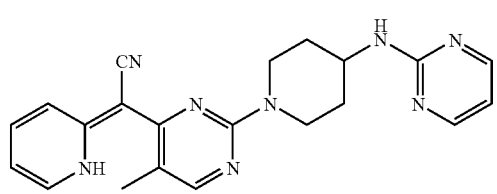

Following the general methods as outlined in Example 1 (Method E), starting from 4-pyrimidineacetonitrile, 2-chloro-5-methyl-alpha-2(1H)-pyridinylidene- (intermediate 5), and 2-(N-4-piperidinyl)-aminopyrimidine, the title compound was isolated, as a yellow solid in 84% yield (90% purity by HPLC).

MS(ESI⁺): 387.8; MS(ESI⁻): 385.2.

Example 29

4-pyrimidineacetonitrile, alpha-2-pyridinyl-2-[[2-(3-pyridinyl)ethyl]amino]-

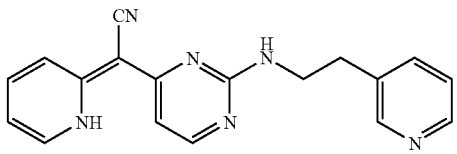

Following the general methods as outlined in Example 1 (Method E), starting from 4-pyrimidineacetonitrile, 2-chloro-alpha-2(1H)-pyridinylidene- (intermediate 6), and 3-(2-aminoethyl)pyridine, the title compound was isolated, as a yellow solid in 80% yield (77% purity by HPLC).

MS(ESI⁺): 317.8; MS(ESI⁻): 315.2.

Example 30

4-pyrimidineacetonitrile, 2-(cyclopropylamino)-alpha-2-pyridinyl-

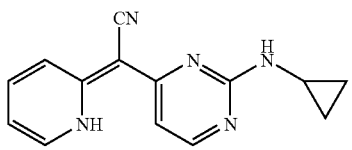

Following the general methods as outlined in Example 1 (Method E), starting from 4-pyrimidineacetonitrile, 2-chloro-alpha-2(1H)-pyridinylidene- (intermediate 6), and cyclopropylamine, the title compound was isolated, as a yellow solid in 70% yield (87% purity by HPLC).

MS(ESI⁺): 252.2; MS(ESI⁻): 250.3.

Example 31 benzoic acid 4-[2-[[4-(cyano-2-pyridinylmethyl)-5-methyl-2-pyrimidinyl amino]ethyl]-, methyl ester

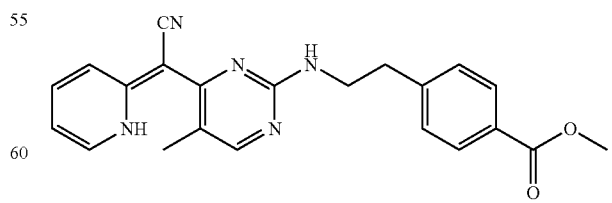

Following the general methods as outlined in Example 1 (Method E), starting from 4-pyrimidineacetonitrile, 2-chloro-5-methyl-alpha-2(1H)-pyridinylidene- (intermediate 5), and methyl-4-(2-aminoethyl)benzoate hydrochloride, the title compound was isolated, as a yellow solid in 74% yield (98% purity by HPLC).

MS(ESI⁺): 388.4; MS(ESI⁻): 386.5.

Example 32

4-pyrimidineacetonitrile, 2-[(1,2-dimethylpropyl)amino]-5-methyl-alpha-2-pyridinyl-

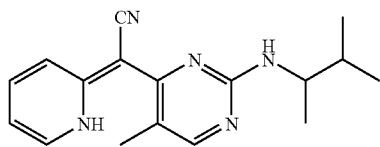

Following the general methods as outlined in Example 1 (Method E), starting from 4-pyrimidineacetonitrile, 2-chloro-5-methyl-alpha-2(1H)-pyridinylidene- (intermediate 5), and 2-amino-3-methylbutane, the title compound was isolated, as a yellow solid in 77% yield (92% purity by HPLC).

MS(ESI⁺): 296.3; MS(ESI⁻): 294.5.

Example 33

4-pyrimidineacetonitrile, 2-[(2,3-dimethylcyclohexyl)amino]-5-methyl-alpha-2-pyridinyl-

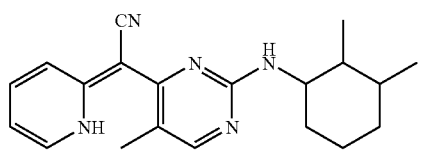

Following the general methods as outlined in Example 1 (Method E), starting from 4-pyrimidineacetonitrile, 2-chloro-5-methyl-alpha-2(1H)-pyridinylidene- (intermediate 5), and 2,3-dimethylcyclohexylamine, the title compound was isolated, as a yellow solid in 87% yield (94% purity by HPLC).

MS(ESI⁺): 336.4; MS(ESI⁻): 334.5.

Example 34

4-pyrimidineacetonitrile, alpha-4-pyridinyl-2-[[2-(3-pyridinyl)ethyl]amino]-

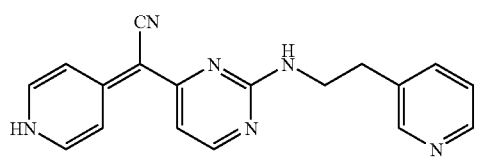

Following the general methods as outlined in Example 1 (Method E), starting from 4-pyrimidineacetonitrile, 2-chloro-alpha-4(1H)-pyridinylidene- (intermediate 10), and 3-(2-aminoethyl)pyridine, the title compound was isolated, as a yellow solid in 60% yield (74% purity by HPLC).

MS(ESI⁺): 317.8; MS(ESI⁻): 315.6.

Example 35

4-pyrimidineacetonitrile, 2-[(2-furanylmethyl)amino]-5-methyl-alpha-2-pyridinyl-

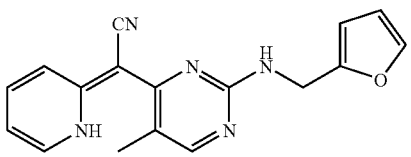

Following the general methods as outlined in Example 1 (Method E), starting from 4-pyrimidineacetonitrile, 2-chloro-5-methyl-alpha-2(1H)-pyridinylidene- (intermediate 5), and furfurylamine, the title compound was isolated, as a yellow solid in 78% yield (98% purity by HPLC).

MS(ESI⁺): 306.6; MS(ESI⁻): 304.5

Example 36

4-pyrimidineacetonitrile, 2-[(1-methylbutyl)amino]-aloha-2-pyridinyl-

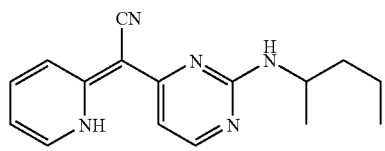

Following the general methods as outlined in Example 1 (Method E), starting from 4-pyrimidineacetonitrile, 2-chloro-alpha-2(1H)-pyridinylidene- (intermediate 6), and (+/−)-2-aminopentane, the title compound was isolated, as a yellow solid in 72% yield (97% purity by HPLC).

MS(ESI⁺): 282.6; MS(ESI⁻): 280.9.

Example 37

4-pyrimidineacetonitrile, 5-methyl-2-[[2-(1H-pyrazol-1-yl)ethyl]amino]-alpha-2-pyridinyl-

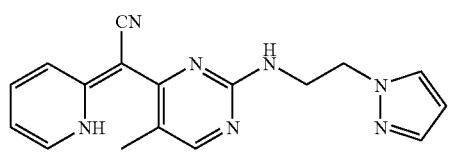

Following the general methods as outlined in Example 1 (Method E), starting from 4-pyrimidineacetonitrile, 2-chloro-5-methyl-alpha-2(1H)-pyridinylidene- (intermediate 5), and 1-(2'-aminoethyl)pyrazole, the title compound was isolated, as a yellow solid in 68% yield (88% purity by HPLC).

MS(ESI⁺): 320.3; MS(ESI⁻): 318.8.

Example 38

4-pyrimidineacetonitrile, 2-[[2-(4-aminophenyl)ethyl]amino]-5-methyl-alpha-2-pyridinyl-

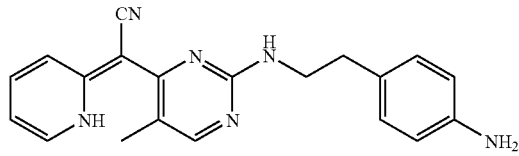

Following the general methods as outlined in Example 1 (Method E), starting from 4-pyrimidineacetonitrile, 2-chloro-5-methyl-alpha-2(1H)-pyridinylidene- (intermediate 5), and 2-(4-aminophenyl)ethylamine, the title compound was isolated, as a yellow solid in 80% yield (77% purity by HPLC).

MS(ESI⁺): 345.2; MS(ESI⁻): 343.4.

Example 39

4-pyrimidineacetonitrile, 2-[[(4-methoxyphenyl)methyl]amino]-5-methyl-alpha-2-pyridinyl-

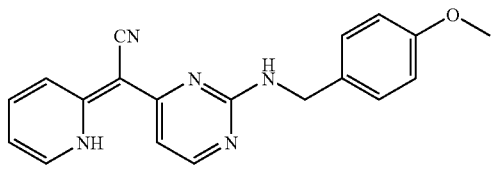

Following the general methods as outlined in Example 1 (Method E), starting from 4-pyrimidineacetonitrile, 2-chloro-5-methyl-alpha-2(1H)-pyridinylidene- (intermediate 5), and 4-methoxybenzylamine, the title compound was isolated, as a yellow solid in 70% yield (87% purity by HPLC).

MS(ESI⁺): 346.2; MS(ESI⁻): 344.2.

Example 40

4-pyrimidineacetonitrile, 6-(cyclopentylamino)-alpha-2-pyridinyl-

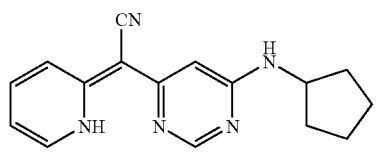

Following the general methods as outlined in Example 1 (Method E), starting from 4-pyrimidineacetonitrile, 6-chloro-alpha-2(1H)-pyridinylidene- (intermediate 12), and cyclopentylamine, the title compound was isolated, as a yellow solid in 69% yield (87% purity by HPLC).

MS(ESI⁺): 280.4; MS(ESI⁻): 278.2.

Example 41

4-pyrimidineacetonitrile, alpha-2-pyridinyl-2-[[2-(2-pyridinyl)ethyl]amino]-

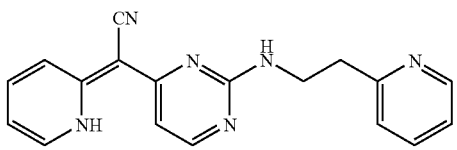

Following the general methods as outlined in Example 1 (Method E), starting from 4-pyrimidineacetonitrile, 2-chloro-alpha-2(1H)-pyridinylidene- (intermediate 6), and 2-(2-aminoethyl)pyridine, the title compound was isolated, as a yellow solid in 67% yield (84% purity by HPLC).

MS(ESI⁺): 316.2; MS(ESI⁻): 314.5.

Example 42

4-pyrimidineacetonitrile, 2-(4-ethyl-1-piperazinyl)-6-methyl-alpha-2-pyridinyl-

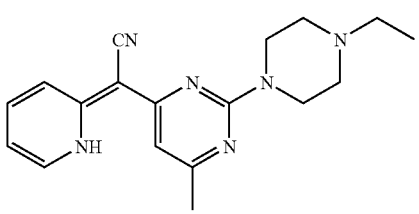

Following the general methods as outlined in Example 1 (Method E), starting from 4-pyrimidineacetonitrile, 2-chloro-4-methyl-alpha-2(1H)-pyridinylidene- (intermediate 14), and 1-ethylpiperazine, the title compound was isolated, as a yellow solid in 84% yield (92% purity by HPLC).

MS(ESI⁺): 322.2; MS(ESI⁻): 320.5.

Example 43

4-pyrimidineacetonitrile, 2-(cyclopentylamino)-alpha-4-pyridinyl-

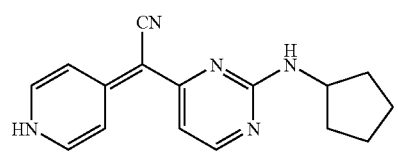

Following the general methods as outlined in Example 1 (Method E), starting from 4-pyrimidineacetonitrile, 2-chloro-alpha-4(1H)-pyridinylidene- (intermediate 10), and cyclopentylamine, the title compound was isolated, as a yellow solid in 62% yield (77% purity by HPLC).
MS(ESI⁺): 280.3; MS(ESI⁻): 278.2.

Example 44

4-pyrimidineacetonitrile, 2-[[[4-(difluoromethoxy)phenyl]methyl]amino]-alpha-2-pyridinyl-

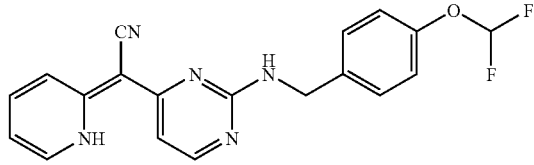

Following the general methods as outlined in Example 1 (Method E), starting from 4-pyrimidineacetonitrile, 2-chloro-alpha-2(1H)-pyridinylidene- (intermediate 6), and 4-(difluoromethoxy)benzylamine, the title compound was isolated, as a yellow solid in 89% yield (87% purity by HPLC).
MS(ESI⁺): 368.6; MS(ESI⁻): 364.5.

Example 45

4-pyrimidineacetonitrile, 2-[(2,3-dimethylcyclohexyl amino]-alpha-2-pyridinyl-

Following the general methods as outlined in Example 1 (Method E), starting from 4-pyrimidineacetonitrile, 2-chloro-alpha-2(1H)-pyridinylidene- (intermediate 6), and 2,3-dimethylcyclohexylamine, the title compound was isolated, as a yellow solid in 62% yield (98% purity by HPLC).
MS(ESI⁺): 322.6; MS(ESI⁻): 320.5.

Example 46

4-pyrimidineacetonitrile, 6-methyl-2-[(1-methylbutyl)amino]-alpha-2-pyridinyl-

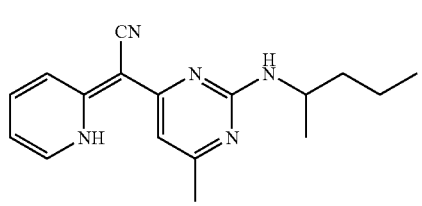

Following the general methods as outlined in Example 1 (Method E), starting from 4-pyrimidineacetonitrile, 2-chloro-4-methyl-alpha-2(1H)-pyridinylidene- (intermediate 14), and (+/−)-2-aminopentane, the title compound was isolated, as a yellow solid in 82% yield (96% purity by HPLC).
MS(ESI⁺): 296.2; MS(ESI⁻): 294.2.

Example 47

4-pyrimidineacetonitrile, 2-[(2-furanylmethyl)amino]-alpha-2-pyridinyl-

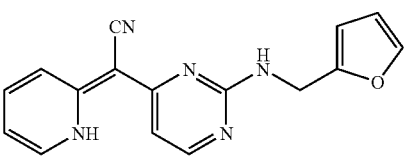

Following the general methods as outlined in Example 1 (Method E), starting from 4-pyrimidineacetonitrile, 2-chloro-alpha-2(1H)-pyridinylidene- (intermediate 6), and furfurylamine, the title compound was isolated, as a yellow solid in 72% yield (88% purity by HPLC).
MS(ESI⁺): 292.2; MS(ESI⁻): 290.9.

Example 48

4-pyrimidineacetonitrile, 2-(cyclopentylamino)-6-methyl-alpha-2-pyridinyl-

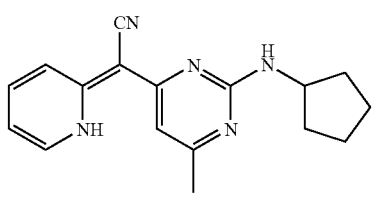

Following the general methods as outlined in Example 1 (Method E), starting from 4-pyrimidineacetonitrile, 2-chloro-4-methyl-alpha-2(1H)-pyridinylidene- (intermediate 14), and cyclopentylamine, the title compound was isolated, as a yellow solid in 74% yield (78% purity by HPLC).
MS(ESI⁺): 294.4; MS(ESI⁻): 292.2.

Example 49

1,3,5-triazine-2-acetonitrile, 4-(methylamino)-alpha-2-pyridinyl-6-[[2-(3-pyridinyl)ethyl]amino]-

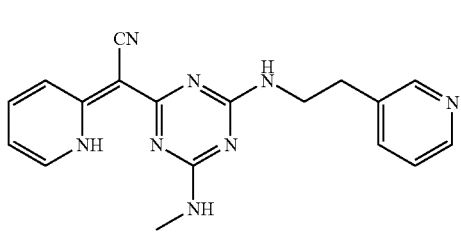

Following the general methods as outlined in Example 1 (Method E), starting from 1,3,5-triazine-2-acetonitrile, 4-chloro-6-(methylamino)-alpha-2(1H)-pyridinylidene- (intermediate 13), and 3-(2-aminoethyl)pyridine, the title compound was isolated, as a yellow solid in 66% yield (78% purity by HPLC).

MS(ESI+): 347.5; MS(ESI−): 345.4.

Example 50

4-pyrimidineacetonitrile, 2-[[2-[6-(dimethylamino)-3-pyridinyl]ethyl]amino]-alpha-2-pyridinyl-

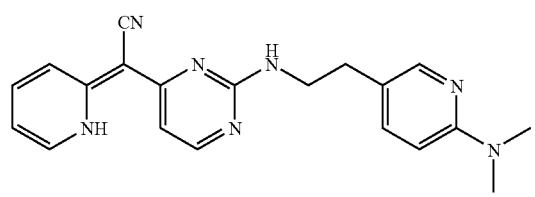

Following the general methods as outlined in Example 1 (Method E), starting from 4-pyrimidineacetonitrile, 2-chloro-alpha-2(1H)-pyridinylidene- (intermediate 6), and 2-(N,N-dimethylamino)-5-aminoethyl pyridine, the title compound was isolated, as a yellow solid in 62% yield (82% purity by HPLC).

MS(ESI+): 360.2; MS(ESI−): 358.4.

Example 51

4-pyrimidineacetonitrile, 2-(dipropylamino)-5-methyl-alpha-2-pyridinyl-

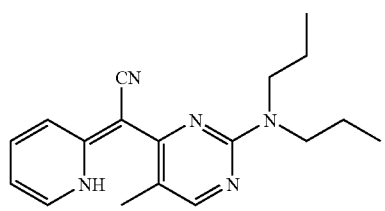

Following the general methods as outlined in Example 1 (Method E), starting from 4-pyrimidineacetonitrile, 2-chloro-5-methyl-alpha-2(1H)-pyridinylidene- (intermediate 5), and dipropylamine, the title compound was isolated, as a yellow solid in 82% yield (82% purity by HPLC).

MS(ESI+): 310.3; MS(ESI−): 308.5.

Example 52

4-pyrimidineacetonitrile alpha-2-pyridinyl-6-[[2-(3-pyridinyl)ethyl]amino]-

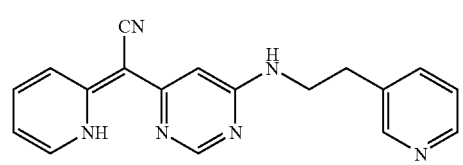

Following the general methods as outlined in Example 1 (Method E), starting from 4-pyrimidineacetonitrile, 6-chloro-alpha-2(1H)-pyridinylidene- (intermediate 12), and 3-(2-aminoethyl)pyridine, the title compound was isolated, as a yellow solid in 60% yield (77% purity by HPLC).

MS(ESI+): 317.2; MS(ESI−): 315.3.

Example 53

4-pyrimidineacetonitrile alpha-(3-bromo-2(1H)-pyridinylidene)-5-methyl-2-[[3-(1H-1,2,4-triazol-1-yl)propyl]amino]-

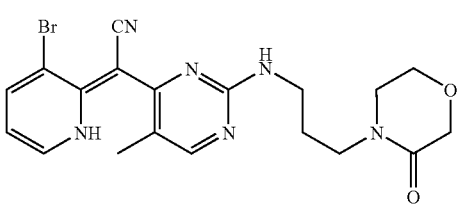

Following the general methods as outlined in Example 1 (Method E), starting from 4-pyrimidineacetonitrile, alpha-(3-bromo-2(1H)-pyridinylidene)-2-chloro-5-methyl (intermediate 18), and 3-(1H-1,2,4-triazol-1-yl)propan-1-amine. HCl, the title compound was isolated, as a yellow solid in 45% yield (95% purity by HPLC).

MS(ESI+): 414.2; MS(ESI−): 412.3.

Example 54

4-pyrimidineacetonitrile, alpha-(3-bromo-2(1H)-pyridinylidene)-5-methyl-2-[[3-(3-oxo-4-morpholinyl)propyl]amino]-

Following the general methods as outlined in Example 1 (Method E), starting from 4-pyrimidineacetonitrile, alpha-(3-bromo-2(1H)-pyridinylidene)-2-chloro-5-methyl (intermediate 18), and 4-(3-aminopropyl)morpholin-3-one. HCl, the title compound was isolated, as a yellow solid in 47% yield (96% purity by HPLC).

MS(ESI+): 446.2; MS(ESI−): 444.3.

Example 55

4-pyrimidineacetonitrile, alpha-(3-bromo-2(1H)-pyridinylidene)-2-(cyclopentylamino)-5-methyl-

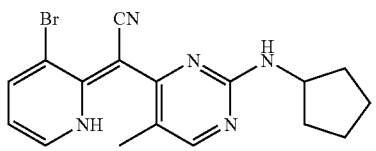

Following the general methods as outlined in Example 1 (Method E), starting from 4-pyrimidineacetonitrile, alpha-(3-bromo-2(1H)-pyridinylidene)-2-chloro-5-methyl (intermediate 18), and cyclopentylamine, the title compound was isolated, as a yellow solid in 60% yield (96% purity by HPLC).

MS(ESI$^+$): 373.2; MS(ESI$^-$): 371.3.

Example 56

4-pyrimidineacetonitrile, alpha-(3-bromo-2(1H)-pyridinylidene)-2-[[3-(2-oxo-1-pyrrolidinyl)propyl]amino]-

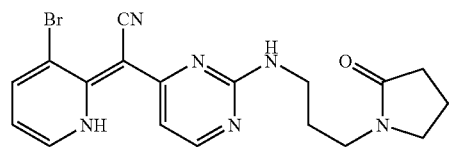

Following the general methods as outlined in Example 1 (Method E), starting from 4-pyrimidineacetonitrile, alpha-(3-bromo-2(1H)-pyridinylidene)-2-chloro- (intermediate 19), and N-(3'-aminopropyl)-2-pyrrolidinone, the title compound was isolated, as a yellow solid in 65% yield (99% purity by HPLC).

MS(ESI$^+$): 416.2; MS(ESI$^-$): 414.3.

Example 57

4-pyrimidineacetonitrile alpha-(3-bromo-2(1H)-pyridinylidene)-2-(cyclopentylamino)-

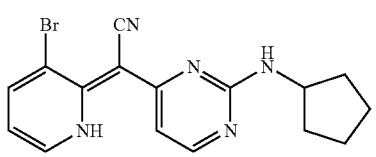

Following the general methods as outlined in Example 1 (Method E), starting from 4-pyrimidineacetonitrile, alpha-(3-bromo-2(1H)-pyridinylidene)-2-chloro- (intermediate 19), and cyclopentylamine, the title compound was isolated, as a yellow solid in 60% yield (96% purity by HPLC).

MS(ESI$^+$): 359.2; MS(ESI$^-$): 357.3.

Example 58

4-pyrimidineacetonitrile, alpha-(6-bromo-2(H)-pyridinylidene)-5-methyl-2-[[3-(1H-pyrazol-1-yl)propyl]amino]-

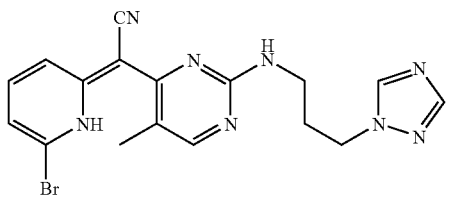

Following the general methods as outlined in Example 1 (Method E), starting from 4-pyrimidineacetonitrile, alpha-(6-bromo-2(1H)-pyridinylidene)-2-chloro-5-methyl (intermediate 15), and 3-(1H-1,2,4-triazol-1-yl)propan-1-amine. HCl, the title compound was isolated, as a yellow solid in 40% yield (95% purity by HPLC).

MS(ESI$^+$): 414.2; MS(ESI$^-$): 412.6.

Example 59

4-pyrimidineacetonitrile, alpha-(6-bromo-2(1H)-pyridinylidene)-5-methyl-2-[[3-(2-oxo-1-pyrrolidinyl)propyl]amino]-

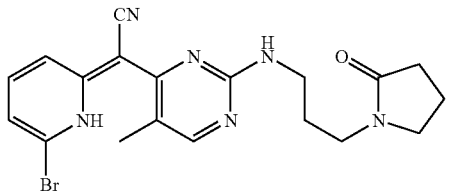

Following the general methods as outlined in Example 1 (Method E), starting from 4-pyrimidineacetonitrile, alpha-(6-bromo-2(1H)-pyridinylidene)-2-chloro-5-methyl (intermediate 15), and N-(3'-aminopropyl)-2-pyrrolidinone, the title compound was isolated, as a yellow solid in 42% yield (95% purity by HPLC).

MS(ESI$^+$): 430.3; MS(ESI$^-$): 428.6.

Example 60

4-pyrimidineacetonitrile alpha-(6-bromo-2(1H)-pyridinylidene)-2-(cyclopentylamino)-5-methyl-

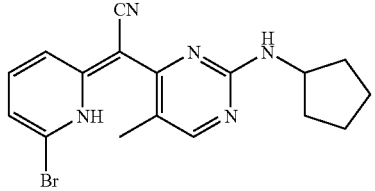

Following the general methods as outlined in Example 1 (Method E), starting from 4-pyrimidineacetonitrile, alpha-(6-bromo-2(1H)-pyridinylidene)-2-chloro-5-methyl (intermediate 15), and cyclopentylamine, the title compound was isolated, as a yellow solid in 42% yield (95% purity by HPLC).

MS(ESI$^+$): 373.4; MS(ESI$^-$): 371.4.

Example 61

4-pyrimidineacetonitrile, alpha-(6-bromo-2(1H)-pyridinylidene)-5-methyl-2-[[3-(3-oxo-4-morpholinyl)propyl]amino]-

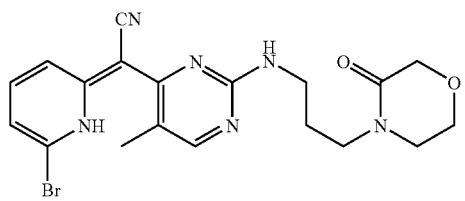

Following the general methods as outlined in Example 1 (Method E), starting from 4-pyrimidineacetonitrile, alpha-(6-bromo-2(1H)-pyridinylidene)-2-chloro-5-methyl (intermediate 15), and 4-(3-aminopropyl)morpholin-3-one. HCl, the title compound was isolated, as a yellow solid in 55% yield (95% purity by HPLC).

MS(ESI$^+$): 446.9; MS(ESI$^-$): 444.8.

Example 62

4-pyrimidineacetonitrile, alpha-(6-bromo-2(1H)-pyridinylidene)-5-methyl-2-[[3-(1H-1,2,4-triazol-1-yl)propyl]amino]-

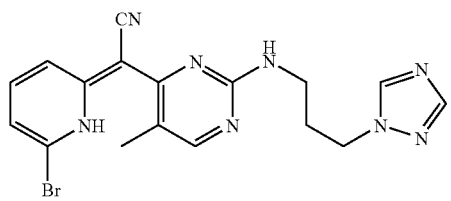

Following the general methods as outlined in Example 1 (Method E), starting from 4-pyrimidineacetonitrile, alpha-(6-bromo-2(1H)-pyridinylidene)-2-chloro-5-methyl (intermediate 15), and 3-(1H-1,2,4-triazol-1-yl)propan-1-amine. HCl, the title compound was isolated, as a yellow solid in 68% yield (94% purity by HPLC).

MS(ESI$^+$): 414.6; MS(ESI$^-$): 414.2.

Example 63

4-pyrimidineacetonitrile, alpha-(6-bromo-2(1H)-pyridinylidene)-5-methyl-2-[[2-(1H-1,2,4-triazol-1-yl)ethyl]amino]-

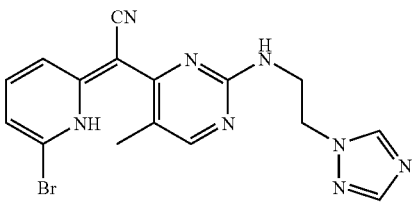

Following the general methods as outlined in Example 1 (Method E), starting from 4-pyrimidineacetonitrile, alpha-(6-bromo-2(1H)-pyridinylidene)-2-chloro-5-methyl (intermediate 15), and 2-(1,2,4-triazole-1-yl)-ethylamine, the title compound was isolated, as a yellow solid in 70% yield (92% purity by HPLC).

MS(ESI$^+$): 400.5; MS(ESI$^-$): 318.5.

Example 64

4-pyrimidineacetonitrile, 2-[[(1S,2S)-2-(phenylmethoxy)cyclopentyl]amino]-alpha-2(1H)-pyridinylidene-

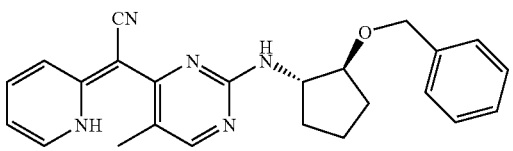

Following the general methods as outlined in Example 1 (Method E), starting from 4-pyrimidineacetonitrile, 2-chloro-5-methyl-alpha-2(1H)-pyridinylidene- (intermediate 5), and (1S,2S)-2-benzyloxycyclopentylamine, the title compound was isolated, as a yellow solid in 84% yield (98% purity by HPLC).

MS(ESI$^+$): 400.6; MS(ESI$^-$): 398.5.

Example 65

4-pyrimidineacetonitrile, 2-[[(1S,2S)-2-hydroxycyclohexyl]amino]-5-methyl-alpha-2(1H)-pyridinylidene-

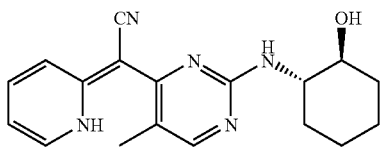

Following the general methods as outlined in Example 1 (Method E), starting from 4-pyrimidineacetonitrile, 2-chloro-5-methyl-alpha-2(1H)-pyridinylidene- (intermediate 5), and trans-2-aminocyclohexanol hydrochloride, the title compound was isolated, as a yellow solid in 80% yield (98% purity by HPLC).
MS(ESI$^+$): 324.6; MS(ESI$^-$): 322.2.

Example 66

4-pyrimidineacetonitrile, 2-[[2-(1H-imidazol-4-yl) ethyl]amino]-5-methyl-alpha-2(1H)-pyridinylidene-

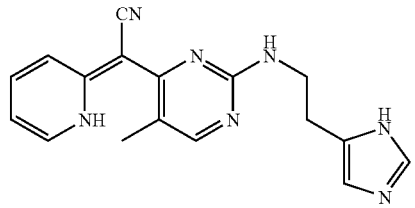

Following the general methods as outlined in Example 1 (Method E), starting from 4-pyrimidineacetonitrile, 2-chloro-5-methyl-alpha-2(1H)-pyridinylidene- (intermediate 5), and histamine, the title compound was isolated, as a yellow solid in 80% yield (98% purity by HPLC).
MS(ESI$^+$): 320.4; MS(ESI$^-$): 318.4.

Example 67

4-pyrimidineacetonitrile, 2-[[3-(2-oxo-1-pyrrolidinyl)propyl]amino]-alpha-2(1H)-pyridinylidene-

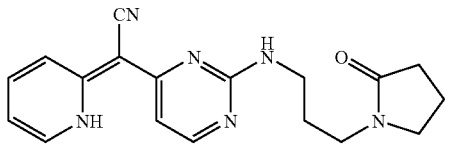

Following the general methods as outlined in Example 1 (Method E), starting from 4-pyrimidineacetonitrile, 2-chloro-5-methyl-alpha-2(1H)-pyridinylidene- (intermediate 5), and N-(3'-aminopropyl)-2-pyrrolidinone, the title compound was isolated, as a yellow solid in 72% yield (99% purity by HPLC).
MS(ESI$^+$): 337.4; MS(ESI$^-$): 335.2.

Example 68

4-pyrimidineacetonitrile, 2-[[(1S,2S)-2-hydroxycyclopentyl]amino]-alpha-2(1H)-pyridinylidene-

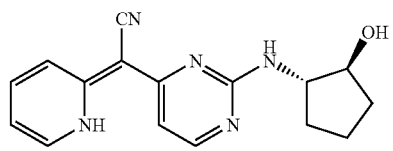

Following the general methods as outlined in Example 1 (Method E), starting from 4-pyrimidineacetonitrile, 2-chloro-5-methyl-alpha-2(1H)-pyridinylidene- (intermediate 5), and trans-2-aminocyclopentanol hydrochloride, the title compound was isolated, as a yellow solid in 78% yield (92% purity by HPLC).
MS(ESI$^+$): 296.4; MS(ESI$^-$): 294.8.

Example 69

4-pyrimidineacetonitrile, 2-(cycloheptylamino)-5-methyl-alpha-2(1H)-pyridinylidene-

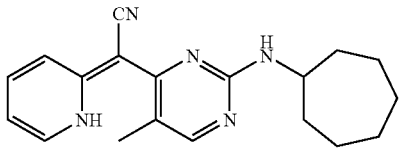

Following the general methods as outlined in Example 1 (Method E), starting from 4-pyrimidineacetonitrile, 2-chloro-5-methyl-alpha-2(1H)-pyridinylidene- (intermediate 5), and cycloheptylamine, the title compound was isolated, as a yellow solid in 70% yield (95% purity by HPLC).
MS(ESI$^+$): 322.4; MS(ESI$^-$): 320.4.

Example 70

4-pyrimidineacetonitrile, 5-methyl-alpha-2(1H)-pyridinylidene-2-[[3-(1H)-1,2,4-triazol-1-yl)propyl]amino]-

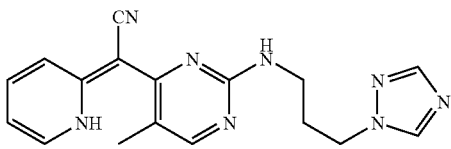

Following the general methods as outlined in Example 1 (Method E), starting from 4-pyrimidineacetonitrile, 2-chloro-5-methyl-alpha-2(1H)-pyridinylidene- (intermediate 5), and 3-(1H-1,2,4-triazol-1-yl)propan-1-amine. HCl, the title compound was isolated, as a yellow solid in 79% yield (96% purity by HPLC).
MS(ESI$^+$): 335.4; MS(ESI$^-$): 333.6.

Example 71

4-pyrimidineacetonitrile, 5-methyl-2-[[3-(3-oxo-4-morpholinyl)propyl]-amino]-alpha-2(1H)-pyridinylidene-

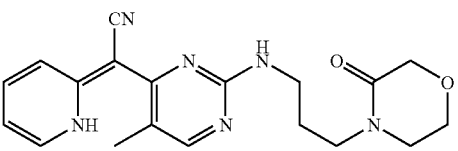

Following the general methods as outlined in Example 1 (Method E), starting from 4-pyrimidineacetonitrile, 2-chloro-5-methyl-alpha-2(1H)-pyridinylidene- (intermediate 5), and 4-(3-aminopropyl)morpholin-3-one. HCl, the title compound was isolated, as a yellow solid in 72% yield (94% purity by HPLC).

MS(ESI⁺): 366.4; MS(ESI⁻): 364.2.

Example 72

4-pyrimidineacetonitrile, 5-methyl-2-[[3-(1H-pyrazol-1-yl)propyl]amino]-alpha-2(1H)-pyridinylidene-

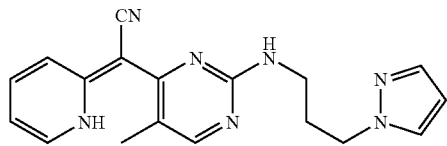

Following the general methods as outlined in Example 1 (Method E), starting from 4-pyrimidineacetonitrile, 2-chloro-5-methyl-alpha-2(1H)-pyridinylidene- (intermediate 5), and 3-(1H-pyrazol-1-yl)propan-1-amine. HCl, the title compound was isolated, as a yellow solid in 78% yield (92% purity by HPLC).

MS(ESI⁺): 334.4; MS(ESI⁻): 332.2.

Example 73

4-pyrimidineacetonitrile, 2-(cyclopentylamino-alpha-[6-(cyclopropylamino)-2(1H)-pyridinylidene]-5-methyl-

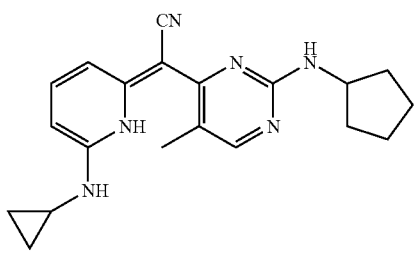

To a solution of 4-pyrimidineacetonitrile, alpha-(6-bromo-2(1H)-pyridinylidene)-2-(cyclopentylamino)-5-methyl- (example 60) (49 mg, 0.13 mmol, 1 eq) in 4 mL of dioxane purged with nitrogen were added tris(dibenzylideneacetone)dipalladium (0) (9 mg, 0.01 mmol, 0.08 eq), 1,3-bis(2,6-diisopropylphenyl)imidazolium chloride (7 mg, 0.02 mmol, 0.12 eq), potassium terbutoxide (28 mg, 0.25 mmol, 1.86 eq) and cyclopropylamine (31 mg, 0.53 mmol, 4 eq). The reaction mixture was heated up in a microwave tube at 120 degree for 12 minutes. The reaction mixture was filtered and washed with DCM. The DCM layer was washed three times with brine and dried over MgSO4, filtered and the organic was evaporated under vacuo. The residue was purified by reverse phase HPLC using a gradient 5% ACN to 100% ACN in 10 minutes. The expected product as TFA salt, was isolated as a yellow solid (25 mg, 0.071 mmol, yield: 55%, 98% HPLC purity)

MS(ESI⁺): 349.4; MS(ESI⁻): 347.9.

Example 74

4-pyrimidineacetonitrile, 2-(cyclopentylamino)-alpha-[6-(cyclopentylamino)-2(1H-pyridinylidene]-5-methyl-

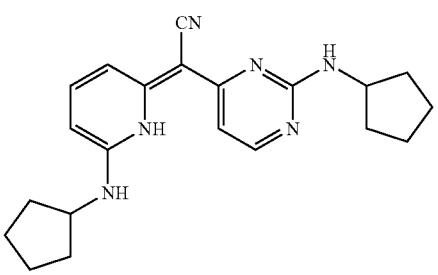

Following the general methods as outlined in Example 73, starting from 4-pyrimidineacetonitrile, alpha-(6-bromo-2(1H)-pyridinylidene)-2-(cyclopentylamino)-5-methyl- (example 60), and cyclopentylamine, the title compound was isolated, as a yellow solid in 44% yield (98% purity by HPLC).

MS(ESI⁺): 363.4; MS(ESI⁻): 361.2.

Example 75

4-pyrimidineacetonitrile, 2-(cyclopentylamino)-alpha-[6-(3 pyridinylamino)-2(1H)-pyridinylidene]-

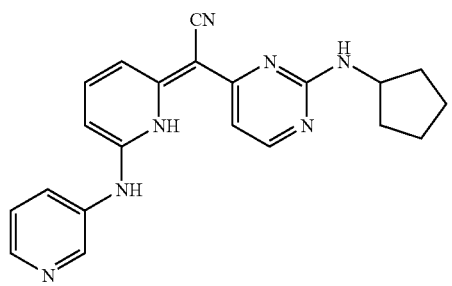

Following the general methods as outlined in Example 73, starting from 4-pyrimidineacetonitrile, alpha-(6-bromo-2(1H)-pyridinylidene)-2-(cyclopentylamino)-5-methyl- (example 60), and 3-aminopyridine, the title compound was isolated, as a yellow solid in 22% yield (92% purity by HPLC).

MS(ESI⁺): 372.4; MS(ESI⁻): 370.6.

Example 76

4-pyrimidineacetonitrile, 2-(cyclopentylamino)-alpha-[6-(2-pyridinylamino)-2(1H)-pyridinylidene]-

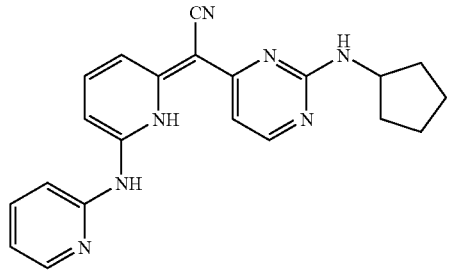

Following the general methods as outlined in Example 73, starting from 4-pyrimidineacetonitrile, alpha-(6-bromo-2(1H)-pyridinylidene)-2-(cyclopentylamino)-5-methyl- (example 60), and 2-aminopyridine, the title compound was isolated, as a yellow solid in 20% yield (94% purity by HPLC).

MS(ESI+): 372.6; MS(ESI−): 370.5.

Example 77

4-pyrimidineacetonitrile, 2-(cyclopentylamino)-5-methyl-alpha-[6-[methyl(phenylmethyl)amino]-2(1H)-pyridinylidene]-

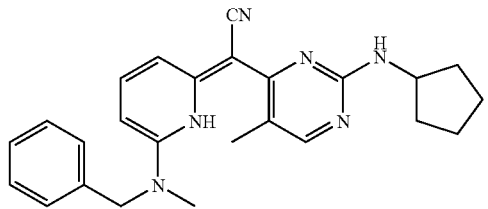

Following the general methods as outlined in Example 73, starting from 4-pyrimidineacetonitrile, alpha-(6-bromo-2(1H)-pyridinylidene)-2-(cyclopentylamino)-5-methyl- (example 60), and N-benzylmethylamine, the title compound was isolated, as a yellow solid in 36% yield (95% purity by HPLC).

MS(ESI+): 413.6; MS(ESI−): 411.3.

Example 78

4-pyrimidineacetonitrile, 2-(cyclopentylamino)-5-methyl-alpha-[6-([3-(2-oxo-1-pyrrolidinyl)propyl]amino]-2(1H)-pyridinylidene]-

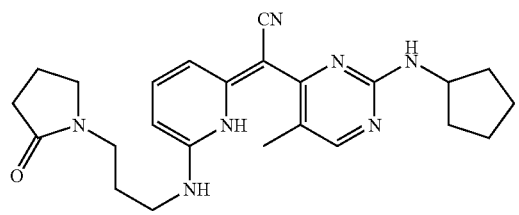

Following the general methods as outlined in Example 73, starting from 4-pyrimidineacetonitrile, alpha-(6-bromo-2(1H)-pyridinylidene)-2-(cyclopentylamino)-5-methyl- (example 60), and N-(3'-aminopropyl)-2-pyrrolidinone, the title compound was isolated, as a yellow solid in 32% yield (92% purity by HPLC).

MS(ESI+): 434.6; MS(ESI−): 432.5.

Example 79

4-pyrimidineacetonitrile, 2-(cyclopentylamino)-5-methyl-alpha-[6-(phenylamino)-2(1H)-pyridinylidene]-

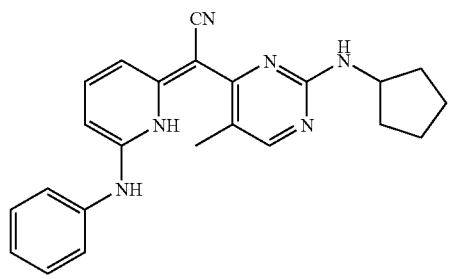

Following the general methods as outlined in Example 73, starting from 4-pyrimidineacetonitrile, alpha-(6-bromo-2(1H)-pyridinylidene)-2-(cyclopentylamino)-5-ethyl- (example 60), and aniline, the title compound was isolated, as a yellow solid in 40% yield (98% purity by HPLC).

MS(ESI+): 385.6; MS(ESI−): 383.5.

Example 80

4-pyrimidineacetonitrile, 2-(cyclopentylamino)-5-methyl-alpha-[6-(4-morpholinyl)-2(1H)-pyridinylidene]-

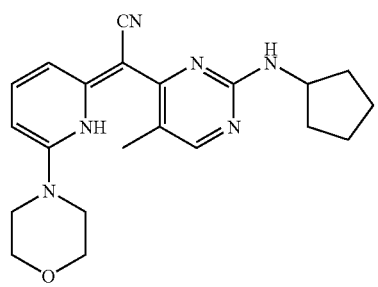

Following the general methods as outlined in Example 73, starting from 4-pyrimidineacetonitrile, alpha-(6-bromo-2(1H)-pyridinylidene)-2-(cyclopentylamino)-5-methyl- (example 60), and morpholine, the title compound was isolated, as a yellow solid in 33% yield (95% purity by HPLC).

MS(ESI+): 379.5; MS(ESI−): 377.5.

Example 81

4-pyrimidineacetonitrile, 2-(cyclopentylamino)-5-methyl-alpha-[6-[[2-(3-pyridinyl)ethyl]amino]-2(1H)-pyridinylidene]-

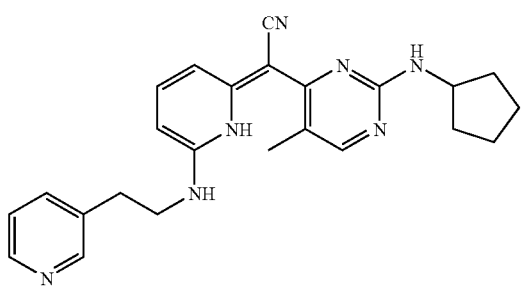

Following the general methods as outlined in Example 73, starting from 4-pyrimidineacetonitrile, alpha-(6-bromo-2(1H)-pyridinylidene)-2-(cyclopentylamino)-5-methyl- (example 60), and 2-(2-aminoethyl)pyridine, the title compound was isolated, as a yellow solid in 33% yield (95% purity by HPLC).

MS(ESI$^+$): 414.5; MS(ESI$^-$): 412.6.

Example 82

4-pyrimidineacetonitrile, alpha-(5-bromo-2(1H)-pyridinylidene)-2-(cyclopentylamino)-

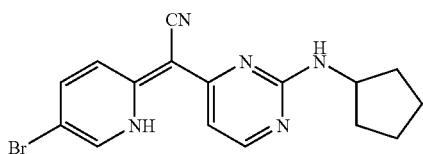

Following the general methods as outlined in Example 1 (Method E), starting from 4-pyrimidineacetonitrile, alpha-(5-bromo-2(1H)-pyridinylidene)-2-chloro-(intermediate 21), and cyclopentylamine, the title compound was isolated, as a yellow solid in 40% yield (98% purity by HPLC).

MS(ESI$^+$): 359.9; MS(ESI$^-$): 357.8.

Example 83

4-pyridineacetonitrile, 2-(cyclopentylamino-5-methyl-alpha-[6-[(trimethylsilyl)ethynyl]-2(1H)-pyridinylidene]-

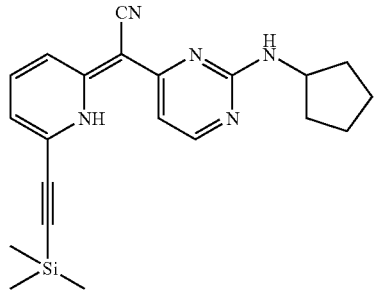

To a solution of 4-pyrimidineacetonitrile, alpha-(6-bromo-2(1H)-pyridinylidene)-2-(cyclopentylamino)- (80 mg, 0.22 mmol, 1 eq) in 4 mL of THF purged with nitrogen were added bis(triphenylphosphine)palladium(II)chloride (11, 0.02 mol, 0.07 q), Cuprous iodide (12, 0.06 mmol, 0.28 eq). The orange mixture was stirred for 5 minutes under nitrogen at room temperature. To this solution was added trimethylsilylacetylene (26 mg, 0.26 mmol, 1.2 eq) followed by diisopropylamine (2 mL). The reaction mixture was stirred at room temperature for 2 days. The mixture was filtered and the filtrate added to 5 mL of water and extracted with DCM three times. The organic layer was washed with KOH1M, water and brine and dried over MgSO4, filtered and evaporated. The residue was purified by flash chromatography CycloH:EtOAc (8:2) to give the expected product as a yellow solid (28 mg, 0.071 mmol, yield: 32%, HPLC purity 95%).

MS(ESI$^+$): 376.9; MS(ESI$^-$): 374.6.

Example 84

4-pyrimidineacetonitrile, alpha-[3-(3-hydroxy-3-methyl-1-butynyl)-2(1H)-pyridinylidene]-5-methyl-2-[[3-(3-oxo-4-morpholinyl)propyl]amino]-

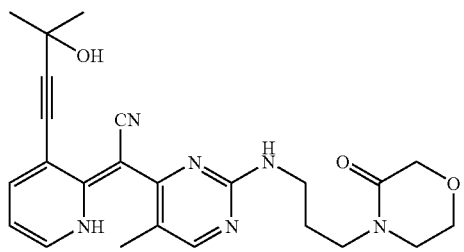

Following the general methods as outlined in Example 73, starting from 4-pyrimidineacetonitrile, alpha-(3-bromo-2(1H)-pyridinylidene)-5-methyl-2-[[3-(3-oxo-4-morpholinyl)propyl]amino]-, and 2-methyl-3-butyn-2-ol, the title compound was isolated, as a yellow solid in 30% yield (93% purity by HPLC).

MS(ESI$^+$): 449.6; MS(ESI$^-$): 447.3.

Example 85

Preparation of a Pharmaceutical Formulation

The following formulation examples illustrate representative pharmaceutical compositions according to the present invention being not restricted thereto.

Formulation 1—Tablets

A pyridinyl acetonitrile of formula I is admixed as a dry powder with a dry gelatin binder in an approximate 1:2 weight ration. A minor amount of magnesium stearate is added as a lubricant. The mixture is formed into 240-270 mg tablets (80-90 mg of active pyridinyl acetonitrile compound per tablet) in a tablet press.

Formulation 2—Capsules

A pyridinyl acetonitrile of formula I is admixed as a dry powder with a starch diluent in an approximate 1:1 weight ratio. The mixture is filled into 250 mg capsules (125 mg of active pyridinyl acetonitrile compound per capsule).

Formulation 3—Liquid

A pyridinyl acetonitrile of formula I (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A pyridinyl acetonitrile of formula I is admixed as a dry powder with a dry gelatin binder in an approximate 1:2 weight ratio. A minor amount of magnesium stearate is added as a lubricant. The mixture is formed into 450-900 mg tablets (150-300 mg of active pyridinyl acetonitrile compound) in a tablet press.

Formulation 5—Injection

A pyridinyl acetonitrile of formula (I) is dissolved in a buffered sterile saline injectable aqueous medium to a concentration of approximately 5 mg/ml.

Biological Assays

The compounds of the present invention may be subjected to the following assays:

a) JNK2 and -3 In Vitro Assay:

The compounds of the present invention are inhibitors of JNKs. The phosphorylation of c-jun by JNK2 or JNK3 may be determined by monitoring the incorporation of $^{33}P$ into c-jun following the protocol below. The inhibitory activity of the compounds according to formula I, towards c-jun phosphorylation through JNK, is determined by calculating phosphorylation activity in the presence or absence of compounds according to formula I.

JNK3 and/or -2 assays are performed in 96 well MIT plates: incubation of 0.5 μg of recombinant, pre-activated GST-JNK3 or GST-JNK2 with 1 μg of recombinant, biotinylated GST-c-Jun and 2 μM $^{33}$γ-ATP (2 nCi/μl), in the presence or absence of compounds according to formula I and in a reaction volume of 50 μl containing 50 mM Tris-HCl, pH 8.0; 10 mM $MgCl_2$; 1 mM Dithiothreitol, and 100 μM $NaVO_4$. The incubation is performed for 120 min. at R.T and stopped upon addition of 200 μl of a solution containing 250 μg of Streptavidine-coated SPA beads (Amersham, Inc.)*, 5 mM EDTA, 0.1% Triton X-100 and 50 μM ATP, in phosphate saline buffer.

After incubation for 60 minutes at RT, beads are sedimented by centrifugation at 1500×g for 5 minutes, resuspended in 200 μl of PBS containing 5 mM EDTA, 0.1% Triton X-100 and 50 μM ATP and the radioactivity measured in a scintillation β counter, following sedimentation of the beads as described above.

The tested compounds according to formula I display an inhibition ($IC_{50}$) with regard to JNK3 of less than 20 μM, preferably less than 1 μM.

b) GSK3 In Vitro Assay:

GSK3β Assay (see *Bioorg. Med. Chem. Lett* by Naerum et al. 12 p. 1525-1528 (2002))

In a final reaction volume of 25 μl, GSK3β (h) (5-10 mU) is incubated with 8 mM MOPS pH 7.0, 0.2 mM EDTA, 20 μM YRRAAVPPSPSLSRHSSPHQS(p)EDEEE (being the GSK3 substrate; a phospho GS2 peptide), 10 mM Mg Acetate and [γ-$^{33}$P-ATP] (Specific activity approx. 500 cpm/pmol, concentration as required). The reaction is initiated by the addition of $Mg^{2+}$ [γ-$^{33}$P-ATP]. After incubation for 40 minutes at room temperature, the reaction is stopped by the addition of 5 μl of a 3% phosphoric acid solution. 10 μl of the reaction is then spotted onto a P30 filtermat and washed three times for 5 minutes in 50 mM phosphoric acid and once in methanol prior to drying and the degree of phosphorylation of the substrate is determined by scintillation counting.

The tested compounds according to formula I display an inhibition ($IC_{50}$) with regard to GSK3 of less than 20 μM, preferably less than 10 and even more preferred less than 1 μM.

The binding affinities of the compounds of formula (I) were assessed using the above described in vitro biological assay. Representative values for some example compounds are given in Tables 1 and 2 below.

The values in Table 1 refer to the binding affinity ($IC_{50}$; μM) of the example compounds according to formula I to GSK3.

TABLE 1

In vitro potency of pyridinyl derivatives on human GSK3 beta

| Structure | Compound | $IC_{50}$ (μM) GSK3beta |
|---|---|---|
| (structure with CN, pyridinyl, pyrimidinyl, methylbutylamino groups) | {5-methyl-2-[(1-methylbutyl)amino]-4-pyrimidinyl}(2-pyridinyl)-acetonitrile | 0.17 |
| (structure with CN, pyridinyl, pyrimidinyl, cyclopropylamino groups) | [2-(cyclopropylamino)-5-methyl-4-pyrimidinyl](2-pyridinyl)acetonitrile | 0.2 |
| (structure with CN, pyridinyl, pyrimidinyl, 2-(3-pyridinyl)ethylamino groups) | (5-methyl-2-{[2-(3-pyridinyl)ethyl]amino}-4-pyrimidinyl)(2-pyridinyl)-acetonitrile | 0.5 |

TABLE 1-continued

In vitro potency of pyridinyl derivatives on human GSK3 beta

| Structure | Compound | IC$_{50}$ (μM) GSK3beta |
|---|---|---|
| 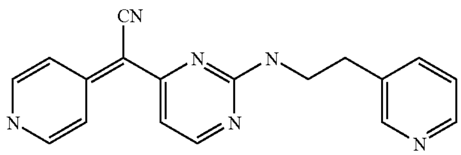 | 4-pyridinyl(2-{[2-(3-pyridinyl)ethyl]-amino}-4-pyrimidinyl)acetonitrile | 1.5 |
| 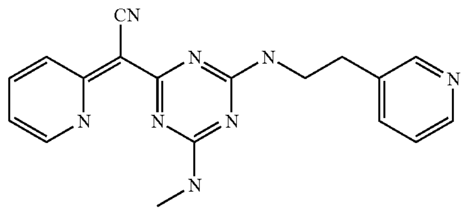 | (4-(methylamino)-6-{[2-(3-pyridinyl)ethyl]-amino}-1,3,5-triazin-2-yl)(2-pyridinyl)acetonitrile | 7.7 |
| 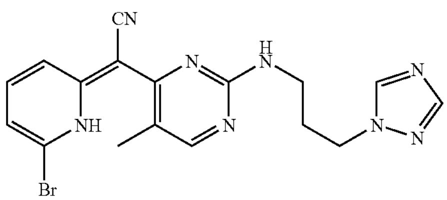 | 4-pyrimidineacetonitrile, alpha-(6-bromo-2(1H)-pyridinylidene)-5-methyl-2-[[3-(1H-pyrazol-1-yl)propyl]amino]- | 0.008 |

The values in Table 2 refer to the binding affinity (IC$_{50}$; μM) of the example compounds according to formula I to JNK3.

TABLE 2

In vitro potency of pyridinyl derivatives on rat JNK3

| Structure | IUPAC-Name | JUNK3 IC50 (μM) |
|---|---|---|
| 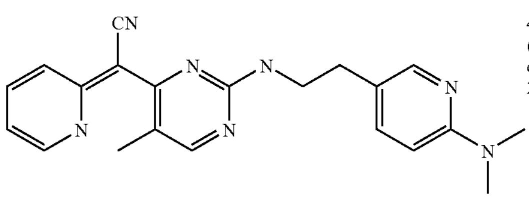 | 4-pyrimidineacetonitrile, 2-[[2-[6-(dimethylamino)-3-pyridinyl]-ethyl]amino]-5-methyl-alpha-2(1H)-pyridinylidene- | 0.48 |
| 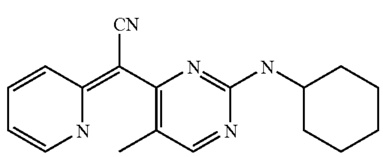 | 4-pyrimidineacetonitrile, 2-(cyclohexylamino)-5-methyl-alpha-2-pyridinyl- | 0.07 |
| 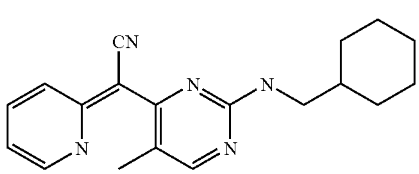 | 4-pyrimidineacetonitrile, 2-[(cyclohexylmethyl)amino]-5-methyl-alpha-2-pyridinyl- | 0.486 |

TABLE 2-continued

In vitro potency of pyridinyl derivatives on rat JNK3

| Structure | IUPAC-Name | JUNK3 IC50 (μM) |
|---|---|---|
| 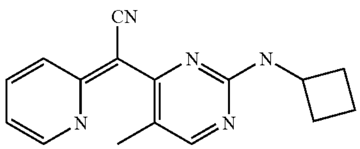 | 4-pyrimidineacetonitrile, 2-(cyclobutylamino)-5-methyl-alpha-2(1H)-pyridinylidene- | 0.106 |
| 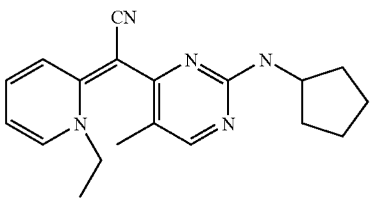 | 4-pyrimidineacetonitrile, 2-(cyclopentylamino)-alpha-(1-ethyl-2(1H)-pyridinylidene)-5-methyl- | 6.2 |
| 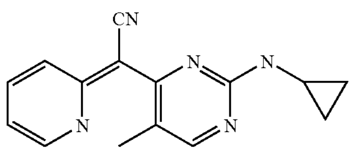 | 4-pyrimidineacetonitrile, 2-(cyclopropylamino)-5-methyl-alpha-2-pyridinyl- | 0.299 |
| 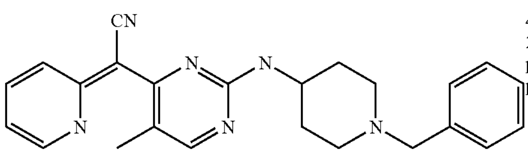 | 4-pyrimidineacetonitrile, 5-methyl-2-[[1-(phenylmethyl)-4-piperidinyl]amino]-alpha-2(1H)-pyridinylidene- | 0.665 |
| 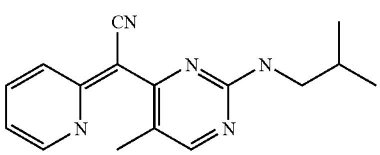 | 4-pyrimidineacetonitrile, 5-methyl-2-[(2-methylpropyl)amino]-alpha-2(1H)-pyridinylidene- | 0.21 |
| 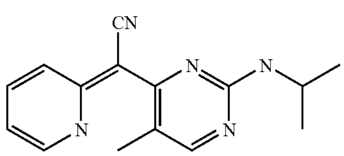 | 4-pyrimidineacetonitrile, 5-methyl-2-[(1-methylethyl)amino]-alpha-2(1H)-pyridinylidene- | 0.31 |
| | 4-pyrimidineacetonitrile, 2-[[(1S,2S)-2-hydroxycyclohexyl]amino]-5-methyl-alpha-2(1H)-pyridinylidene- | 0.74 |
| | 1-piperidinecarboxylic acid, 4-[[4-[(E)-cyano-2(1H)-pyridinylidenemethyl]-5-methyl-2-pyrimidinyl]amino]-, 1,1-dimethylethyl ester | 1.14 |

TABLE 2-continued

In vitro potency of pyridinyl derivatives on rat JNK3

| Structure | IUPAC-Name | JUNK3 IC50 (μM) |
|---|---|---|
| 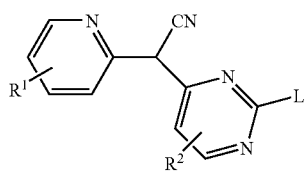 | 4-pyrimidineacetonitrile, 2-chloro-5-methyl-alpha-2(1H)-pyridinylidene- | 2.35 |

REFERENCE LIST

1. Woodgett et al: *Trends Biochem. Sci.,* 16 p. 177-81 (1991);
2. Lovestone et al., *Current Biology* 4 p. 1077-86 (1994);
3. Brownlees et al., *Neuroreport* 8 p. 3251-55 (1997);
4. Takashima et al., *PNAS* 95 p. 9637-41 (1998)
5. Zhong et al. *Nature* 395 p. 698-702 (1998);
6. Takashima et al., *PNAS* 90 p. 7789-93 (1993);
7. Pei et al., *J. Neuropathol. Exp.* 56 p. 70-78 (1997);
8. *J. Neurochemistry* 72 p. 1327-30 (1999);
9. Nonaka et al. *PNAS* 95 p. 2642-47 (1998);
10. Thomas et al., *J. Am. Geriatr. Soc.* 43 p. 1279-89 (1995);
11. Sasaki C. et al., *Neurol. Res.* 23(6) p. 588-92 (2001)
12. Darren A. E. et al. *Journal of Neurochemistry* 77 p. 94-102 (2001);
13. A. Ali et al., *Chem. Rev.* p. A-N (December 2000);
14. EP-752,424;
15. EP-461,079.
16. WO 01/47920

The invention claimed is:

1. A compound of formula (Ib) in all tautomeric forms:

(Ib)

wherein

L is selected from the group consisting of sulfonyl, amino, $C_1$-$C_6$-alkyl, $C_2$-$C_6$-alkenyl, $C_2$-$C_6$-alkynyl, aryl, heteroaryl, saturated 3-8-membered cycloalkyl, unsaturated 3-8-membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, $C_2$-$C_6$-alkynyl heterocycloalkyl, alkoxycarbonyl, aminocarbonyl, $C_1$-$C_6$-alkyl carboxy, $C_1$-$C_6$-alkyl acyl, aryl acyl, heteroaryl acyl, $C_3$-$C_8$-(hetero)cycloalkyl acyl, $C_1$-$C_6$-alkyl acyloxy, $C_1$-$C_6$-alkyl alkoxy, $C_1$-$C_6$-alkyl alkoxycarbonyl, $C_1$-$C_6$-alkyl aminocarbonyl, $C_1$-$C_6$-alkyl acylamino, acylamino, $C_1$-$C_6$-alkyl ureido, $C_1$-$C_6$-alkyl carbamate, $C_1$-$C_6$-alkyl amino, $C_1$-$C_6$-alkyl ammonium, $C_1$-$C_6$-alkyl sulfonyloxy, $C_1$-$C_6$-alkyl sulfonyl, $C_1$-$C_6$-alkyl sulfinyl, $C_1$-$C_6$-alkyl sulfanyl, $C_1$-$C_6$-alkyl sulfonylamino, $C_1$-$C_6$-alkyl aminosulfonyl, hydroxy, halogen, and cyano, $R^1$ is a hydrogen, a sulfonyl, amino, a $C_1$-$C_6$-alkyl, a $C_2$-$C_6$-alkenyl, a $C_2$-$C_6$-alkynyl, an aryl or a $C_1$-$C_6$-alkoxy, a halogen, a cyano or a hydroxy, $R^2$ is a hydrogen, a sulfonyl, amino, a $C_1$-$C_6$-alkyl, a $C_2$-$C_6$-alkenyl, a $C_2$-$C_6$-alkynyl or a $C_1$-$C_6$-alkoxy, a halogen, a cyano or a hydroxyl, wherein heteroaryl is optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl;

sulfonyl is —$SO_2$—R wherein R is H, aryl, heteroaryl, $C_1$-$C_6$-alkyl, $C_1$-$C_6$-alkyl substituted with a halogen, $C_2$-$C_6$-alkenyl, $C_2$-$C_6$-alkynyl, $C_3$-$C_8$-cycloalkyl, heterocycloalkyl, aryl, heteroaryl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynylheteroaryl, $C_1$-$C_6$-alkyl cycloalkyl, or $C_1$-$C_6$-alkyl heterocycloalkyl;

acyl is —C(O)R where R is H, $C_1$-$C_6$-alkyl, $C_2$-$C_6$-alkenyl, $C_2$-$C_6$-alkynyl, $C_3$-$C_8$-cycloalkyl, heterocycloalkyl, aryl, heteroaryl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynylheteroaryl, $C_1$-$C_6$-alkyl cycloalkyl, or $C_1$-$C_6$-alkyl heterocycloalkyl; and heterocycloalkyl is pyrrolidine, piperidine, piperazine, 1-methylpiperazine, or morpholine.

2. A compound of formula (Ic) in all tautomeric forms:

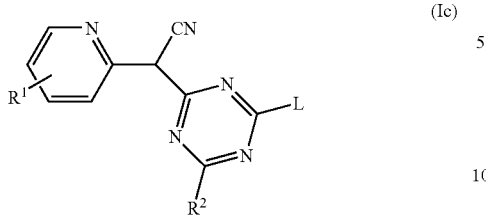

wherein

L is selected from the group consisting of sulfonyl, amino, $C_1$-$C_6$-alkyl, $C_2$-$C_6$-alkenyl, $C_2$-$C_6$-alkynyl, aryl, heteroaryl, saturated 3-8-membered cycloalkyl, unsaturated 3-8-membered cycloalkyl, 3-8-membered heterocycloalkyl, an acyl moiety, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynyl heteroaryl, $C_1$-$C_6$-alkyl cycloalkyl, $C_1$-$C_6$-alkyl heterocycloalkyl, $C_2$-$C_6$-alkenyl cycloalkyl, $C_2$-$C_6$-alkenyl heterocycloalkyl, $C_2$-$C_6$-alkynyl cycloalkyl, $C_2$-$C_6$-alkynyl heterocycloalkyl, alkoxycarbonyl, aminocarbonyl, $C_1$-$C_6$-alkyl carboxy, C-$C_6$-alkyl acyl, aryl acyl, heteroaryl acyl, $C_3$-$C_8$-(hetero)cycloalkyl acyl, $C_1$-$C_6$-alkyl acyloxy, $C_1$-$C_6$-alkyl alkoxy, $C_1$-$C_6$-alkyl alkoxycarbonyl, $C_1$-$C_6$-alkyl aminocarbonyl, $C_1$-$C_6$-alkyl acylamino, acylamino, $C_1$-$C_6$-alkyl ureido, $C_1$-$C_6$-alkyl carbamate, $C_1$-$C_6$-alkyl amino, $C_1$-$C_6$-alkyl ammonium, $C_1$-$C_6$-alkyl sulfonyloxy, $C_1$-$C_6$-alkyl sulfonyl, $C_1$-$C_6$-alkyl sulfinyl, $C_1$-$C_6$-alkyl sulfanyl, $C_1$-$C_6$-alkyl sulfonylamino, $C_1$-$C_6$-alkyl aminosulfonyl, hydroxy, halogen, and cyano, $R^1$ is a hydrogen, a sulfonyl, amino, a $C_1$-$C_6$-alkyl, a $C_2$-$C_6$-alkenyl, a $C_2$-$C_6$-alkynyl, an aryl or a $C_1$-$C_6$-alkoxy, a halogen, a cyano or a hydroxy, $R^2$ is a hydrogen, a sulfonyl, amino, a $C_1$-$C_6$-alkyl, a $C_2$-$C_6$-alkenyl, a $C_2$-$C_6$-alkynyl or a $C_1$-$C_6$-alkoxy, a halogen, a cyano or a hydroxyl wherein heteroaryl is optionally substituted pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl,1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b ]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl;

sulfonyl is —$SO_2$—R wherein R is H, aryl, heteroaryl, $C_1$-$C_6$-alkyl, $C_1$-$C_6$-alkyl substituted with a halogen, $C_2$-$C_6$-alkenyl, $C_2$-$C_o$-alkynyl, $C_3$-$C_8$-cycloalkyl, heterocycloalkyl, aryl, heteroaryl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynylheteroaryl, $C_1$-$C_6$-alkyl cycloalkyl, or $C_1$-$C_6$-alkyl heterocycloalkyl;

acyl is —C(O)R where R is H, $C_1$-$C_6$-alkyl, $C_2$-$C_6$-alkenyl, $C_2$-$C_6$-alkynyl, $C_3$-$C_8$-cycloalkyl, heterocycloalkyl, aryl, heteroaryl, $C_1$-$C_6$-alkyl aryl, $C_1$-$C_6$-alkyl heteroaryl, $C_2$-$C_6$-alkenyl aryl, $C_2$-$C_6$-alkenyl heteroaryl, $C_2$-$C_6$-alkynyl aryl, $C_2$-$C_6$-alkynylheteroaryl, $C_1$-$C_6$-alkyl cycloalkyl, or $C_1$-$C_6$-alkyl heterocycloalkyl; and heterocycloalkyl is pyrrolidine, piperidine, piperazine, 1-methylpiperazine, or morpholine.

3. The compound according to claim 1, wherein $R^1$ and $R^2$ are each independently H or $C_1$-$C_3$ alkyl.

4. The compound according to claim 1, which -selected from the group consisting of:

2-[[1-(diphenylmethyl)-3-azetidinyl]amino]-5-methyl-alpha-2(1H)-pyridinylidene-4-pyrimidineacetonitrile, 5-methyl-2-[[2-(3-pyridinyl)ethyl]amino]-alpha-2(1 H)-pyridinylidene-4-pyrimidineacetonitrile, 2-[[2- [6-(dimethylamino)-3-pyridinyl]ethyl]amino]-5-methyl-alpha-2(1 H) pyridinylidene-4-pyrimidineacetonitrile, 5-methyl-2-[[3-(2-oxo-1-pyrrolidinyl)propyl]amino]-alpha-2(1 H)-pyridinylidene-4-pyrimidineacetonitrile, 5-methyl-alpha-2-pyridinyl-2-[[2-(2-pyridinyl)-ethyl]amino]-4 pyrimidineacetonitrile, 2-(cyclopentylamino)-5-methyl-alpha-(6-phenyl-2(1H)-pyridinylidene)-4-pyrimidineacetonitrile,
2

5-methyl-2-(4-piperidinylamino)-alpha-2 (1 H)-pyridinylidene-4-pyrimidineacetonitrile, 2-(cyclohexylamino)-5-methyl-alpha-2-pyridinyl-4-pyrimidineacetonitrile, 2-[(cyclohexylmethyl)amino]-5-methyl-alpha-2-pyridinyl-4-pyrimidineacetonitrile, 2-(cyclopentylamino)-5-methyl-alpha-2-pyridinyl-4-pyrimidineacetonitrile, 2- [(3-hydroxy- 1-phenylpropyl)amino]-5-methyl-alpha-2(1 H)-pyridinylidene-4-pyrimidineacetonitrile, 2-(cyclobutylamino)-5-methyl-alpha-2(1 H)-pyridinylidene-4-pyrimidineacetonitrile, 2-(cyclopentylamino)-alpha-(1-ethyl-2(1 H)-pyridinylidene)-5-methyl-4-pyrimidineacetonitrile, 2-(cyclopropylamino)-5-methyl-alpha-2-pyridinyl-4-pyrimidineacetonitrile, 5-methyl-2-[[1-(phenylmethyl)-4-piperidinyl]amino]-alpha-2(1 H)-pyridinylidene-4-pyrimidineacetonitrile, 2-[(1 ethylpropyl)amino]-5-methyl-alpha-2(1 H)-pyridinylidene-4-pyrimidineacetonitrile, 5-methyl-alpha-2(1 H)-pyridinylidene-2- [[(tetrahydro-2H-pyran-4-yl)methyl]amino]-4-pyrimidineacetonitrile, 5-methyl-alpha-2(1 H)-pyridinylidene-2- [[(tetrahydro-2-furanyl)methyl]amino]-4-pyrimidineacetonitrile, 5-methyl-2-[(2-methylpropyl)amino]-alpha-2(1 H)-pyridinylidene-4-pyrimidineacetonitrile, 5-methyl-2-[(1 methylethyl)amino]-alpha-2(1 H)-pyridinylidene-4-pyrimidineacetonitrile, 2-[[(1 S ,2S)-2-hydroxycyclohexyl]amino]-5-methyl-alpha-2(1 H)-pyridinylidene-4-pyrimidineacetonitrile, 2-[[(1 S,2S)-2-hydroxycyclopentyl]amino]-5-methyl-alpha-2(1 H)-pyridinylidene-4-pyrimidineacetonitrile, 2-[(trans-4-hydroxycyclohexyl)amino]-5-methyl-alpha-2 (1H)-pyridinylidene-1-piperidinecarboxylic acid, 4-[[4-[(E)-cyano-2(1H)-pyridinylidenemethyl]-5-methyl-2-pyrimidinyl]amino]-1,1 dimethylethyl ester 4-pyrimidineacetonitrile, 5-methyl-2-[(1-methylbutyl)amino]-alpha-2-pyridinyl-4-pyrimidineacetonitrile, 2-(cyclopentylamino)-alpha-2-pyridinyl-4-pyrimidineacetonitrile, 2-(cyclohexylamino)-alpha-2-pyridinyl-4-pyrimidineacetonitrile,
5-methyl-alpha-2-pyridinyl-2-[4-(2-pyrimidinylamino)-1-piperidinyl]-4-pyrimidineacetonitrile,
alpha-2-pyridinyl-2-[[2-(3 pyridinyl)ethyl]amino]-4-pyrimidineacetonitrite,
2-(cyclopropylamino)-alpha-2-pyridinyl-benzoic acid,
4-[2-[[4-(cyano-2-pyridinylmethyl)-5methyl-2-pyrimidinyl]amino]ethyl]-methyl ester 4-pyrimidineacetonitrile,
2-[(1,2-dimethylpropyl)amino]-5-methyl-alpha-2-pyridinyl-4-pyrimidineacetonitrile,
2-[(2,3-dimethylcyclohexyl)amino]-5-methyl-alpha-2-pyridinyl-4-pyrimidineacetonitrile,
alpha-4-pyridinyl-2- [[2-(3-pyridinyl)ethyl]amino]-4-pyrimidineacetonitrile,
2-[(2furanylmethyl)amino]-5-methyl-alpha-2-pyridinyl-4-pyrimidineacetonitrile,
2-[(1-methylbutypamino]-alpha-2-pyridinyl-4-pyrimidineacetonitrile,
5-methyl-2-[[2-(1H-pyrazol-1yl)ethyl]amino]-alpha-2-pyridinyl-4-pyrimidineacetonitrile,
2-[[2(4aminophenyl)ethyl]amino]-5-methyl-alpha-2-pyridinyl-4-pyrimidineacetonitrile,
2- [[(4-methoxyphenyl)ethyl]amino]-5-methyl-alpha-2-pyridinyl-4-pyrimidineacetonitrile,
6-(cyclopentylamino)-alpha-2-pyridinyl-4-pyrimidineacetonitrile,
alpha-2-pyridinyl-2-[[2(2pyridinyl)ethyl]amino]-4-pyrimidineacetonitrile,
2-4-ethyl-1-piperazinyl)-6-methyl-alpha-2-pyridinyl-4-pyrimidineacetonitrile,
2-(cyclopentylamino)-alpha-4-pyridinyl-4-pyrimidineacetonitrile,
2- [[[4-(difluoromethoxy)phenyl]methyl]amino]-alpha-2-pyridinyl-4-pyrimidineacetonitrile,
2-[(2,3dimethylcyclohexyl)amino]-alpha-2-pyridinyl-4-pyrimidineacetonitrile,
6-methyl-2-[(1-methylbutypamino]-alpha-2-pyridinyl-4-pyrimidineacetonitrile,
2-[(2-furanylmethyl)amino]-alpha-2-pyridinyl-4-pyrimidineacetonitrile,
2-(cyclopentylamino)-6-methyl-alpha-2-pyridinyl-1,3,5-triazine-2-acetonitrile, 4-(methylamino)-alpha-2-pyridinyl-6-[[2-(3pyridinyl)ethyl]amino]-4-pyrimidineacetonitrile,
2-[[2-[6-(dimethylamino)-3-pyridinyl]ethyl]amino]-alpha-2-pyridinyl-4-pyrimidineacetonitrile,
2-(dipropylamino)-5-methyl-alpha-2-pyridinyl-4-pyrimidineacetonitrile,
alpha-2-pyridinyl-6-[[2-(3-pyridinyl)ethyl]amino]-4-pyrimidineacetonitrile,
alpha-(3-bromo-2(1H)-pyridinylidene)-2-(cyclopentylamino)-4-pyrimidineacetonitrile,
alpha-(6-bromo-2(1H)-pyridinylidene)-5-methyl-2-[[3-(1 H-pyrazol -1 yl)propyl]amino]-4-pyrimidineacetonitrile,
alpha-(6-bromo-2(1 H)-pyridinylidene)-5-methyl-2-[[3-(2-oxo-1 pyrrolidinyl)propyl]amino]-4-pyrimidineacetonitrile,
alpha-(6-bromo-2(1H)-pyridinylidene)-2-(cyclopentylamino)-5-methyl-4-pyrimidineacetonitrile,
alpha-(6-bromo-2(1H)-pyridinylidene)-2-(cyclopentylamino)-4-pyrimidineacetonitrile,
alpha-(6-bromo-2(1 H)-pyridinylidene)-5-methyl-2-[[3-(3-oxo-4 morpholinyl)propyl]amino]-4-pyrimidineacetonitrile,
2-(cyclopentylamino)-alpha-[6-(cyclopropylamino)-2(1H)-pyridinylidene]-5methyl -4-pyrimidineacetonitrile,
alpha-(6-bromo-2(1H)-pyridinylidene)-5-methyl-2-[[3-(1H-1,2,4-triazol- 1-yl)propyl]amino]-4-pyrimidineacetonitrile,
alpha-(3-bromo-2(1H)-pyridinylidene)-2-[[3-(2-oxo-1-pyrrolidinyl)propyl]amino]-4-pyrimidineacetonitrile,
2-(cyclopentylamino)-5-methyl-alpha-[6-(phenylamino)-2(1 H)-pyridinylidene]-4-pyrimidineacetonitrile,
5-methyl-2-[[3-(1 H-pyrazol- 1-yl)propyl]amino]-alpha-2(1 H)-pyridinylidene-4-pyrimidineacetonitrile,
alpha-(6-bromo-2(1 H)-pyridinylidene)-2-[[3-(1H-1 ,2,4-triazol- 1-yl)propyl]amino]-4-pyrimidineacetonitrile,
5-methyl-2-[[3-(3-oxo-4-morpholinyl)propyl]amino]-alpha-2(1 H)-pyridinylidene-4-pyrimidineacetonitrile,
2-(cycloheptylamino)-5-methyl-alpha-2(1 H)-pyridinylidene-4-pyrimidineacetonitrile,
alpha-(6-bromo-2(1 H)-pyridinylidene)-2-[[2-(1 H-1,2,4-triazol- 1yl)ethyl]amino]-4-pyrimidineacetonitrile,
5-methyl-alpha-2(1 H)-pyridinylidene-2-[[3-(1H-1,2,4-triazol- 1-yl)propyl]amino]-4-pyrimidineacetonitrile,
alpha-(5-bromo-2(1H)-pyridinylidene)-2-(cyclopentylamino)-4-pyrimidineacetonitrile,
2- [[3-(1 H-pyrazol- 1-yl)propyl]amino]-alpha- 6-[[3-(1 H-pyrazol- 1-yl)propyl]amino]2(1 H)-pyridinylidene]-4-pyrimidineacetonitrile,
2-(cycloheptylamino)-alpha-2(1H)-pyridinylidene-4-pyrimidineacetonitrile,
alpha-(6-bromo-2(1 H)-pyridinylidene)-5-methyl-2-[[2-(1 H-1 ,2,4-triazol- 1-yl)ethyl]amino]-4-pyrimidineacetonitrile,
2-(cyclopentylamino)-5-methyl-alpha-[6-(4-morpholinyl)-2(1 H)-pyridinylidene]-4-pyrimidineacetonitrile,
2-[[(1 S,2S)-2-hydroxycyclopentyl]amino]-alpha-2(1H)-pyridinylidene-4-pyrimidineacetonitrile,
alpha-(3-bromo-2(1H)-pyridinylidene)-2-(cyclopentylamino)-5-methyl-4-pyrimidineacetonitrile,
2-[[3-(2-oxo-1-pyrrolidinyl)propyl]amino]-alpha-2(1H)-pyridinylidene-4-pyrimidineacetonitrile,
2-[[2-(1 H-imidazol-4-yl)ethyl]amino]-5-methyl-alpha-2(1 H)-pyridinylidene-4-pyrimidineacetonitrile,
2-[[(1 S,2S)-2-hydroxycyclohexyl]amino]-5-methyl-alpha-2(1H)-pyridinylidene-4-pyrimidineacetonitrile,
2-(cyclopentylamino)-5-methyl-alpha-[6-[[2-(3 pyridiny)ethyl]amino]-2(1 H) -pyridinylidene]-4-pyrimidineacetonitrile,
2-(cyclopentylamino)-5-methyl-alpha-[6-[[3-(2-oxo-1-pyrrolidinyl)propyl]amino]2(1 H)-pyridinylidene]-4-pyrimidineacetonitrile,
2-(cyclopentylamino)-5-methyl-alpha-[6-[methyl(phenylmethyl)amino]-2(1 H) -pyridinylidene]-4-pyrimidineacetonitrile,
alpha-(3-bromo-2(1H)-pyridinylidene)-5-methyl-2-[[3-(3-oxo-4-morpholinyl)propyl]amino]-4-pyrimidineacetonitrile,
2-[[(1 S,2S)-2-(phenylmethoxy)cyclopentyl]amino]-alpha-2(1 H)-pyridinylidene-4-pyrimidineacetonitrile,
2-(cyclopentylamino)-alpha- [6-(2-pyridinylamino)-2(1 H)-pyridinylidene]-4-pyrimidineacetonitrile,
alpha-(3-bromo-2(1 H)-pyridinylidene)-5-methyl-2-[[3-(2-oxo- 1 pyrrolidinyl)propyl]amino]-4-pyrimidineacetonitrile,
2-(cyclopentylamino)-5-methyl-alpha-[6-[(trimethylsilyl)ethynyl]-2(1H) pyridinylidene]-4-pyrimidineacetonitrile, 2-(cyclopentylamino)-alpha-[6-(3-pyridinylamino)-2(1H)-pyridinylidene]-4-pyrimidineacetonitrile, 2-(cyclopentylamino)-alpha-[6-(cyclopentylamino)-2(1H)-pyridinylidene]-5-methyl-4-pyrimi dineacetonitrile, alpha-[3-(3-hydroxy-3-methyl-1-butynyl)-2(1 H)-pyridinylidene]-5-methyl-2[[3-(3 oxo-4-morpholinyl)propyl]amino]-4-pyrimidineacetonitrile, and alpha-(3-bromo-2(1 H)-pyridinylidene)-5-methyl-2-[[3-(1 H-1,2,4-triazol- 1-yl)propyl]amino]-4pyrimidineacetonitrile.

5. A pharmaceutical composition comprising a compound according to claim 1 and a pharmaceutically acceptable carrier, a diluent or an excipient thereof.

6. A method of preparing a compound of formula (Ib) according to claim 1, comprising the following step:

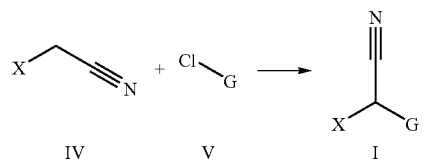

wherein X is a pyridinyl group and G is a pyrimidinyl or a triazinyl.

* * * * *